(12) United States Patent
Coghlan et al.

(10) Patent No.: US 6,719,520 B2
(45) Date of Patent: Apr. 13, 2004

(54) METHOD AND COMPOUNDS

(75) Inventors: Matthew Paul Coghlan, Bishops Stortford (GB); Ashley Edward Fenwick, Sandwich (GB); David Haigh, Harlow (GB); Julie Caroline Holder, Welwyn (GB); Robert John Ife, Harlow (GB); Alastair David Reith, Harlow (GB); David Glynn Smith, Harlow (GB); Robert William Ward, Harlow (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/446,553

(22) Filed: May 28, 2003

(65) Prior Publication Data

US 2004/0010031 A1 Jan. 15, 2004

Related U.S. Application Data

(63) Continuation of application No. 09/807,066, filed as application No. PCT/GB99/03280 on Oct. 5, 1999, now abandoned.

(30) Foreign Application Priority Data

| Oct. 8, 1998 | (GB) | 9821974 |
| Dec. 14, 1998 | (GB) | 9827521 |
| Dec. 17, 1998 | (GB) | 9827883 |
| Mar. 10, 1999 | (GB) | 9905518 |
| Mar. 26, 1999 | (GB) | 9907086 |
| Aug. 16, 1999 | (GB) | 9919362 |

(51) Int. Cl.⁷ .................. A61K 31/40; C01D 207/18
(52) U.S. Cl. .................. 414/425; 548/546; 548/547
(58) Field of Search .................. 548/546, 547; 414/425

(56) References Cited

U.S. PATENT DOCUMENTS

| 3,335,147 A | 8/1967 | Karten |
| 4,353,734 A | 10/1982 | Seres et al. |

FOREIGN PATENT DOCUMENTS

| DE | 40 05 969 A | 8/1991 |
| DE | 40 05 970 A | 8/1991 |
| EP | 0 328 026 A | 8/1989 |
| WO | WO 97/41854 | 11/1997 |
| WO | WO 98/11104 | 3/1998 |
| WO | WO 98/16528 | 4/1998 |
| WO | WO 99/57117 | 11/1999 |
| WO | WO 00/06564 | 2/2000 |

OTHER PUBLICATIONS

Zhang, et al., "Alkaloids from *Hypecoum leptocarpum*", Database accession No. 124:82090, (XP002135369), Database Chemabs 'Online!, Chemical Abstracts Services.

*Primary Examiner*—Joseph K. McKane
*Assistant Examiner*—Golam M M Shameem
(74) *Attorney, Agent, or Firm*—Amy H. Fix

(57) ABSTRACT

A method for the treatment of conditions associated with a need for inhibition of GSK-3, such as diabetes, dementias such as Alzheimer's disease and manic depression which method comprises the administration of a pharmaceutically effective, non-toxic amount of a compound of formula (I):

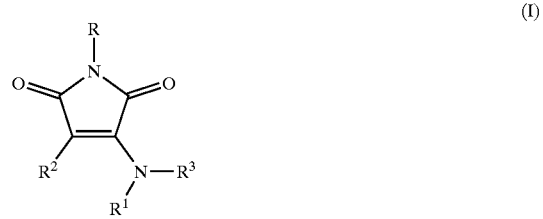

or a pharmaceutically acceptable derivative thereof, wherein:

R is hydrogen, alkyl, aryl, or aralkyl;

$R^1$ is hydrogen, alkyl, aralkyl, hydroxyalkyl or alkoxyalkyl;

$R^2$ is substituted or unsubstituted aryl or substituted or unsubstituted heterocyclyl;

$R^3$ is hydrogen, substituted or unsubstituted alkyl, cycloalkyl, alkoxyalkyl, substituted or unsubstituted aryl, substituted or unsubstituted heterocyclyl or aralkyl wherein the aryl moiety is substituted or unsubstituted; or, $R^1$ and $R^3$ together with the nitrogen to which they are attached form a single or fused, optionally substituted, saturated or unsaturated heterocylic ring;

to a human or non-human mammal in need thereof, and compounds of formula I.

2 Claims, No Drawings

METHOD AND COMPOUNDS

CROSS REFERENCES TO RELATED APPLICATIONS

This application is a continuation of U.S. Ser. No. 09/807, 066, filed Jun. 18, 2001, abandoned, which is a §371 of PCT(GB99/03280, filed on Oct. 5, 1999, which claims benefit from the following Provisional applications: GB 9919362.5, filed Aug. 16, 1999, GB 9907086.4, filed Mar. 26, 1999, GB 9905518.8, filed Mar. 10, 1999, GB 9827883.1, filed Dec. 17,1998, GB 9827521.7, filed Dec. 14,1998 and GB 9821974.4, filed Oct. 8, 1998.

This invention relates to a novel method for the treatment and/or prophylaxis of conditions associated with a need for inhibition of glycogen synthase kinase-3 (GSK-3), especially diabetes, including chronic neurodegenerative conditions, including dementias such as Alzheimer's disease, neurotraumatic diseases, such as acute stroke, mood disorders such as schizophrenia and manic depression, and for the treatment and/or prophylaxis of hair loss and cancer, and to certain novel inhibitors of GSK-3 for use in such a method.

GSK-3 is a serine/threonine protein kinase composed of two isoforms ($\alpha$ and $\beta$) which are encoded by distinct genes. GSK-3 is one of several protein kinases which phosphorylates glycogen synthase (GS) (Embi et al Eur. J. Biochem. (107) 519–527 (1980)). The $\alpha$ and $\beta$ isoforms have a monomeric structure of 49 and 47 kD respectively and are both found in mammalian cells. Both isoforms phosphorylate muscle glycogen synthase (Cross et al Biochemical Journal (303) 21–26 (1994)) and these two isoforms show good homology between species (e.g. human and rabbit GSK-3$\alpha$ are 96% identical).

Type II diabetes (or Non-Insulin Dependent Diabetes Mellitus, NIDDM) is a multifactorial disease. Hyperglycaemia is due to insulin resistance in the liver, muscle and other tissues coupled with inadequate or defective secretion of insulin from pancreatic islets. Skeletal muscle is the major site for insulin-stimulated glucose uptake and in this tissue, glucose removed from the circulation is either metabolised through glycolysis and the TCA cycle, or stored as glycogen. Muscle glycogen deposition plays the more important role in glucose homeostasis and Type II diabetic subjects have defective muscle glycogen storage.

The stimulation of glycogen synthesis by insulin in skeletal muscle results from the dephosphorylation and activation of glycogen synthase (Villar-Palasi C. and Lamer J. Biochim. Biophys. Acta (39) 171–173 (1960), Parker P J et al. Eur. J. Biochem. (130) 227–234 (1983), and Cohen P. Biochem. Soc. Trans. (21) 555–567 (1993)). The phosphorylation and dephosphorylation of GS are mediated by specific kinases and phosphatases. GSK-3 is responsible for phosphorylation and deactivation of GS, while glycogen bound protein phosphatase 1 (PP1G) dephosphorylates and activates GS. Insulin both inactivates GSK-3 and activates PP1G (Srivastava A K and Pandey S K Mol. and Cellular Biochem. (182) 135–141 (1998)).

Chen et al. Diabetes (43) 1234–1241 (1994) found that there was no difference in the mRNA abundance of PP1G between patients with Type II diabetes and control patients, suggesting that an increase in GSK-3 activity might be important in Type II diabetes. It has also recently been demonstrated that GSK-3 is overexpressed in Type II diabetic muscle and that an inverse correlation exists between skeletal muscle GSK-3$\alpha$ activity and insulin action (Nikoulina et al Glycogen Synthase Kinase-3 in Human Skeletal Muscle: Relationship To Insulin Resistance in Type II Diabetes. Diabetes (47(1)) 0028 Page A7 (1998) (Oral presentation)). Overexpression of GSK-3$\beta$ and constitutively active GSK-3$\beta$ (S9A, S9E) mutants in HEK-293 cells resulted in supression of glycogen synthase activity (Eldar-Finkelman et al., PNAS (93) 10228–10233 (1996)) and overexpression of GSK-3$\beta$ in CHO cells, expressing both insulin receptor and insulin receptor substrate 1 (IRS-1), resulted in an impairment of insulin action (Eldar-Finkelman and Krebs PNAS (94) 9660–9664 (1997)). Recent evidence for the involvement of elevated GSK-3 activity and the development of insulin resistance and type II diabetes in adipose tissue has emerged from studies undertaken in diabetes and obesity prone C57BL/6J mice (Eldar-Finkelman et al., Diabetes (48) 1662–1666 (1999)).

GSK-3 has been shown to phosphorylate other proteins in vitro including the eukaryotic initiation factor eIF-2B at Serine$^{540}$ (Welsh et al., FEBS Letts (421) 125–130 (1998)). This phosphorylation results in an inhibition of eIF-2B activity and leads to a reduction in this key regulatory step of translation. In disease states, such as diabetes, where there is elevated GSK-3 activity this could result in a reduction of translation and potentially contribute to the pathology of the disease.

Several aspects of GSK-3 functions and regulation in addition to modulation of glycogen synthase activity indicate that inhibitors of this enzyme may be effective in treatment of disorders of the central nervous system. GSK-3 activity is subject to inhibitory phosphorylation by PI 3 kinase-mediated or Wnt-1 class-mediated signals that can be mimicked by treatment with lithium, a low mM inhibitor of GSK-3 (Stambolic V., Ruel L. and Woodgett J. R Curr. Biol. 1996 6(12): 1664–8).

GSK-3 inhibitors may be of value as neuroprotectants in treatment of acute stroke and other neurotraumatic injuries. Roles for PI 3-kinase signalling through PKB/akt to promote neuronal cell survival are well established, and GSK-3 is one of a number of PKB/akt substrates to be identified that can contribute to the inhibition of apoptosis via this pathway (Pap & Cooper, (1998) J. Biol. Chem. 273: 19929–19932). Evidence suggests that astrocytic glycogen can provide an alternative energy source to facilitate neuronal survival under conditions of glucose deprivation (for example see Ransom, B. R. and Fern, R. (1997) Glia 21: 134–141 and references therein). Lithium is known to protect cerebellar granule neurons from death (D'Mello et al., (994) Exp. Cell Res. 211: 332–338 and Volonte et al (1994) Neurosci. Letts. 172: 6–10) and chronic lithium treatment has demonstrable efficacy in the middle cerebral artery occlusion model of stroke in rodents (Nonaka and Chuang, (1998) Neuroreport 9(9): 2081–2084). Wnt-induced axonal spreading and branching in neuronal culture models has been shown to correlate with GSK-3 inhibition (Lucas & Salinas. (1997) Dev. Biol. 192: 31–44) suggesting additional value of GSK-3 inhibitors in promoting neuronal regeneration following neurotraumatic insult.

Tau and $\beta$-catenin, two known in vivo substrates of GSK-3, are of direct relevance in consideration of further aspects of the value of GSK-3 inhibitors in relation to treatment of chronic neurodegenerative conditions. Tau hyperphosphorylation is an early event in neurodegenerative conditions such as Alzheimer's disease (AD), and is postulated to promote microtubule disassembly. Lithium has been reported to reduce the phosphorylation of tau, enhance the binding of tau to microtubules, and promote microtubule assembly through direct and reversible inhibition of glycogen synthase kinase-3 (Hong M., Chen D. C., Klein P. S. and Lee V. M. J. Biol. Chem. 1997 272(40) 25326–32). β-catenin is phosphorylated by GSK-3 as part of a tripartite complex with axin, resulting in β-catenin being targetted for degradation (Ikeda el al., (1998) EMBO J. 17: 1371–1384). Inhibition of GSK-3 activity is a key mechanism by which cytosolic levels of catenin are stabilised and hence promote β-catenin-LEF-1/TCF transcriptional activity (Eastman, Grosschedl (1999) Curr. Opin. Cell Biol. 11: 233). Rapid onset AD mutations in presenilin-1 (PS-1) have been shown to decrease the cytosolic β-catenin pool in transgenic mice. Further evidence suggests that such a reduction in available β-catenin may increase neuronal sensitivity to amyloid mediated death through inhibition of β-catenin-LEF-1/TCF transcriptional regulation of neutoprotective genes (Zhang et al., (1998) Nature 395: 698–702). A likely mechanism is suggested by the finding that mutant PS-1 protein confers decreased inactivation of GSK-3 compared with normal PS-1 (Weihl, C. C., Ghadge, G. D., Kennedy, S. G., Hay, N., Miller, R. J. and Roos, R. P.(1999) J. Neurosci. 19: 5360–5369).

WO 97/41854 (University of Pennsylvania) discloses that an effective drug for the treatment of manic depression is lithium but that there are serious drawbacks associated with this treatment. Whilst the precise mechanism of action of this drug for treatment of manic depression remains to be fully defined, current models suggest that inhibition of GSK-3 is a relevant target that contributes to the modulation of AP-1 DNA binding activity observed with this compound (see Manji et al., (1999) J. Clin. Psychiatry 60 (suppl 2): 27–39 for review).

GSK-3 inhibitors may also be of value in treatment of schizophrenia. Reduced levels of β-catenin have been reported in schizophrenic patients (Cotter D, Kerwin R, al-Sarraji S, Brion J P, Chadwich A, Lovestone S, Anderton B, Everall I, 1998 Neuroreport 9:1379–1383) and defects in pre-pulse inhibition to startle response have been observed in schizophrenic patients (Swerdlow et al., (1994) Arch. Gen. Psychiat. 51: 139–154). Mice lacking the adaptor protein dishevelled-1, an essential mediator of Wnt-induced inhibition of GSK-3, exhibit both a behavioural disorder and defects in pre-pulse inhibition to startle response (Lijam N, Paylor R, McDonald M P, Crawley J N, Deng C X, Herrup K, Stevens K E, Maccaferri G, McBain C J, Sussman DJ, Wynshaw-Boris A. (1997) Cell 90: 895–905). Together, these findings implicate deregulation of GSK-3 activity as contributing to schizophrenia. Hence, small molecule inhibitors of GSK-3 catalytic activity may be effective in treatment of this mood disorder.

The finding that transient β-catenin stabilisation may play a role in hair development (Gat el al., Cell (95) 605–614 (1998)) suggests that GSK-3 inhibitors could be used in the treatment of baldness.

Certain substitued 3-amino-4-arylmaleimides are disclosed in Tetrahedron (1998), 54(9), 1745–1752; Liebigs Annalen 1894, 282, 81; BE 659639; J Amer Chem Soc 1958, 80, 1385; J. Prakt. Chem. (1979), 321(5), 787–96; Eur. J. Org. Chem. (1998), (7), 1467–1470; Chem. Heterocycl. Compd. (N.Y.) (1997), 33(1), 69–73; J. Prakt. Chem. (1987), 329(4), 587–91; Collect, Czech. Chem. Commun. (1985), 50(6), 1305–11; Tetrahedron (1984), 40(18), 3499–502; J. Prakt. Chem. (1983), 325(2), 293–300; J Prakt Chem 1983, 325 (2) 293–300; Tetrahedron (1980), 36, 1801–5; which compounds have no disclosed pharmaceutical utility.

Certain 3-amino-4-arylmaleimides are disclosed in Bioorg. Med. Chem. Lett. (1995), 5(1), 67–72; J. Med. Chem. (1992), 35(1), 177–84; Tetrahedron Lett. (1990), 31(36), 5201–4; EP 328026; Bioorg. Med. Chem. Lett. (1994), 4(24), 2845–50, which compounds are disclosed as being protein kinase C inhibitors or trypanothione reductase inhibitors. Certain 3-amino-4-arylmaleimides are disclosed in DE 4005969 and DE 4005970 as having activity as anti-allergics and immunotherapeutics.

U.S. Pat. No. 3,335,147 discloses certain 3-amino-4-arylmaleimides as having topical anaesthetic activity. DE 19744257 discloses certain 3-amino-4-arylmaleimides as being tyrosine kinase inhibitors. Chem. Pharm. Bull. (1998), 46(4), 707–710 discloses certain 3-amino-4-arylmaleimides as being trypanothione reductase inhibitors. SA 672268 discloses certain 3-amino-4-arylmaleimides as being antimicrobials.

None of the above mentioned references discloses that the 3-amino-4-arylmaleimides possess GSK-3 inhibitor activity.

We have now discovered that a series of certain 3-amino-4-arylmaleimides are particularly potent and selective inhibitors of GSK-3. These compounds are indicated to be useful for the treatment and/or prophylaxis of conditions associated with a need for inhibition of GSK-3, such as diabetes, chronic neurodegenerative conditions, including dementias such as Alzheimer's disease, manic depression, mood disorders, such as schizophrenia, neurotraumatic diseases, such as acute stroke, hair loss, and cancer. Certain of these compounds are novel and such compounds comprise a further aspect of the invention. In addition, as indicated above it is considered that GSK-3 inhibitors per se are potentially useful in the treatment and/or prophylaxis of mood disorders, such as schizophrenia, neurotraumatic diseases, such as acute stroke, and for the treatment and/or prophylaxis of cancer and hair loss.

Accordingly, in a first aspect, the present invention provides a method for the treatment of conditions associated with a need for inhibition of GSK-3, such as diabetes, dementias such as Alzheimer's disease and manic depression which method comprises the administration of a pharmaceutically effective, non-toxic amount of a compound of formula (I):

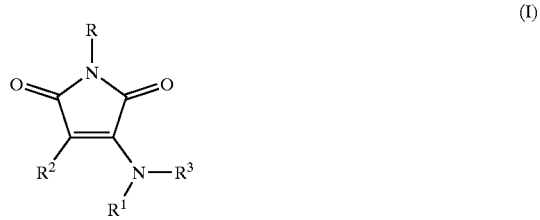

(I)

or a pharmaceutically acceptable derivative thereof, wherein:

R is hydrogen, alkyl, aryl, or aralkyl:

$R^1$ is hydrogen, alkyl, aralkyl, hydroxyalkyl or alkoxyalkyl;

$R^2$ is substituted or unsubstituted aryl or substituted or unsubstituted hetcrocyclyl;

$R^3$ is hydrogen, substituted or unsubstituted alkyl, cycloalkyl, alkoxyalkyl, substituted or unsubstituted aryl, substituted or unsubstituted heterocyclyl or aralkyl wherein the aryl moiety is substituted or unsubstituted; or, $R^1$ and $R^3$ together with the nitrogen to which they are attached form a single or fused, optionally substituted, saturated or unsaturated heterocylic ring;

to a human or non-human mammal in need thereof.

Suitably, R is hydrogen, $C_{1-6}$alkyl, such as methyl or ethyl, or R is phenyl or benzyl.

Preferably, R is hydrogen.

Suitably, $R^1$ is hydrogen, $C_{1-6}$alkyl, such as methyl, ethyl, or $R^1$ is hydroxyethyl or methoxyethyl.

Preferably, $R^1$ is hydrogen.

When $R^2$ is substituted or unsubstituted aryl, examples of aryl groups include phenyl and naphthyl.

When $R^2$ is substituted or unsubstituted heterocyclyl, examples of heterocyclyl groups include indolyl, benzofuranyl, thienyl and benzothienyl.

When $R^2$ is substituted phenyl, suitable substituents include up to three groups independently selected from halo, $C_{1-6}$alkoxy, nitro, perfluoro$C_{1-6}$alkyl, benzoyl, $C_{1-6}$alkoxycarbonyl, $C_{1-6}$alkylsulphonyl, hydroxy, —O(CH$_2$)$_w$O— where w is 1 to 4, phenoxy, benzyloxy, $C_{1-6}$alkoxy$C_{1-6}$alyl, perfluoro$C_{1-6}$alkoxy, $C_{1-6}$alkylS—, perfluoro$C_{1-6}$alkylS—, (di$C_{1-6}$alkyl)N—, amino, $C_{1-6}$alkylcarbonylamino, substituted or unsubstituted ureido, phenylcarbonylamino, benzylcarbonylamino, styrylcarbonylamino, (di$C_{1-6}$alkoxy)(phenyl)C—, C alkyl, and phenyl. Suitable substituents for ureido include fluorophenyl, phenyl$C_{1-6}$alkyl-, cyclohexyl, $C_{1-6}$alkenyl, $C_{1-6}$alkyl, and $C_{1-6}$alkoxyphenyl.

When $R^2$ is substituted indolyl, suitable substituents include $C_{1-6}$alkyl.

When $R^2$ is substinned benzothienyl, suitable substituents include $C_{1-6}$alkyl.

Suitably, $R^2$ is substituted or unsubstituted phenyl.

Favourably, $R^2$ is phenyl substituted with;

4-Cl: 3-Cl: 2-Cl: 2,4-di-Cl; 3,4-di-Cl: 3,5-di-Cl; 2,6-di-Cl; 2-F-6-Cl; 2-F; 3-F; 2,3-di-F; 2,5-di-F; 2,6-di-F; 3,4-di-F; 3,5-di-F; 2,3,5-tri-F; 3,4,5-tri-F; 2-Br; 3-Br; 4-Br; 2-I; 4-I; 3-Cl-4-OMe; 3-NO$_2$-4-Cl; 2-OMe-5-Br, 2-NO$_2$; 3-NO$_2$; 2-CF$_3$; 3-CF$_3$; 4-CF$_3$; 3,5-di-CF$_3$; 4-PhC(O); 4-MeO(O)C—; 4-MeSO$_2$—; 4-OH; 2-OMe; 3-OMe; 4-OMe; 2,4-di-OMe; 2,5-di-OMe; 3,4-di-OMe; 3,4-OCH$_2$O—; 3,4,5-tri-OMe; 3-NO$_2$-4-OMe; 4-OnBu; 2-OEt; 2-OPh; 3-OPh; 4-OPh; 2-OCH$_2$Ph; 4-OCH$_2$Ph; 4-(MeOCH$_2$); 2-OCF$_3$; 4-OCF$_3$; 4-SMe; 3-SCF$_3$; 4-NMe$_2$; 3-NH$_2$; 3-(NHC(O)Me); 3-[NHC(O)NH(3-F-Ph)]; 3-[NHC(O)NH(CH$_2$)$_2$Ph]; 3-[NHC(O)NHCyclohexyl]; 3-[NHC(O)NHCH$_2$CH=CH$_2$]; 3-[NHC(O)Ph]; 3-[NHC(O)CH$_2$Ph]; 3-[trans-NHC(O)CH=CHPh]; 3-[NHC(O)nPr]; 3-[NHC(O)NHEt]; 3-[NHC(O)NH(3-OMe-Ph)]; 4-[C(OMe)$_2$Ph]; 2-Me: 3-Me; 4-Me; 4-iPr; 2,5-di-Me; 3,5-di-Me, 4-Ph, 2,3-[(—CH$_2$=CH$_2$—)], or 3,4-[(—CH$_2$=CH$_2$—)].

When $R^3$ is alkyl, examples include methyl and ethyl.

When $R^3$ is cycloalkyl, examples include cyclohexyl.

When $R^3$ is alkoxyalkyl, examples include methoxyethyl.

When $R^3$ is aralkyl, examples include benzyl and phenylethyl.

When $R^3$ is substituted or unsubstituted aryl, examples include fluorenyl, phenyl, and dibenzofuryl.

When $R^3$ is substituted or unsubstituted heterocyclyl, examples include thienyl, oxazolyl, benzoxazolyl, pyridyl, and pyrimidinyl.

When $R^1$ and $R^3$ together with the nitrogen atom to which they are attached form a fused heterocyclic ring, which ring may be unsubstituted or substituted, examples include indolinyl, indolyl, oxindolyl, benzoxazolinonyl, tetahydroquinolinyl, tetrahydroisoquinolinyl, benzimidazolyl, benzazepinyl, isoindolin-2-yl, and 1,3,3-trimethyl-6-azabicyclo[3,2,1]oct-6-yl.

When $R^1$ and $R^3$ together with the nitrogen atom to which they are attached form a single heterocyclic ring, which ring may be unsubstituted or substituted, examples include 1-phenyl-1,3,8-triazaspiro-[4,5]-decan-4-one-8-yl, piperazinyl, pyrrolidinyl, piperidinyl, morpholinyl, thiomorpholinyl, and a pyridiniun ring.

When $R^3$ is substituted phenyl, suitable substituents include up to three groups independently selected from substituted or unsubstituted $C_{1-6}$alkyl, phenyl, benzyl, substituted or unsubstituted $C_{1-6}$alkylS—, halo, hydroxy, substituted or unsubstituted $C_{1-6}$alkoxy, substituted or unsubstituted phenoxy, indolyl, naphthyl, carboxy, $C_{1-6}$alkoxycarbonyl, benzyloxy, pentafluorophenoxy, nitro, N-substituted or unsubstituted carbamoyl, substituted or unsubstituted $C_{1-6}$alkycarbonyl, berzoyl, cyano, perfluoro$C_{1-6}$alkylSO$_2$—, $C_{1-6}$alkylNHSO$_2$—, oxazolyl, $C_{1-6}$alkylcarbonylpiperazinyl, substituted or unsubstituted phenylS—, $C_{1-6}$alkylpiperazinyl-, cyclohexyl, adamantyl, trityl, substituted or unsubstituted $C_{1-6}$alkenyl, perfluoro$C_{1-6}$alkyl, perfluoro$C_{1-6}$alkoxy, perfluoro$C_{1-6}$alkylS—, aminosulphonyl, alkylaminosulphonyl, dialkylaminosulphonyl, arylaminosulphonyl, morpholino, (di$C_{1-6}$alkyl)amino, $C_{1-6}$alkylCONH—, (di$C_{1-6}$alkoxy)phenyl(CH$_2$)$_n$NHC(O)CH(phenyl)S— where n is 1 to 6, and $C_{1-6}$alkylCON($C_{1-6}$alkyl)—, thiazolidinedionyl$C_{1-6}$alkly, phenylCH(OH)—, substituted or unsubstituted piperazinyl$C_{1-6}$alkoxy, substituted or unsubstituted benzoylamino: or —[CH=CH—C(O)O]—, —[(CH=CH)$_2$]—, —[(CH$_2$)$_x$N($C_{1-6}$alkylcarbonyl)]—, —(CH$_2$)$_x$—, —SCH=N—, —SC($C_{1-6}$alkyl)=N—, —OCF$_2$O—, —CH=N—NH—, —CH=CH—NH—, —OC(NHC$_{1-6}$alkyl)=N—, —OC(O)NH—, —C(O)NC$_{1-6}$alkylC(O)—, —[CH=CH—CH=N]—, —[CH=C($C_{1-6}$alkylcarbonyl)O]—, —C(O)NHC(O)—, —[(CH$_2$)$_x$C(O)]—, —N=N—NH—, —N=C($C_{1-6}$alkyl)O—, —O(CH$_2$)$_x$O—. —(CH$_2$)$_x$SO$_2$(CH$_2$)$_y$—, —N($C_{1-6}$alkylcarbonyl)(CH$_2$)$_x$— where x and y are independently 1 to 4, pyrimidin-2-yloxy, phenylamino, N-[pyrimidin-2-yl]-N-[$C_{1-6}$alkyl]amino, $C_{1-6}$alkylsulphonylamino, and 1,2,3-thiadiazolyl.

Suitable substituents for $C_{1-6}$alkyl include hydroxy, carboxy, unsubstituted or N-substituted carbonyl, N-morpholinylcarbonyl, $C_{1-6}$alkylaminocarbonyl, fluoro, cyano, $C_{1-6}$alkyl, $C_{1-6}$alkoxycarbonylamino, amino, $C_{1-6}$alkylcarbonylamino, benzoylamino, phenylaminocarbonylamino, $C_{1-6}$alkoxycarbonyl, phosphono. mono-or bis$C_{1-6}$alkylphosphonate, $C_{1-6}$alkylaminosulphonyl, and $C_{1-6}$alkylcarbonylamino$C_{1-6}$ alkylaminoCO—, Suitable substituents for $C_{1-6}$alkylS— include carboxy, $C_{1-6}$alkoxycarbonyl, $C_{1-6}$alkoxy$C_{1-6}$alkylaminocarbonyl, unsubstituted or N-substituted carbamoyl, and fluoro.

Suitable substituents for $C_{1-6}$alkoxy include $C_{1-6}$alkoxy, phenyl, carboxy, $C_{1-6}$alkoxycarbonyl, unsubstituted or N-substituted carbamoyl, and phenyl.

Suitable substituents for carbamoyl include $C_{1-6}$alkyl, and $C_{1-6}$alkoxy$C_{1-6}$alkyl.

Suitable substituents for $C_{1-6}$alkylcarbonyl include carboxy, and $C_{1-6}$alkoxycarbonyl.

Suitable substituents for phenylS— include chloro, nitro, carboxy, $C_{1-6}$alkylaminocarbonyl, unsubstituted or N-substituted carbamoyl, and $C_{1-6}$alkoxycarbonyl.

Suitable substituents for $C_{1-6}$alkenyl include (di$C_{1-6}$alkyl)aminocarbonyl, carboxy, $C_{1-6}$alkoxycarbonyl, carbamoyl, and phenyl.

Suitable substituents for piperazinyl$C_{1-6}$alkoxy include methyl.

Suitable substituents for phenoxy include chloro.

Suitable substiments for benzoylamino include hydroxy.

When $R^3$ is substituted benzofuryl, suitable substituents include $C_{1-6}$alkylcarbonyl.

When $R^3$ is substituted thienyl, suitable substituents include $C_{1-6}$alkylcarbonyl.

When $R^3$ is substituted oxazolyl, suitable substituents include $C_{1-6}$alkyl.

When $R^3$ is substituted benzoxazolyl, suitable substituents include halo.

When $R^3$ is substituted pyridyl, suitable substituents include up to three substituents independently selected from $C_{1-6}$alkyl, $C_{1-6}$alkoxy, and halo.

Suitably, $R^3$ is substituted or unsubstituted phenyl.

Favourably, $R^3$ is phenyl substituted with;

2-Me: 2-Et; 2-iPr; 2-CH$_2$OH; 2-Ph; 2-CH$_2$Ph; 2-SMe; 2-F; 2-Cl; 2-OH; 2-OMe; 2-OPh; 2-Me-5-F; 2-Me-3-Cl; 2-Me-4-Cl; 2-Me-5-Cl; 2-Me-3-Br; 2,3-di-Me; 2,4-di-Me; 2-Me-4OH; 2-Me-4-OMe; 2-Me-5-CH$_2$OH; 2,4,6-tri-Me; 2-(2-Indolyl); (1-Naphthyl); 2-Me-5-COOH; 2-Me-5-COOMe; 2-OH-5-COOH; 2-[O(CH$_2$)$_2$OMe]-5-[(CH$_2$)$_2$COOH]; 2-[SCH(Ph)CONH(CH$_2$)$_2$(3,4-di-OMePh)]; 3-Me; 3-Et; 3-CH$_2$OH; 3-CH$_2$OH-6-Me; 3-CH$_2$OH-4-OMe; 3-CH$_2$NMe$_2$)-4-OMe; 3-[CH$_2$COOH]; 3-[CH$_2$COOMe]; 3-[CH$_2$CONH$_2$]; 3-[CH$_2$CONHMe]; 3-[CH$_2$-(thiazolidine-2,4-dion-5-yl)]: 3-SMe; 3-F; 3-Cl; 3-Br; 3-I; 3-CF$_3$; 3-OH; 3-OMe; 3-OCH$_2$Ph; 3-O-pentafluorophenyl; 3-(OCH$_2$CO$_2$H); 3-(OCH$_2$CO$_2$Me); 3-(OCH$_2$CO$_2$Et); 3-NO$_2$; 3-CO$_2$H; 3-CO$_2$Me; 3-CONH$_2$; 3-CONHMe; 3-CONHCH$_2$CH$_2$OMe; 3-COMe; 3-COPh; 3-(COCH$_2$CH$_2$CO$_2$H); 3-(COCH$_2$CH$_2$CO$_2$Me); 3-CN; 3-SO$_2$CF3; 3-SO$_2$NH-nBu; 3-(5-oxazolyl); 3-[4-methylpiperazin-1-yl]OMe; 3-[O-(pyrimidin-2-yl)]; 3-OH-4-OMe; 3,4-di-OMe; 3,5-di-OMe; 3,4-di-Me; 3,5-di-Me; 3-[trans-CH=CHCONMe$_2$]-4-Cl; 3-F-4-Me; 3-Cl-4-Me; 3-Br-4-Me; 3,5-di-F; 3,4-di-Cl; 3,5-di-Cl; 3,5-di-Br; 3-Cl-4-Br; 3-Cl-4-I; 3-Cl-4-OH; 3-Br-4-OH; 3-F-4-OMe; 3-Cl-4-OMe; 3-Cl-4-SMe; 3-Br-4-Cl: 3-Br-4-OCF$_3$; 3-Br-5-CF$_3$; 3,5-di-Cl-4-OH; 3,5-di-Br-4-OH; 3,5-di-Cl-4-Me; 3,5-di-Br-4-Me: 3-[CH$_2$CH(Me)CO$_2$H]; 3-CO$_2$H-4-Cl; 3-CO$_2$Me-4-Cl; 3-CO$_2$H-4-OH; 3-CO$_2$CONH$_2$-4-Me; 3-NO$_2$-4-OH; 3-CO$_2$H-4-SPh; 3-CO$_2$H-4-[S-(2-CO$_2$H-Ph)]; 3-CO$_2$H-4-[S-(2-CONHMe-Ph)]; 3-CO$_2$Et-4-[S-(2-CO$_2$Et-Ph)]; 3-CO$_2$H-4-[S-(3-CO$_2$H-Ph)]; 3-CO$_2$Me-4-[S-(4-Cl-Ph)]; 4-[N(Me)(Pyrimidin-2-yl)]; 4-Me; 4-nBu; 4-tBu; 4-Cyclohexyl; 4-Adamantyl; 4-CPh$_3$; 4-CH$_2$CN; 4-CH(OH)Me; 4-CH(OMe)Me; 4-CH$_2$OH; 4-CH$_2$NHC(O)t-Bu; 4-CH$_2$NH$_2$; 4-CH$_2$NHCOMe; 4-CH$_2$NHCOPh; 4-CH$_2$NHCONHPh; 4-CH$_2$CO$_2$H; 4-CH$_2$CO$_2$Me; 4-[CH$_2$P(O)(OH)$_2$]; 4-[CH$_2$P(O)(OEt)$_2$]; 4-[CH$_2$SO$_2$NHMe]; 4-(CH$_2$)$_2$OH: 4-(CH$_2$)$_2$NH$_2$; 4-(CH$_2$)$_2$NHCOPh; 4-(CH$_2$)$_2$NHC(O)Ot-Bu; 4-[(CH$_2$)$_2$ CO$_2$H); 4-[(CH$_2$)$_2$CO)Me]; 4-(CH$_2$CH$_2$CONH$_2$); 4-[CH$_2$CH$_2$CONH(CH$_2$)$_6$NHCOMe]; 4-[(CH$_2$)$_3$ CO$_2$H]; 4-[(CH$_2$)$_3$CO$_2$Me]; 4-[CH=CH$_2$]; 4-(CH=CHCO$_2$H); 4-(CH=CHCO$_2$Et); 4-(CH=CHCONH$_2$); 4-(CH=CHPh); 4-(CH=CH(4-OHPh)); 4-[1,2,3-thiadiazol-4-yl]; 4-[OCH$_2$-(1-methyl-piperazn-4-yl)]; 4-[4-methylpiperazin-1-yl]; 4-CF$_3$; 4-SMe: 4-(SCH$_2$CO$_2$H); 4-(SCH$_2$CO$_2$Me); 4-[SCH$_2$CONH(CH$_2$)$_2$OMe]; 4-SCF$_3$; 4-[S-(4-NO$_2$-Ph)]; 4-[S-(2-CO$_2$H-Ph)]; 4-[S-(3-CO$_2$H-Ph)]; 4-SO$_2$NH$_2$; 4-F; 4-Cl; 4-Br; 4-OH; 4-OMe: 4-OnBu; 4-OPh; 4-[O-(4-Cl-Ph)]; 4-OCH$_2$Ph; 4-OCH$_2$CO$_2$Me; 4-COPh; 4-COMe; 4-CONH$_2$; 4-CO$_2$H; 4-CN; 4-NO$_2$; 4-morpholinyl; 4-[CH$_2$CO-morpholin-1-yl)]; 4-[CH$_2$CONH(CH$_2$)$_2$OMe]; 4-[(CH$_2$)$_2$CONH(CH$_2$)$_6$NHC(O)Ot-Bu]; 4-[(CH$_2$)$_2$CONH(CH$_2$)$_6$NH$_2$]; 4-[(CH$_2$)$_2$CONH(CH$_2$)$_6$NH-biotinyl]; 4-NMe$_2$; 4-NHCOMe; 4-N(Me)COMe, 2,3-di-F; 4-[NHCO(Ph-2-OH)], 4-(phenylamino); 4-methylsulphonylamino, 2,4-di-F; 2,5-di-F; 2-OMe-3-F; 3-CH$_2$OMe; 3-CH(OH)Ph; 3,4-di-F; 3-CO$_2$H-4-CH$_2$CO$_2$H; 3-CO$_2$H-4-[S-(2-CO$_2$Et)Ph]; 3-CO$_2$Et-4-[S-(4-CO$_2$H)Ph]; 3-CONHMe-4-[S-(2-CONHMe)-Ph]; 3-[4-dichloroacetyl)piperazin-1-yl]-4-OMe; 4-CH$_2$CONH$_2$; 4-SPh; 4-[S-(4-CO$_2$H-Ph)]; and 4-OCH$_2$CO$_2$H.

When $R^1$ and $R^3$ together with the nitrogen, atom to which they are attached form indolinyl, suitable substituents include $C_{1-6}$alkyl, perfluoro$C_{1-6}$alkyl, $C_{1-6}$alkylSO$_2$NH-hydroxy$C_{1-6}$alkyl, carboxy, $C_{1-6}$alkoxycarbonyl, $C_{1-6}$alkoxy, halo, t-butoxycarbonylpiperazin-1-yl, 4-($C_{1-6}$alkyl)piperazinyl, piperazinyl, amido, and nitro.

When $R^1$ and $R^3$ together with the nitrogen atom to which they are attached form piperazinyl, suitable substituents include alkylcarbonyl, alkyl, or aryl.

When $R^1$ and $R^3$ together with the nitrogen atom to which they are attached form tetrahydroquinolinyl, suitable substituents include perfluoro$C_{1-6}$alkyl.

When $R^1$ and $R^3$ together with the nitrogen atom to which they are attached form a pyridinium ring, suitable substituents include amino.

When $R^1$ and $R^3$ together with the nitrogen atom to which they are attached form pyrrolidinyl, suitable substituents include hydroxy.

When $R^1$ and $R^3$ together with the nitrogen atom to which they are attached form piperidinyl, suitable substituents include benzyl, hydroxy$C_{1-6}$alkyl, $C_{1-6}$alkyl, hydroxy, carbamoyl, and $C_{1-6}$alkoxycarbonyl.

When $R^1$ and $R^3$ together with the nitrogen atom to which they are attached form oxindolyl, suitable substituents include $C_{1-6}$alkyl.

There is a sub-group of compounds, falling wholly within formula (I), and being of formula (IA), wherein R, $R^1$, $R^2$ and $R^3$ are as defined in relation to formula (I), with the proviso that formula (IA) does not include the following compounds, hereinafter referred to as List A:

3-phenyl-4-(4-methylpiperazino)-pyrrale-2,5-dione;

3-[4-diphenylmethyl)-1-piperazinyl]-4-(1H-indol-3-yl)-1-methyl-1H-pyrrole-2,5-dione;

3-phenyl-4-(4-phenylpiperazino)-pyrrole-2,5-dione;

1-methyl-3-phenyl-4-(4-phenylpiperazino)-pyrrole-2,5-dione;

1-ethyl-1-phenyl-4-(4-chlorophenylpiperazino)-pyrrole-2,5-dione;

1-allyl-3-phenyl-4-(4-methylpiperazino)pyrrole-2,5-dione;

3-indol-1-yl-4-(1-methyl-1H-indol-3-yl)-pyrrole-2,5-dione;

1-(1-methyl-2,5-dioxo-4-phenylamino-2,5-dihydro-1H-pyrrol-3-yl)pyridinium chloride;

1-[1-(4-methyl-pentyl)-2,5-dioxo-4-phenylamino-2,5-dihydro-1H-pyrrol-3-yl]pyridinium chloride;

1-(1-dodecyl-2,5-dioxo-4-phenylamino-2,5-dihydro-1H-pyrrol-3-yl)-pyridinium chloride;

3-[2-benzo[b]thien-2-yl-3-[4-(dimethylamino)-2,5-dihydro-2,5-dioxo-1H-pyrrol-3-yl]-1H-indol-1-yl]-carbamimidothioic acid, propyl ester;

3-(dimethylamino)-4-(1H-indol-3-yl)-1-methyl-1H-pyrrole-2,5-dione;

3-(1H-indol-3-yl)-1-methyl-4(phenylamino)-1H-pyrrole-2,5-dione;

3-(1H-indol-3-yl)-1-methyl-4-([[4-(trifluoromethyl)phenyl]amino]-1H-pyrrole-2,5-dione;

3-(1H-indol-3-yl)-1-methyl-4-(methylamino)-1H-pyrrole-2,5-dione;

3-(1H-imidazo[4,5-b]pyridin-1-yl)-4-(1H-indol-3-yl)-1-methyl-1H-pyrrole-2,5-dione;

3-(6-chloro-9H-purin-9-yl)-4-(1H-indol-3-yl)-1-methyl-1H-pyrrole-2,5-dione;

3-(6-amino-9H-purin-9-yl)-4-(1H-indol-3-yl)-1-methyl-1H-pyrrole-2,5-dione;

3-(1H-indol-3-yl)-1-methyl-4-(1H-pyrrolo[2,3-b]pyridin-1-yl)-1H-pyrrole-2,5-dione;

3-(1H-indol-3-yl)-1-methyl-4-(1-piperidinyl)-1H-pyrrole-2,5-dione;

1-acetyl-3-[2,5-dihydro-1-methyl-2,5-dioxo-4-[[4-(trifluoromethyl)phenyl]amino]-1H-pyrrol-3-yl]-1H-indole;

3-(1H-benzimidazol-1-yl)-4-(1H-indol-3-yl)-1-methyl-1H-pyrrole-2,5-dione;

3-(1H-benzotriazol-1-yl)-4-(1H-indol-3-yl)-1-methyl-1H-pyrrole-2,5-dione;

3-(1H-imidazol-1-yl)-4-1H-indol-3-yl)-1-methyl-1H-pyrrole-2,5-dione;

3-(1H-indol-1-yl)-4-(1H-indol-3-yl)-1-methyl-1H-pyrrole-2,5-dione;

3-(1H-indazol-1-yl)-4-1H-indol-3-yl)-1-methyl-1H-pyrrole-2,5-dione;

3-(3-[(dimethylamino)methyl]-1H-indol-1-yl]-4-(1H-indol-3-yl)-1-methyl-1H-pyrrole-2,5-dione;

3-(1H-benzimidazol-1-yl)-4-(1H-indol-3-yl)-1H-pyrrole-2,5-dione;

3-(1H-indol-1-yl)-4-(1-methyl-1H-indol-3-yl)1H-pyrrole-2,5-dione;

3-amino-4-(1H-indol-3-yl)-1H-pyrrole-2,5-dione;

3-amino-4-(5-methoxy-1H-indol-3-yl)-1H-pyrrole-2,5-dione;

1H-Indole-1-carboxylic acid, 3-(4-amino-2,5-dihydro-1-methyl-2,5-dioxo-1H-pyrrol-3-yl)-, 1,1-dimethylethyl ester;

3-(1H-indol-3-yl)-1-methyl-4-[(phenylmethyl)amino]-1H-pyrrole-2,5-dione;

Gylcine, N-[2,5-dihydro-4-(1H-indol-3-yl)-1-methyl-2,5-dioxo-1H-pyrrol-3-yl]-, ethyl ester;

3-amino-4-(1H-indol-3-yl)-1-methyl-1H-pyrrole-2,5-dione;

3-[[3[(3-aminopropyl)amino]propyl]amino]-4-1H-indol-3-yl)-1H-pyrrole-2,5-dione;

[[3-[4-(3-aminopropyl)-1-piperazinyl]propyl]amino]-4-(1H-indol-3-yl)-1H-pyrrole-2,5-dione;

3-(1H-indol-3-yl)-4-[[3-(4-methyl-1-piperazinyl)propyl]amino]-1H-pyrrole-2,5-dione;

1-[3-[(3-aminopropyl)amino]propyl]-3-[[3-[(3-aminopropyl)amino]propyl]amino]-4-1H-indol-3-yl)-1H-pyrrole-2,5-dione;

1-[3-[4-(3-aminopropyl)-1-piperazinyl]propyl]-3-[[3-[4-(3-aminopropyl)-1-piperazinyl]propyl]amino]-4-(1H-indol-3-yl)-1H-pyrrole-2,5-dione;

3-(1H-indol-3-yl)-1-[3-(4-methyl-1-piperazinyl)propyl]-4-[[3-(4-methyl-1-piperazinyl)propyl]amino]-1H-pyrrole-2,5-dione;

3,3'-[iminobis(3,1-propanediylimino)]bis[4-(1H-indol-3-yl)-1H-pyrrole]-2,5-dione;

3,3'-[1,4-piperazinediylbis(3,1-propanediylimino)]bis[4-(1H-indol-3-yl)-1H-pyrrole-2,5-dione;

3-[(5-aminopentyl)amino]-4-(1H-indol-3-yl)-1H-pyrrole-2,5-dione;

3-[[5-(2-aminoethyl)amino]pentyl]amino]-4-(1H-indol-3-yl)-1H-pyrrole-2,5-dione;

3-[(2-aminoethyl)amino]-4-(1H-indol-3-yl)-1H-pyrrole-2,5-dione;

3-[(6-aminohexyl)amino]-4-(1H-indol-3-yl)-1H-pyrrole-2,5-dione;

3-[(7-aminoheptyl)amino]-4-(1H-indol-3-yl)-1H-pyrrole-2,5-dione;

3-[[2-[(2-aminoethyl)amino]ethyl]amino]-4-(1H-indol-3-yl)-1H-pyrrole-2,5-dione;

Benzenepropanamide, .alpha.-amino-N-[5-[[2,5-dihydro-4-(1H-indol-3-yl)-2,5-dioxo-1H-pyrrol-3-yl]amino]pentyl]-, (S)-;

Pentanoic acid, 4-amino-5-[[5-[[2,5-dihydro-4-(1H-indol-3-yl)-2,5-dioxo-1H-pyrrol-3-yl]amino]pentyl]amino]-5-oxo-, (S)-;

Pentanamide, 2-amino-5-[(aminoiminomethyl)amino]-N-[2-[[5-[[2,5-dihydro-4-(1H-indol-3-yl)-2,5-dioxo-1H-pyrrol-3-yl]amino]pentyl]amino]ethyl]-, (S)-;

Benzenepropanamide, .alpha.-amino-N-[2-[[5-[[2,5-dihydro-4-(1H-indol-3-yl)-2,5-dioxo-1H-pyrrol-3-yl]amino]pentyl]amino]ethyl]-, (S)-;

Butanamide, 4-[(aminoiminomethyl)amino]-N-[5-[[2,5-dihydro-4-(1H-indol-3-yl)-2,5-dioxo-1H-pyrrol-3-yl]amino]pentyl]-, (S)-;

3-phenyl-4-diethylamino)-pyrrole-2,5-dione;

3-phenyl-4-(benzylamino)-pyrrole-2,5-dione;

1-methyl-3-phenyl-4-(2-diethylaminoethylamino)-pyrrole-2,5-dione;

1-allyl-3-phenyl-4-(2-dimethylaminoethylamino)-pyrrole-2,5-dione; and;

1,3-diphenyl-4-piperidino-pyrrole-2,5-dione.

There is a further sub-group of compounds, falling wholly within formula (I), and being of formula (IB), wherein R, $R^1$, $R^2$ and $R^3$ are as defined in relation to formula (I), with the proviso that formula (IB) does not include the following compounds, hereinafter referred to as List B:

3-(4-methylpiperazin-1-yl)-4-phenyl-pyrrole-2,5-dione;

3-(4-ethylpiperazin-1-yl)-4-phenyl-pyrrole-2,5-dione;

3-(4-chlorophenyl)-4-(4-methyl-piperazin-1-yl)-pyrrole-2,5-dione;

3-[4-(diphenylmethyl)-1-piperazinyl]-4-(1H-indol-3-yl)-1-methyl-1H-pyrrole-2,5-dione;

3-phenyl-4-(4-methylpiperazino)-pyrrole-2,5-dione;

3-phenyl-4-(4-phenylpiperazino)-pyrrole-2,5-dione;

1-methyl-3-phenyl-4-(4-phenylpiperazino)-pyrrole-2,5-dione;

1-ethyl-3-phenyl-4-(4-chlorophenylpiperazino)-pyrrole-2,5-dione;

1-allyl-3-phenyl-4-(4-methylpiperazino)pyrrole-2,5-dione;

3-phenylamino-4-phenyl-1H-pyrrole-2,5-dione;

3-phenyl-4-piperidin-1-yl-pyrrole-2,5-dione;

3-(3,5-dimethyl-1-phenyl-1H-pyrazol-4-yl)-4-morpholin-4-yl-pyrrole-2,5-dione;

3-indol-1-yl-4-(1-methyl-1H-indol-3-yl)-pyrrole-2,5-dione;

1-(1-methyl-2,5-dioxo-4-phenylamino-2,5-dihydro-1H-pyrrol-3-yl)pyridinium chloride;

1-1-(4-methyl-pentyl)-2,5-dioxo-4-phenylamino-2,5-dihydro-1H-pyrrol-3-yl)-pyridinium chloride;

1-(1-dodecyl-2,5-dioxo-4-phenylamino-2,5-dihydro-1H-pyrrol-3-yl)-pyridinium chloride;

3-[2,5-dihydro-4-(1H-imidazol-1-yl)-1-methyl-2,5-dioxo-1H-pyrrol-3-yl]-1H-indole-1-carboxylic acid, 1,1-dimethylethyl ester;

3-[2-benzo[b]thien-2-yl-3-[4-dimethylamino)-2,5-dihydro-2,5-dioxo-1H-pyrrol-3-yl]-1H-indol-1-yl]-carbamimidothioic acid, propyl ester;

3-(dimethylamino)-4-(1H-indol-3-yl)-1-methyl-1H-pyrrole-2,5-dione;

3-(1H-indol-3-yl)-1-methyl-4-(phenylamino)-1H-pyrrole-2,5-dione;

3-(1H-indol-3-yl)-1-methyl-4-[[4-(trifluoromethyl)phenyl]amino]-1H-pyrrole-2,5-dione;

3-(1H-indol-3-yl)-1-methyl-4-(methylamino)-1H-pyrrole-2,5-dione;

3-(1H-imidazo[4,5-b]pyridin-1-yl)-4-(1H-indol-3-yl)-1-methyl-1H-pyrrole-2,5-dione;

3-(6-chloro-9H-purin-9-yl)-4-(1H-indol-3-yl)-1-methyl-1H-pyrrole-2,5-dione;

3-(6-amino-9H-purin-9-yl)-4-(1H-indol-3-yl)-1-methyl-1H-pyrrole-2,5-dione;

3-(1H-indol-3-yl)-1-methyl-4-(1H-pyrrolo[2,3-b]pyridin-1-yl)-1H-pyrrole-2,5-dione;

3-(1H-indol-1-yl)-1-methyl-4-(1-piperidinyl)-1H-pyrrole-2,5-dione;

1-acetyl-3-[2,5-dihydro-1-methyl-2,5-dioxo-4-[[4-(trifluoromethyl)phenyl]amino]-1H-pyrrol-3-yl]-1H-indole:

3-(1H-benzimidazol-1-yl)-4-(1H-indol-3-yl)-1-methyl-1H-pyrrole-2,5-dione;

3-(1H-benzotriazol-1-yl)-4-(1H-indol-3-yl)-1-methyl-1H-pyrrole-2,5-dione;

3-(1H-imidazol-1-yl)-4-(1H-indol-3-yl)-1-methyl-1H-pyrrole-2,5-dione;

3-(1H-indol-1-yl)-4-(1H-indol-3-yl)-1-methyl-1H-pyrrole-2,5-dione;

3-(1H-indazol-1-yl)-4-(1H-indol-3-yl)-1-methyl-1H-pyrrole-2,5-dione;

3-[3-[(dimethylamino)methyl]-1H-indol-1-yl]-4-(1H-indol-3-yl)-1-methyl-1H-pyrrole-2,5-dione;

3-(1H-benzimidazol-1-yl)-4-(1H-indol-3-yl)-1H-pyrrole-2,5-dione;

3-(1H-indol-1-yl-4-(1-methyl-1H-indol-3-yl)-1H-pyrrole-2,5-dione;

3-(3,5-dimethyl-1-phenyl-1H-pyrazol-4-yl)-4-4-morpholinyl)-1H-pyrrole-2,5-dione;

3-amino-4-(1H-indol-3-yl)-1H-pyrrole-2,5-dione;

3-amino-4-(5-methoxy-1H-indol-3-yl)-1H-pyrrole-2,5-dione;

1H-Indole-1-carboxylic acid, 3-(4-amino-2,5-dihydro-1-methyl-2,5-dioxo-1H-pyrrol-3-yl)-, 1,1-dimethylethyl ester;

3-(1H-indol-3-yl)-1-methyl-4-[(phenylmethyl)amino]-1H-pyrrole-2,5-dione;

Glycine, N-[2,5-dihydro-4-(1H-indol-3-yl)-1-methyl-2,5-dioxo-1H-pyrrol-3-yl]-, ethyl ester;

3-amino-4-(1H-indol-3-yl)-1-methyl-1H-pyrrole-2,5-dione;

1-(4-methylphenyl)-3-[(4-methylphenyl)amino]-4-phenyl-1H-pyrrole-2,5-dione;

3-[[3-[(3-aminopropyl)amino]propyl]amino]-4-(1H-indol-3-yl)-1H-pyrrole-2,5-dione;

3-[[3-[4-(3-aminopropyl)-1-piperazinyl]propyl]amino]-4-(1H-indol-3-yl)-1H-pyrrole-2,5-dione;

3-(1H-indol-3-yl)-4-[[3-(4-methyl-1-piperazinyl)propyl]amino]-1H-pyrrole-2,5-dione;

1-[3-[(3-aminopropyl)amino]propyl]-3-[[3-[(3-aminopropyl)amino]propyl]amino]-4-(1H-indol-3-yl)-1H-pyrrole-2,5-dione;

1-[3-[4-(3-aminopropyl) 1-piperazinyl]propyl]-3-[[3-[4-(3-aminopropyl)-1-piperazinyl]propyl]amino]-4-(1H-indol-3-yl)-1H-pyrrole-2,5-dione;

3-(1H-indol-3-yl)-1-[3-(4-methyl-1-piperazinyl)propyl]-4-[[3-(4-methyl-1-piperazinyl)propyl]amino]-1H-pyrrole-2,5-dione;

3,3'-iminobis(3,1-propanediylimino)]bis[4-(1H-indol-3-yl)-1H-pyrrole-2,5-dione;

3,3'-[1,4-piperazinediylbis(3,1-propanediylimino)]bis[4-(1H-indol-3-yl)-1H-pyrrole-2,5-dione;

3-amino-4-(3,4-dimethoxyphenyl)-1H-pyrrole-2,5-dione;

3-[(5-aminopentyl)amino]-4-(1H-indol-3-yl)-1H-pyrrole-2,5-dione;

3-[[5-[(2-aminoethyl)amino]pentyl]amino]-4-(1H-indol-3-yl)-1H-pyrrole-2,5-dione;

3-[(2-aminoethyl)amino]-4-(1H-indol-3-yl)-1H-pyrrole-2,5-dione;

3-[(6-aminohexyl)amino]-4-(1H-indol-3-yl)-1H-pyrrole-2,5-dione;

3-[(7-aminoheptyl)amino]-4-(1H-indol-3-yl)-1H-pyrrole-2,5-dione;

3-[[2-[(2-aminoethyl)amino]ethyl]amino]-4-(1H-indol-3-yl)-1H-pyrrole-2,5-dione;

Benzenepropanamide, .alpha.-amino-N-[5-[[2,5-dihydro-4-(1H-indol-3-yl)-2,5-dioxo-1H-pyrrol-3-yl]amino]pentyl]-, (S)-;

Pentanoic acid. 4-amino-5-[[5-[[2,5-dihydro-4-(1H-indol-3-yl)-2,5-dioxo-1H-pyrrol-3-yl]amino]pentyl]amino]-5-oxo-, (S)-;

Pentanamide, 2-amino-5-[(aminoiminomethyl)amino]-N-[2-[[5-[[2,5-dihydro-4-(1H-indol-3-yl)-2,5-dioxo-1H-pyrrol-3-yl]amino]pentyl]amino]ethyl]-, (S)-;

Benzenepropanamide, .alpha.-amino-N-[2-[[5-[[2,5-dihydro-4-(1H-indol-3-yl)-2,5-dioxo-1H-pyrrol-3-yl]amino]pentyl]amino]ethyl]-, (S)-;

Butanamide, 4-[(aminoiminomethyl)amino]-N-[5-[[2,5-dihydro-4-(1H-indol-3-yl)-2,5-dioxo-1H-pyrrol-3-yl]amino]pentyl]-, (S)-;

3-(4-methylphenyl)-1-phenyl-4-(phenylamino)-1H-pyrrole-2,5-dione;

1,3-bis(4-methylphenyl)-4-((4-methylphenyl)amino]-1H-pyrrole-2,5-dione;

3-amino-1,4-diphenyl-1H-pyrrole-2,5-dione;

3-(4-methylphenyl)-4-(4-morpholinyl)-1-phenyl-1H-pyrrole-2,5-dione;

3-(4-methylphenyl)-1-phenyl-4-((phenylmethyl)amino]-1H-pyrrole-2,5-dione;

3-amino-4-(4-methylphenyl)-1-phenyl-1H-pyrrole-2,5-dione;

3-(3,5-dimethyl-1-phenyl-1H-pyrazol-4-yl)-4-(4-morpholinyl)-1H-pyrrole-2,5-dione;

3-(4-nitrophenyl)-1-phenyl-4-phenylamino-1H-pyrrole-2,5-dione;

3-amino-1-methyl-4-p-tolyl-1H-pyrrole-2,5-dione;

3-(2-diethylamino-ethylamino)-4-phenyl-pyrrole-2,5-dione;

3-[butyl-(2-diethylamino-ethyl)-amino]-4-phenyl-pyrrole-2,5-dione;

3-[benzyl-(2-dimethylamino-ethyl)-amino]-4-phenyl-pyrrole-2,5-dione;

3-[benzyl-(2-dimethylamino-ethyl)amino]-1-methyl-4-phenyl-pyrrole-2,5-dione;

3-[benzyl-(2-dimethylamino-ethyl)-amino-4-(4-chloro-phenyl)-pyrrole-2,5-dione;

3-[benzyl-(2-diethylamino-ethyl)-amino]-4-phenyl-pyrrole-2,5-dione;

3-[benzyl-(2-dimethylamino-ethyl)-amino](3-methoxy-phenyl)-pyrrole-2,5-dione;

3-(4-chloro-phenyl)-4-[2-(4-methyl-piperazin-1-yl)-ethylamino]-pyrrole-2,5-dione;

3-[2-(4-methyl-piperazin-1-yl)-ethylamino]-4-phenyl-pyrrole-2,5-dione;

3-phenyl-4-(diethylamino)pyrrole-2,5-dione;

3-phenyl-4-(benzylamino)-pyrrole-2,5-dione;

1-methyl-3-phenyl-4-(2-diethylaminoethylamino)-pyrrole-2,5-dione;

1-allyl-3-phenyl-4-(2-dimethylaminoethylatnino)-pyrrole-2,5-dione; and;

1,3-diphenyl-4-piperidino-pyrrole-2,5-dione.

It is considered that the compounds of formula (IB) are novel. Accordingly, the present invention also provides a compound of the above defined formula (IB) or a derivative thereof.

There is a subgroup of compounds falling wholly within formula (I) of formula (IC):

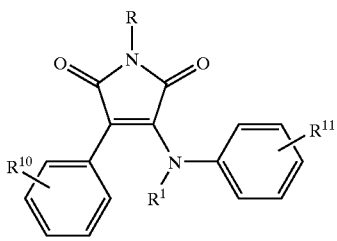

(IC)

wherein:

R and $R^1$ are as defined in relation to formula (I);

$R^{10}$ represents hydrogen or one or more substituents, suitably up to three, selected from the list consisting of: alkoxycarbonyl, alkoxyalkyl, perfluoroalkyl, perfluoroalkylS—, perfluoroalkylO—, phenyl(di-$C_{1-6}$alkoxy)C—, benzoyl, $C_{1-6}$alkylSO$_2$—, —[(CH=CH)$_2$]—, phenyl, nitro, —OCH$_2$O—, benzyloxy, phenoxy, halo, hydroxy, alkyl, alkoxy, amino, mono- or di-alkyl amino or thioalkyl;

$R^{11}$ represents hydrogen or one or more substituents, suitably up to three, selected from the list consisting of: substituted or unsubstituted $C_{1-6}$alkyl, phenyl, benzyl, substituted or unsubstituted $C_{1-6}$alkylS—, halo, hydroxy, substituted or unsubstituted $C_{1-6}$alkoxy, substituted or unsubstituted phenoxy, indolyl, naphthyl, carboxy, $C_{1-6}$alkoxycarbonyl, benzyloxy, phenoxy, pentafluorophenoxy, nitro, substituted or unsubstituted carbamoyl, substituted or unsubstituted $C_{1-6}$alkylcarbonyl, benzoyl, cyano, perfluoro$C_{1-6}$alkylSO$_2$—, $C_{1-6}$alkylNHSO$_2$—, oxazolyl, substituted or unsubstituted phenylS—, $C_{1-6}$alkylpiperazinyl-, $C_{1-6}$alkylcarbonylpiperazinyl-, 1,2,3-thiadiazolyl, pyrimidin-2-yloxy, N-[pyriidin-2-yl]-N-methylamino, phenylamino, $C_{1-6}$alkylsulphonylamino, N-morpholinylcarbonyl, cyclohexyl, adamantyl, trityl, substituted or unsubstituted $C_{1-6}$alkenyl, perfluoro$C_{1-6}$alkyl, perfluoro$C_{1-6}$alkoxy, perfluoro$C_{1-6}$akylS—, aminosulphonyl, morpholino, (di$C_{1-6}$alkyl)amino, $C_{1-6}$alkylCONH—, (di$C_{1-6}$alkoxy)phenyl(CH$_2$)$_n$NHC(O)CH(phenyl)S— where n is 1 to 6, and $C_{1-6}$alkylCON($C_{1-6}$alkyl)—, thiazolidinedionyl$C_{1-6}$alkyl, phenylCH(OH)—, substituted or unsubstituted piperazinyl$C_{1-6}$alkoxy, substituted or unsubstituted benzoylamino; or —(CH$_2$)$_x$—, —SCH=N—, —SC(C$_{1-6}$alkyl)=N—, —OCF$_2$O—, —[CH=CHC(O)O]—, —[N=CH—CH=CH]—, —CH=N—NH—, —CH=CH—NH—, —OC(NHC$_{1-6}$alkyl)=N—, —OC(O)NH—, —C(O)NMeC(O)—, —C(O)NHC(O)—, —CH$_2$)$_x$C(O)—, —N=N—NH—, —N=C(C$_{1-6}$alkyl)O—, —O(CH$_2$)$_x$O—, —(CH$_2$)$_x$SO$_2$(CH$_2$)$_y$—, and —N(C$_{1-6}$alkylcarbonyl)(CH$_2$)$_x$—, where x and y are independently 1 to 4.

There is a subgroup of compounds within formula (IC) of formula (IC') wherein R, $R^1$, $R^{10}$ and $R^{11}$ are as defined in relation to formula (IC) with the proviso that formula (IC') does not include:

3-phenylamino-4-phenyl-1H-pyrrole-2,5-dione;

1-(4-methylphenyl)-3-[(4-methylphenyl)amino]-4-phenyl-1H-pyrrole-2,5-dione;

3-(4-methylphenyl)-1-phenyly-4-phenylamino)-1H-pyrrole-2,5-dione;

1,3-bis(4-methylphenyl)-4-[(4-methylphenyl)amino]-1H-yrrole-2,5-dione, or, 3-(4-nitrophenyl)-1-phenylphenylamino-1H-pyrrole-2,5-dione.

Suitably, R is hydrogen.

Suitably, $R^1$ is hydrogen.

Suitably, $R^{10}$ represents hydrogen or one or more substituents selected from the list consisting of: halo, hydroxy, alkyl, alkylthio, alkoxy, amino or methylenedioxy. especially one or more halo and alkyl groups.

Favourably, $R^{10}$ represents hydrogen or the substituents selected from the list consisting of: 2-Br, 2-Cl, 2-F, 2-OMe, 3-Cl, 3-F, 3-Me, 3-NH$_2$, 3-OMe, 4-Br, 4-Cl, 4-I, 4-Me, 4-OH, 4-OMe, 4-SMe, 2,3-di-F, 2,5-di-F, 2,6-di-F, 3,4-di-F, 3,5-di-F, 2,3,5-tri-F, 2,4-di-Cl, 2,4-di-OMe, 3,4-(OCH$_2$O) and 3,5-di-Me.

More favourably, $R^{10}$ represents the substituents selected from the list consisting of: 2-Br, 2-Cl, 2-F, 2-OMe, 3-Cl, 3-F, 3-Me, 4-Br, 4-Cl, 4-I, 2,3-di-F, 2,5-di-F, 2,6-di-F, 3,4-di-F, 3,5-di-F, 2,3,5-tri-F, 2,4-di-Cl and 3,5-di-Me.

Preferably, $R^{10}$ represents the substituents selected from the list consisting of: 2-F, 2-OMe, 3-F, 4-Cl and 2,3-di-F.

Suitably, $R^{11}$ represents hydrogen or one or more substituents selected from the list consisting of: 2-F, 2-Me, 3-Br, 3-Cl, 3-F, 3-I, 3-OH, 3-OMe, 3-OPh, 3-SMe, 3-CO$_2$H, 3-CH$_2$CO$_2$H, 3-CH$_2$CO$_2$Me, 3-CH$_2$CONH$_2$, 3-CH$_2$CONHMe, 3-CH$_2$OH, 4-Cl, 4-F, 4-Me, 4-NHCOMe, 4-NHPh, 4-NHSO$_2$Me, 4-NMe$_2$, 4-OMe, 4-COPh, 4-SMe, 4-CH$_2$CN, 4-SO$_2$NH$_2$, 4-(CH$_2$)$_2$OH, 4-CH(OH)Ph, 4-CH$_2$SO$_2$NHMe, 4-CH$_2$CO$_2$H, 4-(CH$_2$)$_2$CO$_2$H, 4-(CH$_2$)$_2$CO$_2$Me, 4-(CH$_2$)$_2$CONH$_2$, 4-(CH$_2$)$_3$CO$_2$H, 4-(CH$_2$)$_3$CONH$_2$, 4-CH=CHCO$_2$H, 4-CH=CHCONH$_2$, 4-OCH$_2$CO$_2$H, 4-SCH$_2$CO$_2$H, 4-S-[2-CO$_2$H-Ph], 4-S-(3-CO$_2$H-Ph], 4-CH$_2$(1,3-thiazolidin-2,4-dion-5-yl), 2,3-di-F, 2,4-di-F, 3,4-di-F 3,5-di-F, 3-Cl-4-Br, 3-Cl-4-Me, 3-Br-4-Me, 3-Cl-4-OH, 3-Cl-4-OMe, 3,5-di-Me, 3,5-di-OMe, 3,4-OC(O)NH—, 3,4-OCF$_2$O—, 3,5-di-Br-4-OH, 3,5-di-Cl-4-

Me, 3,5-di-Cl-4-OH, 3-CO₂H-4-[S-(2-CO₂H)-Ph], 3-CO₂H-4-[S-(2-CONHMe)-Ph], 3-CO₂H-4-Cl, 3-F-4-Me, 3-F-4-OMe, -3,4-[(CH=N—NH)]—, -3,4-[(N=N—NH)]—, -3,4-[(NH—N=CH)]—, -3,4-[(CH₂)₃]—, -3,4-[(O(CH₂)₃O)]—, -3,4-[O—C(NHMe)=N]—, -3,4-[OCH₂O]—, -3,4-[S—C(NHMe)=N]— and -3,4-[S—CH=N]—, Favourably, R¹¹ represents hydrogen or the substituents selected from the list consisting of: 2-F, 2-Me, 3-Cl, 3-F, 3-I, 3-OMe, 3-OPh, 3-SMe, 3-CH₂CO₂H, 3-CH₂CO₂Me, 3-CH₂CONH₂, 3-CH₂CONHMe, 3-CH₂OH, 4-Cl, 4-F, 4-NHCOMe, 4-NHPh, 4-NHSO₂Me, 4-NMe₂, 4-OMe, 4-COPh, 4-SMe, 4-CH₂CN, 4-SO₂NH₂, 4-(CH₂)₂OH, 4-CH(OH)Ph, 4-CH₂SO₂NHMe, 4-CH₂CO₂H, 4-(CH₂)₂CO₂H, 4-(CH₂)₂CO₂Me, 4-(CH₂)₂CONH₂, 4-(CH₂)₃CO₂H, 4-(CH₂)₃CONH₂, 4-CH=CHCONH₂, 4-OCH₂CO₂H, 4-SCH₂CO₂H, 4-S-[2-CO₂H-Ph], 4-S-[3-CO₂H-Ph], 4-CH₂(1,3-thiazolidin-2,4-dion-5-yl 2,3-di-F, 2,4-di-F, 3,4-di-F, 3,5-di-F, 3-Cl-4-Br, 3-Cl-4-Me, 3-Br-4-Me, 3-Cl-4-OH, 3-Cl-4-OMe, 3,5-di-Me, 3,5-di-OMe, 3,4-[OC(O)NH], 3,4-[OCF₂O] 3,5-di-Cl-4-Me, 3-CO₂)H-4-[S-(2-CONHMe)Ph], 3-F-4-Me, 3-F-4-OMe, 3,4-[(CH=N—NH)], 3,4-[(N=N—NH)], 3,4-[(NH—N=CH)], 3,4-[(CH₂)₃], 3,4-[O(CH₂)₃O], 3,4-[O—C(NHMe)=N], 3,4-[OCH₂O], 3,4-[S—C(NHMe)=N] and 3,4-[S—CH=N].

More favourably, R¹¹ represents the substituents selected from the list consisting of: 3-Cl, 3-Br, 4-OMe, 3,5-di-F, 4-CH₂SO₂NHMe, 4-(CH₂)₃CO₂H and 4-S-[3-CO₂H-Ph].

A particular compound of formula (IC) is that wherein R and R¹ each represent hydrogen and R¹⁰ and R¹¹ each have the following respective values:

| R¹⁰ | R11 |
|---|---|
| 4-Cl | 3-Cl |
| 4-Cl | 3-Br |
| 2-OMe | 4-OMe |
| 4-Cl | 4-CH₂SO₂NHMe |
| 2-OMe | 3,5-di-F |
| 2-F | 3,5-di-F |
| 3-F | 4-(CH₂)₃CO₂H |
| 2,3-di-F-Ph | 3,5-di-F. |

It is considered that the compounds of formula (IC') are novel. Accordingly, the present invention also provides a compound of the above defined formula (IC') or a derivative thereof.

There is a subgroup of compounds falling wholly within formula (I) being of formula (ID):

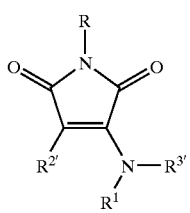

(ID)

wherein R and R¹ are as defined in relation to formula (I);
R²' is phenyl, substituted phenyl or indolyl;
R³' is hydrogen, alkyl, cycloalkyl, phenyl, substituted phenyl, C₁₋₆alkylphenyl wherein the phenyl group is optionally substituted, alkoxyalkyl, substituted or unsubstinuted heterocyclyl.
In one aspect, there is provided a compound of formula (I) as hereinbefore defined which excludes compounds of formula (ID).

There is a subgroup of compounds within formula (ID) of formula (ID') wherein R, R¹, R²' and R³' are as defined in relation to formula (ID) with the proviso that formula (ID') does not include the following compounds, hereinafter referred to as List D':

3-[2-benzo[b]thien-2-yl-3-[4-dimethylamino)-2,5-dihydro-2,5-dioxo-1H-pyrrol-3-yl]-1H-indol-1-yl]-carbamimidothioic acid, propyl ester;

3-(dimethylamino)-4-(1H-indol-3-yl)-1-methyl-1H-pyrrole-2,5-dione;

3-(1H-indol-3-yl)-1-methyl-4-(phenylamino)-1H-pyrrole-2,5-dione;

3-(1H-indol-3-yl)-1-methyl-4-[[4-trifluoromethyl)phenyl]amino]-1H-pyrrole-2,5-dione;

3-(1H-indol-3-yl)-1-methyl-4-methylamino)-1H-pyrrole-2,5-dione;

3-(6-chloro-9H-purin-9-yl)-4-(1H-indol-3-yl)-1-methyl-1H-pyrrole-2,5-dione;

3-(6-amino-9H-purin-9-yl)-4-(1H-indol-3-yl)-1-methyl-1H-pyrrole-2,5-dione;

1-acetyl-3-[2,5-dihydro-1-methyl-2,5-dioxo-4-[[4-(trifluoromethyl)phenyl]amino]-1H-pyrrol-3-yl]-1H-indole;

3-amino-4-(1H-indol-3-yl)-1H-pyrrole-2,5-dione;

3-amino-4-(5-methoxy-1H-indol-3-yl)-1H-pyrrole-2,5-dione;

1H-Indole-1-carboxylic acid, 3-(4-amino-2,5-dihydro-1-methyl-2,5-dioxo-1H-pyrrol-3-yl)-, 1,1-dimethylethyl ester;

3-(1H-indol-3-yl)-1-methyl-4-[(phenylmethyl)amino]-1H-pyrrole-2,5-dione;

Glycine, N-[2,5-dihydro-4-(1H-indol-3-yl)-1-methyl-2,5-dioxo-1H-pyrrol-3-yl]-, ethyl ester;

3-amino-4-(1H-indol-3-yl)-1-methyl-1H-pyrrole-2,5-dione;

3-[[3-[(3-aminopropyl)amino]propyl]amino]-4-(1H-indol-3-yl)-1H-pyrrole-2,5-dione;

3-[[3-[4-(3-aminopropyl)-1-piperazinyl]propyl]amino]-4-(1H-indol-3-yl)-1H-pyrrole-2,5-dione;

3-(1H-indol-3-yl)-4-[[3-(4-methyl-1-piperazinyl)propyl]amino]-1H-pyrrole-2,5-dione;

1-[3-[(3-aminopropyl)amino]propyl]-3-[[3-[(3-aminopropyl)amino]propyl]amino]-4-(1H-indol-3-yl)-1H-pyrrole-2,5-dione;

1-[3-[4-(3-aminopropyl)-1-piperazinyl]propyl]-3-[[3-[4-(3-aminopropyl)-1-piperazinyl]propyl]amino]-4-1H-indol-3-yl)-1H-pyrrole-2,5-dione;

3-(1H-indol-3-yl)-1-[3-(4-methyl-1-piperazinyl)propyl]-4-[[3-(4-methyl-1-piperazinyl)propyl]amino]-1H-pyrrole-2,5-dione;

3,3'-[iminobis(3,1-propanediylimino)]bis[4-(1H-indol-3-yl)-1H-pyrrole-2,5-dione;

3,3'-[1,4-piperazinediylbis(3,1-propanediylimino)]bis[4-(1H-indol-3-yl)-1H-pyrrole-2,5-dione;

3-amino-4-(3,4-dimethoxyphenyl)-1H-pyrrole-2,5-dione;

3-[(5-aminopentyl)amino-4-(1H-indol-3-yl)-1H-pyrrole-2,5-dione;

3-[[5-[(2-aminoethyl)amino]pentyl]amino]-4-(1H-indol-3-yl)-1H-pyrrole-2,5-dione;

3-[(2-aminoethyl)amino]-4-(1H-indol-3-yl)-1H-pyrrole-2,5-dione;

3-[(6-aminohexyl)amino]-4-(1H-indol-3-yl)-1H-pyrrole-2,5-dione;

3-[(7-aminoheptyl)amino]-4-(1H-indol-3-yl)-1H-pyrrole-2,5-dione;

3-[[2-[(2-aminoethyl)amino]ethyl]amino]-4-(1H-indol-3-yl)-1H-pyrrole-2,5-dione;

Benzenepropanamide, .alpha.-amino-N-[5-[[2,5-dihydro-4-(1H-indol-3-yl)-2,5-dioxo-1H-pyrrol-3-yl]amino]pentyl]-, (S)-;

Pentanoic acid, 4-amino-5-[[5-[[2,5-dihydro-4-(1H-indol-3-yl)-2,5-dioxo-1H-pyrrol-3-yl]amino]pentyl]amino]-5-oxo-, (S)-;

Pentanamide, 2-amino-5-[(aminoiminomethyl)amino]-N-[2-[[5-[(2,5-dihydro-4-(1H-indol-3-yl)-2,5-dioxo-1H-pyrrol-3-yl]amino]pentyl]amino]ethyl]-, (S)-;

Benzenepropanamide, .alpha.-amino-N-[2-[[5-[[2,5-dihydro-4-(1H-indol-3-yl)-2,5-dioxo-1H-pyrrol-3-yl]amino]pentyl]amino]ethyl]-, (S)-;

Butanamide, 4-[(aminoiminomethyl)amino]-N-[5-[[2,5-dihydro-4-(1H-indol-3-yl)-2,5-dioxo-1H-pyrrol-3-yl]amino]pentyl]-, (S)-;

3-amino-1,4-diphenyl-1H-pyrrole-2,5-dione;

3-(4-methylphenyl)-1-phenyl-4-[(phenylmethyl)amino]-1H-pyrrole-2,5-dione;

3-amino-4-(4-methylphenyl)-1-phenyl-1H-pyrrole-2,5-dione;

3-amino-1-methyl-4-p-tolyl-1H-pyrrole-2,5-dione;

3-(2-diethylamino-ethylamino)-4-phenyl-pyrrole-2,5-dione;

3-[butyl-(2-diethylamino-ethyl)-amino]-4-phenyl-pyrrole-2,5-dione;

3-[benzyl-(2-dimethylamino-ethyl)-amino]-4-phenyl-pyrrole-2,5-dione;

3-[benzyl-(2-dimethylamino-ethyl)-amino]-1-methyl-4-phenyl-pyrrole-2,5-dione;

3-[benzyl-(2-dimethylamino-ethyl)-amino]-4-(4-chloro-phenyl)-pyrrole-2,5-dione;

3-[benzyl-(2-diethylamino-ethyl)-amino]-4-phenyl-pyrrole-2,5-dione;

3-[benzyl-(2-dimethylamino-ethyl)-amino]-4-(3-methoxy-phenyl)-pyrrole-2,5-dione;

3-(4-chloro-phenyl)-4-[2-(4-methyl-piperazin-1-yl)-ethylamino]-pyrrole-2,5-dione;

3-[2-(4-methyl-piperazin-1-yl)-ethylamino]-4-phenyl-pyrrole-2,5-dione;

3-phenyl-4-(diethylamino)-pyrrole-2,5-dione;

3-phenyl-4-(benzylamino)-pyrrole-2,5-dione;

1-methyl-3-phenyl-4-(2-diethylaminoethylamino)-pyrrole-2,5-dione, and;

1-allyl-3-phenyl-4-(2-dimethylaminoethylainino)-pyrrole-2,5-dione.

Suitably R$^{2'}$ is indolyl, phenyl or phenyl substituted with one or more, suitably up to three, substituents selected from the list consisting of: halo, haloalkyl, alkoxy, nitro, alkyl and alkoxy.

Examples of R$^{2'}$ include phenyl, indol-3-yl, 2-methoxyphenyl, 3-fluorophenyl, 3-nitrophenyl, 4-chlorophenyl, 4-iodophenyl, 4-(trifluoromethyl)phenyl and 2,3-difluorophenyl.

Suitably R$^{3'}$ represents hydrogen, C$_{1-6}$alkyl, cyclohexyl, phenyl, fluorenyl, C$_{1-2}$alkylphenyl, C$_{1-6}$alkoxyC$_{1-2}$alkyl or a substituted or unsubstituted single or a single or fused ring heterocyclyl group having 5 or 6 ring atoms and up to 3 hetero atoms in each ring, such as oxazolyl, benzofuranyl, dibenzofuranyl, pyridinyl, quinolinyl, pyrimidinyl.

Examples of R$^{3'}$ include hydrogen, ethyl, cyclohexyl, phenyl, fluoren-2-yl, benzyl, phenyl(CH$_2$)$_2$—, MeO(CH$_2$)$_2$—, 4-methyloxazol-2-yl, 2-acetylbenzofuran-5-yl, dibenzofuran-2-yl, dibenzofuran-3-yl, 2-methylpyridin-3-yl, 2,6-dimethylpyridin-3-yl, 2-chloropyridin-5-yl, quinolin-3-yl, pyrimidin-2-yl.

It is considered that the compounds of formula (ID') are novel. Accordingly, the present invention also provides a compound of the above defined formula (ID') or a derivative thereof.

There is a subgroup of compounds falling wholly within formula (I) being of formula (IE):

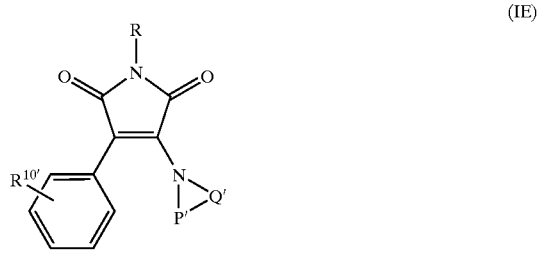

(IE)

wherein R is as defined in relation to formula (I);

R$^{10'}$ represents hydrogen or one or more, suitably up to three, substituents selected from the list consisting of: alkoxy, halo, and nitro; P'—Q' represents —(CH$_2$)$_a$O(CH$_2$)$_b$—, —(CH$_2$)$_a$S(CH$_2$)$_b$—, —(CH$_2$)$_c$—, —(CH$_2$)$_d$ CH(G)(CH$_2$)$_e$—, —(CH$_2$)$_a$N(ZZ)(CH$_2$)$_b$—, where a, b, d, and e are independently 1 to 4, c is 1 to 6, ZZ is hydrogen, alkyl, aryl, or alkylcarbonyl, and G is alkyl, amido, hydroxyalkyl, aralkyl, or hydroxy.

There is a subgroup of compounds within formula (IE) of formula (IE') wvherein R, R$^{10'}$, and P'—Q' are as defined in relation to formula (IE) with the proviso that formula (IE') does not include:

3-phenyl-4-piperidin-1-yl-pyrrole-2,5-dione;

3-(4-methylpiperazin-1-yl)-4-phenyl-pyrrole-2,5-dione;

3-(4-ethylpiperazin-1-yl)-4-phenyl-pyrrole-2,5-dione;

3-(4-chlorophenyl)-4-(4-methyl-piperazin-1-yl)-pyrrole-2,5-dione;

3-(4-methylphenyl)-4-(4-morpholinyl)-1-phenyl-1H-pyrrole-2,5-dione;

3-phenyl-4-(4-methylpiperazino)-pyrrole-2,5-dione;

3-phenyl-4-(4-phenylpiperazino)-pyrrole-2,5-dione;

1-methyl-3-phenyl-4-(4-phenylpiperazino)pyrrole-2,5-dione;

1-ethyl-3-phenyl-4-(4-chlorophenylpiperazino)-pyrrole-2,5-dione;

1-allyl-3-phenyl-4-(4-methylpiperazino)-pyrrole-2,5-dione, and;

1,3-diphenyl-4-piperidino-pyrrole-2,5-dione.

Suitably, R$^{10'}$ is methoxy, chloro, or nitro.

Examples of R$^{10'}$ include 4-methoxy, 4-chloro, 2,4-dichloro, and 3-nitro.

Examples of —P'—Q'— include —(CH$_2$)$_4$—, —(CH$_2$)$_2$O(CH$_2$)$_2$—, —(CH$_2$)$_3$CH(Me)CH$_2$—, —(CH$_2$)$_3$CH(CONH$_2$)CH$_2$—, —(CH$_2$)$_3$CH(CH$_2$OH)CH$_2$—, —(CH$_2$)$_2$CH(CH$_2$Ph)(CH$_2$)$_2$—, —(CH)$_2$CH(OH)(CH$_2$)$_2$—, —(CH$_2$)$_5$—, and —(CH$_2$)S(CH$_2$)$_2$—.

It is considered that the compounds of formula (IE' are novel. Accordingly, the present invention also provides a compound of the above defined formula (IE') or a derivative thereof.

There is a subgroup of compounds falling wholly within formula (I) being of formula (IF):

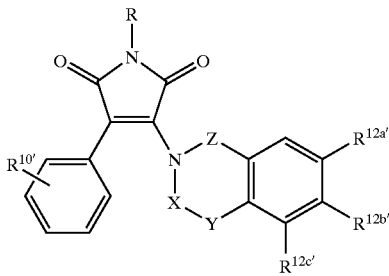

(IF)

wherein R is as defined in relation to formula (I);

R10" is one or more, suitably up to three, substituents selected from the list consisting of perfluoroalkyl, halo, nitro, alkoxy, arylcarbonyl, alkyl;

Z is a bond or an alkylene chain;

—X—Y— is —CH=N, —(CH$_2$)$_t$—, —(CH$_2$)$_u$CH(U)—, —(U)CH(CH$_2$)$_u$—, —CH=CH—, —(CH$_2$)$_v$C(alkyl)$_2$—, —C(O)C(alkyl)$_2$—, —C(O)O—, where t, u, and v are independently 1 to 4, and U is alkyl, carboxy, alkoxycarbonyl, hydroxyalkyl, and amido;

$R^{12a'}$, $R^{12b'}$, and $R^{12c'}$ are each independently hydrogen, nitro, alkoxy, 4-ethylpiperazin-1-yl, 4-BOC-piperazin-1-yl, 4-methyl-piperazin-1-yl, 4-methyl-piperazin-1-yl, halo, alkyl, piperazin-1-yl, perfluoroalkyl, and alkylsulphonylamino.

Suitably, Z is a bond or a $C_{1-2}$alkylene chain.

Examples of Z include a bond, methylene or ethylene.

Examples of —X—Y— are —CH=N—, —(CH$_2$)$_2$—, —CH(Me)CH$_2$—, —CH=CH—, —CH(CO$_2$H)CH$_2$—, —CH(CO$_2$Me)CH$_2$—, —(CH$_2$)$_3$—, —CH(CH$_2$OH)CH$_2$—, —CH$_2$CH(CH$_2$OH)—, —CH$_2$CH(Me)—, —CH$_2$C(Me)$_2$—, —CH(CONH$_2$)CH$_2$—, —C(O)C(MeC—, and —C(O)O—.

Examples of $R^{12a'}$, $R^{12b'}$, and $R^{12c'}$ include hydrogen, nitro, fluoro, methoxy, 4-ethylpiperazin-1-yl, 4-BOC-piperazin-1-yl, 4-methyl-piperazin-1-yl, 4-methyl-piperazin-1-yl, chloro, bromo, trifluoromethyl, and methanesulphonylamino.

Preferably, Z is a bond.

Preferably, —X—Y— is —(CH$_2$)$_2$— or —CH(CH$_2$OH)CH$_2$—, —CH(Me)CH$_2$—, —CH$_2$CH(Me)—, or —CH$_2$C(Me)$_2$—.

Preferably, $R^{12b'}$ is fluorine.

Preferably, $R^{12a'}$ is fluorine.

Most preferably, $R^{10"}$ is 2-Br, 2-Cl, 2-F, 2OMe, 3-Cl, 3-F, 3-Me, 4Br, 4-Cl, 4-I, 2,3-di-F, 2,5-di-F, 2,6-di-F, 3,4-di-F, 3,5-di-F, 2,3,5-tri-F, 2,4-di-Cl, 3,5-di-Me;

Z is a bond:

—X—Y— is —(CH$_2$)$_2$— or —CH(CH$_2$OH)CH$_2$—, —CH(Me)CH$_2$—, —CH$_2$CH(Me)—, or —CH$_2$C(Me)$_2$—, $R^{12b'}$ is fluorine; and $R^{12a'}$ is fluorine.

It is considered that the compounds of formula (IF) are novel. Accordingly, the present invention also provides a compound of the above defined formula (IF) or a derivative thereof. There isa subgroup of compounds falling wholly within formula (I) being of formula (IG):

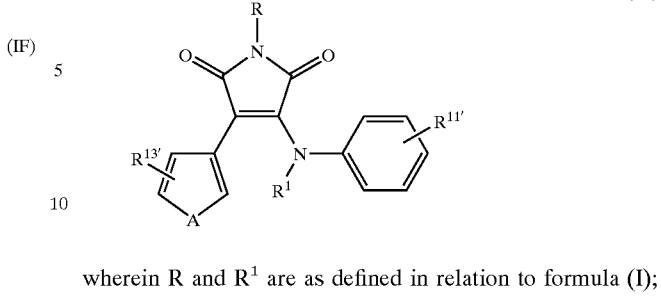

(IG)

wherein R and $R^1$ are as defined in relation to formula (I);

A is N(alkyl), oxygen, or sulphur.

Examples of A are N(methyl), oxygen, and sulphur.

Preferably, A is sulphur.

$R^{11"}$ is one or more, suitably up to three, substituents selected from the group consisting of hydrogen, halo, alkyl, alkylthio, —S—CH=N—, phenoxy, —(CH$_2$)$_w$—, hydroxy, carboxy, —O(CH)$_x$O—, hydroxyalkyl, and alkylaminosulphonylalkyl, where w and x are independently 1 to 4.

Examples of $R^{11"}$ are hydrogen, bromo, methyl, methylthio, chloro, —S—CH=N—, phenoxy, —(CH$_2$)$_3$—, hydroxy, carboxy, —O(CH$_2$)O—, fluoro, hydroxymethyl, and MeNHSO$_2$CH$_2$—.

Preferably, $R^{11"}$ is 3-Br, 4-Me, 4-SMe, 3-Br-4-Me, 3-Cl, 3,4-[S—CH=N]—, 3-OPh, 3,4-[(CH$_2$)$_3$ ]—, 3-SMe, hydrogen, 3,5-diBr-4-OH, 3,5-diCl-4-OH, 3-CO$_2$H-4-Cl, 3,4-[-OCH$_2$O]—, 3-Cl-4-OH, 3,5-diF, 3-CH$_2$OH, 3-OH, or 4-CH$_2$SO$_2$NHMe.

$R^{13'}$ is one or more, suitably up to two, substituents selected from the group consisting of —CH=CH)$_2$— and hydrogen.

Examples of $R^{13'}$ include 4,5-[(CH=CH)$_2$]— and hydrogen.

Preferably, $R^{13'}$ is hydrogen.

It is considered that the compounds of formula (IG) are novel. Accordingly, the present invention also provides a compound of the above defined formula (IG) or a derivative thereof.

There is a subgroup of compounds falling wholly within formula (I) being of formula (IH):

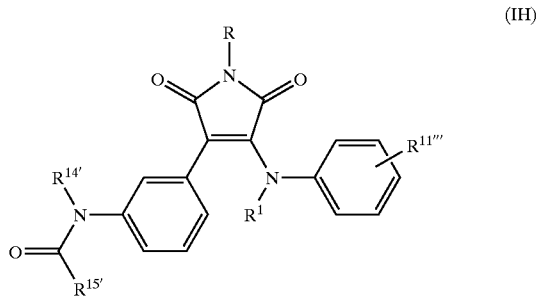

(IH)

wherein R and $R^1$ are as defined in relation to formula (I);

$R^{11'''}$ is —[(CH$_2$)$_{aa}$]—, where aa is 1 to 4;

$R^{14'}$ is hydrogen;

$R^{15'}$ is alkyl, unsubstituted or substituted phenylamino, unsubstituted or substituted phenylalkylamino, cyclohexylamino, alkenylamino, phenyl, benzyl, styryl, or alkylamino.

Examples of $R^{11'''}$ include 3,4-[(CH$_2$)$_3$].

Suitably, $R^{15'}$ is $C_{1-6}$alkyl, (halophenyl)amino, phenylalkylamino. cyclohexylamino, propenylaminio, phenyl, benzyl, styryl, propyl, ethylamino, or (methoxyphenyl)amino.

Examples of $R^{15'}$ include methyl, (3-fluorophenyl)amino, phenylethylamino, cyclohexylamino, propenylamino, phenyl, benzyl, trans-styryl, n-propyl, ethylamino, and (3-methoxyphenyl)amino.

It is considered that the compounds of formula (IH) are novel. Accordingly, the present invention also provides a compound of the above defined formula (IH) or a derivative thereof.

There is a subgroup of compounds falling wholly within formula (I) being of formula (IJ):

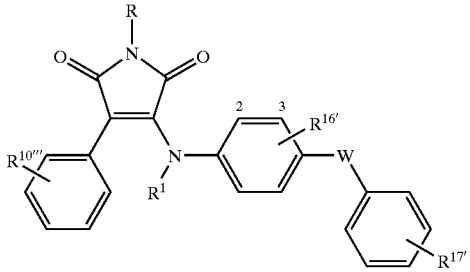

(IJ)

wherein R and $R^1$ are as defuned in relation to formula (I);

$R^{10'''}$ represents one or more, suitably up to three, substituents independently selected from alkoxy or halo;

$R^{16'}$ represents one or more, suitably up to three, substituents independently selected from hydrogen, carboxy, alkoxycarbonyl, or alkylaminocarbonyl;

$R^{17'}$ represents one or more, suitably up to three, substituents independently selected from carboxy, alkoxycarbonyl, halo, alkylaminocarbonyl, nitro, or hydrogen;

W is sulphur, oxygen, or substituted or unsubstituted NH.

Suitably, W is sulphur or oxygen. Favourably, W is sulphur.

Suitably, $R^{10'''}$ is $C_{1-6}$alkoxy, chloro, or fluoro.

Examples of $R^{10'''}$ are methoxy, 4-chloro, 2-chloro, and 2,3-difluoro.

Favourably, $R^{10'''}$ is 2,3-difluoro.

Suitably, $R^{16'}$ is hydrogen, carboxy, $C_{1-6}$alkoxycarbonyl, or $C_{1-6}$alkylaminocarbonyl.

Examples of $R^{16'}$ are carboxy, hydrogen, ethoxycarbonyl, methoxycarbonyl, and methylaminocarbonyl.

Favourably, $R^{16'}$ is hydrogen

Suitably, $R^{17'}$ is carboxy, $C_{1-6}$alkoxycarbonyl, halo, $C_{1-6}$alkylaminocarbonyl, nitro, or hydrogen;

Examples of $R^{17'}$ are 2-carboxy, 3-carboxy, 4-carboxy, 4-chloro, 2-methylaminocarbonyl, 4-nitro, hydrogen, and 2-ethoxycarbonyl.

Favourably, $R^{17'}$ is 3-carboxy.

It is considered that the compounds of formula (IJ) are novel. Accordingly, the present invention also provides a compound of the above defined formula (II) or a derivative thereof.

There is a subgroup of compounds falling wholly within formula (I) being of formula (IK):

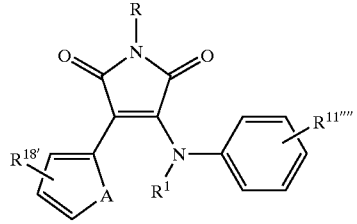

(IK)

wherein R and $R^1$ are as defined in relation to formula (I);

$R^{11''''}$ represents one or more, suitably up to three, substituents independently selected from halo and hydroxy;

$R^{18'}$ represents one or more, suitably up to three, substituents independently selected from hydrogen, alkyl, and —CH=CH)$_2$—;

A is sulphur.

Suitably, $R^{11''''}$ is chloro or hydroxy.

Examples of $R^{11\ ''''}$ are 3-chloro and 3,5-chloro-4-hydroxy.

Suitably, $R^{18'}$ is hydrogen, $C_{1-6}$alkyl, or —(CH=CH)$_2$—,

Examples of $R^{18'}$ include hydrogen, methyl, and 3-methyl-4,5-[(CH=CH)$_2$]—, It is considered that the compounds of formula (IK) are novel. Accordingly, the present invention also provides a compound of the above defined formula (IK) or a derivative thereof.

There is a subgroup of compounds falling wholly within formula (I) being of formula (IL):

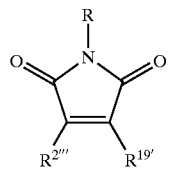

(IL)

wherein R is as defined in relation to formula (I);

$R^{2'''}$ is unsubstituted or substituted heterocyclyl or unsubstituted or substituted aryl;

$R^{19'}$ is unsubstituted or substituted heterocyclyl, or a quaternised salt thereof.

There is a subgroup of compounds within formula (IL) of formula (IL') wherein R, $R^{2'''}$, and $R^{19'}$ are as defined in relation to formula (IL) with the proviso that (IL') does not include the following compounds, hereinafter referred to as List L':

3-indol-1-yl-4-(1-methyl-1H-indol-3-yl)-pyrrole-2,5-dione;

1-(1-methyl-2,5-dioxo-4-phenylamino-2,5-dihydro-1H-pyrrol-3-yl)-pyridinium chloride;

1-1-(4-methyl-pentyl)-2,5-dioxo-4-phenylamino-2,5-dihydro-1H-pyrrol-3-yl)-pyridinium chloride;

1-(1-dodecyl-2,5-dioxo-4-phenylamino-2,5-dihydro-1H-pyrrol-3-yl)-pyridinium chloride;

3-[2,5-dihydro-4-(1H-imidazol-1-yl)-1-methyl-2,5-dioxo-1H-pyrrol-3-yl]-1H-indole-1-carboxylic acid, 1,1-dimethylethyl ester;

3-(1H-imidazo[4,5-b]pyridin-1-yl)-4-(1H-indol-3-yl)-1-methyl-1H-pyrrole-2,5-dione;

3-(1H-indol-3-yl)-1-methyl-4-(1H-pyrrolo[2,3-b]pyridin-1-yl)-1H-pyrrole-2,5-dione;

3-(1H-indol-3-yl)-1-methyl-4-(1-piperidinyl)-1H-pyrrole-2,5-dione;

3-[4-(diphenylmethyl)-1-piperazinyl]-4-(1H-indol-3-yl)-1-methyl-1H-pyrrole-2,5-dione;

3-(1H-benzimidazol-1-yl)-4-(1H-indol-3-yl)-1-methyl-1H-pyrrole-2,5-dione;

3-(1H-benzotriazol-1-yl)-4-(1H-indol-3-yl)-1-methyl-1H-pyrrole-2,5-dione;

3-(1H-imidazol-1-yl)-4-(1H-indol-3-yl)-1-methyl-1H-pyrrole-2,5-dione;

3-(1H-indol-1-yl)-4-(1H-indol-3-yl)-1-methyl-1H-pyrrole-2,5-dione;

3-(1H-indazol-1-yl)-4-(1H-indol-3-yl)-1-methyl-1H-pyrrole-2,5-dione;

3-[3-[(dimethylamino)methyl]-1H-indol-1-yl]-4-(1H-indol-3-yl)-1-methyl-1H-pyrrole-2,5-dione;

3-(1H-benzimidazol-1-yl)-4-(1H-indol-3-yl)-1H-pyrrole-2,5odone;

3-(1H-indol-1-yl)-4-(1-methyl-1H-indol-3-yl)-1H-pyrrole-2,5-dione, and;

3-(3,5-dimethyl-1-phenyl-1H-pyrazol-4-yl)-4-(4-morpholinyl)-1H-pyrrole-2,5-dione.

Suitably, $R^{2'''}$ is thienyl, phenyl, or phenyl substituted with one or more halogen groups.

Examples of $R^{2'''}$ include phenyl, 3-thienyl, 2-thienyl, 4-chlorophenyl, and 2,4-dichlorophenyl.

Favourably, $R^{2'''}$ is phenyl, 3-thienyl, 4-chlorophenyl, or 2,4-dichlorophenyl.

Suitably, $R^{19'}$ is indolinyl, pyridinium halide, azabicyclooctanyl, or triazaspirodecanonyl.

Examples of $R^{19'}$ include indolin-1-yl, 3-amino-1-pyridinium chloride, 2-methylindolin-1-yl, 1,3,3-trimethyl-6-azabicyclo[3,2,1]octan-6-yl, and 1-phenyl-1,3,8-triazaspiro-[4,5]-decan-4-one-8-yl.

Favourably, $R^{19'}$ is indolin-1-yl, or 2-methylindolin-1-yl.

It is considered that the compounds of formula (IL') are novel. Accordingly, the present invention also provides a compound of the above defined formula (IL') or a derivative thereof.

Certain of the compounds of formula (I) may contain at least one chiral carbon, and hence they may exist in one or more stereoisomeric forms. The present invention encompasses all of the isomeric forms of the compounds of formula (I) whether as individual isomers or as mixtures of isomers, including racemates.

Alkyl groups referred to herein, including those forming part of other groups, include straight or branched chain alkyl groups containing up to six carbon atoms, said carbon atoms being optionally substituted with up to five, suitably up to three, groups selected from the list consisting of aryl, heterocyclyl, alkylthio, alkenylthio, alkynylthio. arylthio, heterocyclylthio, alkoxy, arylalkoxy, arylalkylthio, amino, mono- or di-alkylamino, cycloalkyl, cycloalkenyl, carboxy and esters thereof, phosphonic acid and esters thereof, mono- or dialkylaminosulphonyl, aminosulphonyl, cyano, alkylcarbonylamino, arylcarbonylamino, hydroxy, and halogen.

Alkenyl and alkynyl groups referred to herein include straight and branched chain alkenyl groups containing from two to six carbon atoms, said carbon atoms being optionally substituted with up to five, suitably up to three, groups including those substituents described hereinbefore for the alkyl group. Cycloalkyl and cycloalkenyl groups referred to herein include groups having between three and eight ring carbon atoms, which carbon atoms are optionally substituted with up to five, suitably up to three, groups including those substituents described hereinbefore for the alkyl group.

When used herein the term "aryl" includes phenyl and biphenyl groups, for example naphthyl, especially phenyl.

Suitably optional substituents for any aryl group include up to three substituents selected from the list consisting of halo, alkyl, alkenyl, substituted alkenyl arylalkyl alkoxy, alkoxyalkyl, haloalkyl, haloalkyloxy, hydroxy, hydroxyalkyl, nitro, amino, cyano, cyanoalkyl, mono- and di-N-alkylamino, acyl, acylamino, N-alkylacylamino, acyloxy, carboxy, carboxyalkyl, carboxyalkylcarbonyl, carboxyalkenyl, ketoalkylester, carbamoyl, carbamoylalkyl, mono- and di-N-alkylcarbamoyl, alkoxycarbonyl, alkoxycarbonylalkyl, aryloxy, arylthio, aralkyloxy, aryloxycarbonyl, ureido, guanidino, morpholino, adamantyl, oxazolyl, aminosulphonyl, aikylaminosulphonyl, alkylthio, haloalkylthio, alkylsulphinyl, alkylsulphonyl, cycloalkyl, heterocyclyl, heterocyclylalkyl, trityl, substituted trityl, mono- or bis-alkylphosphonate or mono- or bis-alkylphosphonate$C_{1-6}$alkyl or any two adjacent substituents on the phenyl ring together with the carbon atoms to which they are attached form a carbocyclic ring or a heterocyclic ring.

When used herein the terms "heterocyclyl" and "heterocyclic" suitably include. unless otherwise defined, aromatic and non-aromatic, single and fused, rings suitably containing up to four heteroatoms in each ring, each of which is selected from oxygen, nitrogen and sulphur, which rings, may be unsubstituted or substituted by, for example, up to three substituents. Each ring suitably has from 4 to 7, preferably 5 or 6, ring atoms. A fused heterocyclic ring system may include carbocyclic rings and need include only one heterocyclic ring.

Substituents for any heterocyclyl or heterocyclic group are suitably selected from halogen, alkyl, arylalkyl, alkoxy, alkoxyalkyl, haloalkyl, hydroxy, amino, mono- and di-N-alkyl-amino, acylamino, carboxy salts, carboxy esters, carbamoyl, mono- and di-N-alkylcarbonyl, aryloxycarbonyl, alkoxycarbonylalkyl, aryl, oxy groups, ureido, guanidino, sulphonylamino, aminosulphonyl, alkylthio, alkylsulphinyl, alkylsulphonyl, heterocyclyl and heterocyclylalkyl.

When used herein 'halo' includes iodo, bromo, chloro or fluoro, especially chloro or fluoro.

Suitable derivatives of the compounds of the invention are pharmaceutically acceptable derivatives.

Suitable derivatives of the compounds of the invention include salts and solvates.

Suitable pharmaceutically acceptable derivatives include pharmaceutically acceptable salts and pharmaceutically acceptable solvates.

Suitable pharmaceutically acceptable salts include metal salts, such as for example aluminium, alkali metal salts such as lithium, sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)amine or tri-(2-hydroxyethyl)-amine, cycloalkylamines such as bicyclohexylamine, or with procaine, dibenzylpiperidine, N-benzyl-β-phenethylamine, dehydroabietylamine. N,N'-bisdehydroabietylamnine, glucamine. N-methylglucamnine or bases of the pyridine type such as pyridine, collidine, quinine or quinoline.

Suitable pharrnaceutically acceptable salts also includes pharmaceutically acceptable acid addition salts, such as those provided by pharmaceutically acceptable inorganic acids or organic acids.

Suitable pharmaceutically acceptable acid addition salts provided by pharmaceutically acceptable inorganic acids includes the sulphate, nitrate, phosphate, borate, hydrochloride and hydrobromide and hydroiodide.

Suitable pharmaceutically acceptable acid addition salts provided by pharmaceutically acceptable organic acids includes the acetate, tartrate, maleate. fumarate, malonate, citrate, succinate, lactate, oxalate, benzoate, ascorbate, methanesulphonate, α-keto glutarate and α-glycerophosphate.

Suitable pharmaceutically acceptable solvates include hydrates.

For the avoidance of doubt when used herein the term "diabetes" includes diabetes mellitus, especially Type 2-diabetes, and conditions associated with diabetes mellitus.

The term 'conditions associated with diabetes' includes those conditions associated with the pre-diabetic state, conditions associated with diabetes mellitus itself and complications associated with diabetes mellitus.

The term 'conditions associated with the pre-diabetic state' includes conditions such as insulin resistance, impaired glucose tolerance and hyperinsulinaemia The term 'conditions associated with diabetes mellitus itself' include hyperglycaemia insulin resistance and obesity. Further conditions associated with diabetes mellitus itself include hypertension and cardiovascular disease, especially atherosclerosis and conditions associated with insulin resistance. Conditions associated with insulin resistance include polycystic ovarian syndrome and steroid induced insulin resistance.

The term 'complications associated with diabetes mellitus' includes renal disease, especially renal disease associated with Type II diabetes, neuropathy and retinopathy. glomerular sclerosis, nephrotic syndrome, hypertensive nephrosclerosis and end stage renal disease.

A further aspect of the invention provides a process for the preparation of a compound of the invention, which process comprises reaction of a compound of formula (II):

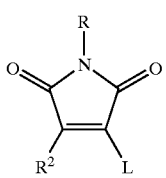

(II)

wherein R and $R^2$ are as defined in formula (D and L is a leaving group, with a compound of formula (III):

(III)

wherein $R^1$ and $R^3$ are as defined in formula (I); and thereafter, if required, carrying out one or more of the following optional steps:
 (i) converting a compound of formula (I) to a further compound of formula (I);
 (ii) removing any necessary protecting group;
 (iii) preparing an appropriate derivative of the compound so formed.

Examples of suitable leaving groups, L, are chloro, bromo, triflate, and hydroxy.

The reaction between the compounds of formulae (II) and (III) is carried out in any suitable solvent, for example 1-methyl-2-pyrrolidinone, tetrahydrofuran, 0.880 ammonia, or methanol, under conventional amination conditions at any temperature providing a suitable rate of formation of the required product, generally an elevated temperature, over a suitable reaction time.

Suitable reaction temperatures include those in the range of 60° C. to 220° C. and, as appropriate, the reflux temperature of the solvent. When the compound of formula (III) is a weak nucleophile, then the reaction may be assisted by, for example, using temperatures at the upper end of this range, generating the anion of the compound of formula (III) in situ using, for example, sodium hydride, or by using a basic catalyst such as triethylamine. Conventional methods of heating also include the use of microwave heating devices, for example a microwave reactor, such as a 100 watt reactor.

The reaction products are isolated using conventional methods. Typically, the reaction mixture is cooled, the residue acidified and the products extracted using solvent extraction, suitably using an organic solvent.

The reaction products are purified by conventional methods, such as chromatography and trituration.

Crystalline product may be obtained by standard methods.

Crystalline product may be obtained by standard methods. In a preferred aspect, a solution of the compound of formula (II) and a compound of formula (III) in methanol is heated to reflux from between 1 to 4 days, then cooled and concentrated. The residue is then acidified with hydrochloric acid, and extracted with ethyl acetate. The organic extracts are then washed with water, brine, dried with anhydrous magnesium sulphate, and the solvent is removed. The product is then purified by standard methods such as trituratlon or chromatography, on silica gel, to afford the desired compound.

The above mentioned conversion of a compound of formula (I) into another compound of formula (I) includes any conversion which may be effected using conventional procedures, but in particular the said conversions include any combination of:
 (i) converting one group R into another group R;
 (ii) converting one group $R^3$ into another group $R^3$;
 (iii) converting one group $R^{10}$ into another group $R^{10}$, and;
 (iv) converting one group $R^{11}$ into another group $R^{11}$.

The above mentioned conversions (i) to (iv) may be carried out using any appropriate method under conditions determined by the particular groups chosen.

Thus, suitable conversions of one group R into another group R, as in conversion (i), include:
 (a) converting a group R which represents hydrogen into a group R which represents an alkyl or arylalkyl group; such conversion may be carried out using an appropriate conventional alkylation procedure, for example treating an appropriately protected compound of formula (I) with an alkylating agent; and
 (b) converting a group R which represents an alkyl group into a group R where R represents hydrogen; such conversion may be carried out using an appropriate dealkylation procedure, for example treating an appropriately protected compound of formula (I) with aqueous base followed by ammrnonium hydroxide.

Suitable conversions of one group $NR^1R^3$ into another group $NR^1R^3$, as in conversion (ii), include:
 converting a group $NR^1R^3$ which represents arylamino into another group $NR^1R^3$ which represents alkylamino: such conversion may be carried out using an appropriate conventional procedure, for example treating an appropriately protected compound of formula (I) with an alkylamine.

Suitable conversions of one group $R^{10}$ into another group $R^{10}$, as in conversion (iii), include:

(a) converting a group $R^{10}$ which represents nitro into a group $R^{10}$ which represents amino, such conversion may be carried out using a conventional reduction procedure, for example hydrogenating an appropriately protected compound of formula (I);

(b) converting a group $R^{10}$ which represents nitro into a group $R^{10}$ which represents acetylamino, such conversion may be carried out using an appropriate conventional reductive acylation procedure, for example hydrogenating an appropriately protected compound of formula (I) followed by acylation of the resultant amino group with an acylating agent;

(c) converting a group $R^{10}$ which represents amino into a group $R^{10}$ which represents a substituted urea, such conversion may be carried out using an appropriate conventional amidation procedure, for example treating an appropriately protected compound of formula (I) with an appropriately substituted isocyanate;

(d) converting a group $R^{10}$ which represents amino into a group $R^{10}$ which represents acylamino, such conversion may be carried out using an appropriate conventional acylation procedure, for example treating an appropriately protected compound of formula (I) with an acylating agent or treating an appropriately protected compound of formula (I) with a suitable carboxylic acid in the presence of activating agents such as a mixture of 1-hydroxybenrotriazole and 1-(3-dimethylaminopropyl)-3-ethylcarbodiimide, and;

(e) converting a group $R^{10}$ which represents iodo into a group $R^{10}$ which represents alkoxycarbonyl, such conversion may be carried out using an appropriate procedure, for example treating an appropriately protected compound of formula (I) with carbon monoxide and methanol in the presence of a palladium(0) complex.

Suitable conversions of one group $R^{11}$ into another group $R^{11}$, as in conversion (iv), include:

(a) converting a group $R^{11}$ which represents a t-BOC-protected amino group into a group $R^{11}$ which represents amino, such conversion may be carried out using an appropriate conventional deprotection procedure, for example deprotecting a t-BOC-protected compound of formula (I) with trifluoroacetic acid;

(b) converting a group $R^{11}$ which represents a carboxylic acid group into a group $R^{11}$ which represents an amide group, such conversion may be carried out using an appropriate conventional procedure, for example treating an appropriately protected compound of formula (I) with an amine in the presence of suitable activating agents such as a mixture of 1-hydroxybenzotriazole and 1-(3-dimethylaminopropyl)-3-ethylcarbodiimide: and (c) converting a group $R^{11}$ which represents alkoxycarbonyl into a group $R^{11}$ which represents carbamoyl, such conversion may be carried out using an appropriate conventional procedure, for example treating an appropriately protected compound of formula (I) with methanolic ammonia solution followed by aqueous ammonia.

The above mentioned conversions may as appropriate be carried out on any of the intermediate compounds mentioned herein.

Suitable protecting groups in any of the above mentioned reactions are those used conventionally in the art The methods of formation and removal of such protecting groups are those conventional methods appropriate to the molecule being protected. Thus for example a benzyloxy group may be prepared by treatment of the appropriate compound with a benzyl halide, such as benzyl bromide, and thereafter, if required, the benzyl group may be conveniently removed using catalytic hydrogenation or a mild ether cleavage reagent such as trimethylsilyl iodide or boron tribromide.

Where appropriate individual isomeric forms of the compounds of formula (I) may be prepared as individual isomers using conventional procedures.

The absolute stereochemistry of compounds may be determined using conventional methods, such as X-ray crystallography.

The derivatives of the compounds of formula (I), including salts and/or solvates, may be prepared and isolated according to conventional procedures.

The compounds of formula (II) are known compounds orthey may be prepared using methods analogous to those used to prepare such compounds such as those described in International Patent Application. Publication Number WO97/34890 and Wiley. R. H. and Slaymaker. S. C. J. Am. Chem. Soc. (80) 1385 (1958). The compounds of formula (II) may be inter-converted in an analogous manner to the above mentioned inter-conversions of the compounds of formula (I).

The compounds of formula (III) are either commercially available, or are reported in the chemical literature, or are prepared by analogy with known conventional literature procedures, for example those disclosed in Chem. Ber., 1892, 25, 2977, J. Amer. Chem. Soc. 1948, 70, 4174–4177, Synthesis 1977, 859, J. Med. Chem., 1994, 37, 3956, Synthesis 1994, 1413, and Tetrahedron, 1991, 47, 2661, or in standard reference texts of synthetic methodology such as J. March, Advanced Organic Chemistry, 3rd Edition (1985), Wiley Interscience.

As stated above, the compounds of formula (I), or pharmnaceutically acceptable derivatives thereof, are indicated to be useful as inhibitors of glycogen synthase kinase-3.

Thus the present invention further provides a compound of formula (I), or a pharmaceutically acceptable derivative thereof, for use as an inhibitor of glycogen synthase kinase-3, and especially for use in the treatment of conditions associated with a need for the inhibition of glycogen synthase kinase-3, such as diabetes, especially Type 2 diabetes, dementias, such as Alzheimer's disease and manic depression.

The present invention also provides the use of a compound of formula (I), or a pharmaceutically acceptable derivative thereof, for the manufacture of a medicament for the treatment of conditions associated with a need for the inhibition of glycogen synthase kinase-3, such as diabetes, especially Type 2 diabetes, dementias, such as Alzheimer's disease and manic depression.

As indicated above, formula (I) comprises a sub-group of compounds of formula (IA). In a further aspect of this invention, there is provided a compound of formula (IA), or a pharmaceutically acceptable derivative thereof, for use as an active therapeutic substance.

Accordingly, the invention also provides a pharmaceutical composition which comprises a compound of formula (IA), or a pharmaceutically acceptable derivative thereof, and a pharmaceutically acceptable carrier.

Preferably, the compounds of formula (I), or pharmaceutically acceptable derivatives thereof are administered as pharmaceutically acceptable compositions.

As indicated above it is considered that GSK-3 inhibitors per se are potentially useful in the treatment and/or prophylaxis of mood disorders, such as schizophrenia. neurotraumatic diseases, such as acute stroke, and for the treatment and/or prophylaxis of cancer and hair loss.

Accordingly, in a further aspect the invention provides a method for the treatment and/or prophylaxis of mood disorders, such as schizophrenia, in a mammal, such as a human, which method comprises the administration of a pharmaceutically acceptable amount of a GSK-3 inhibitor.

The invention also provides a method for the treatment and/or prophylaxis of neurotraumatic diseases in a maammal, such as a human, which method comprises the administration of a pharmaceutically acceptable amount of a GSK-3 inhibitor.

Neurotraumatic diseases include both open or penetrating head trauma, such as caused by surgery, or a closed head trauma injury, such as caused by an injury to the head region ischaemic stroke, including acute stroke, particularly to the brain area transient ischaemic attacks following coronary by-pass and cognitive decline following other transient ischaemic conditions.

Further provided is a method for the treatment and/or prophylaxis of cancer, in a mammal, such as a human, which method comprises the administration of a pharmaceutically acceptable amount of a GSK-3 inhibitor.

In addition there is provided a method for the treatment and/or prophylaxis of hair-loss, in a mammal, such as a human, which method comprises the administration of a pharmaceutically acceptable amount of a GSK-3 inhibitor.

Thus, the invention also provides the use of a GSK-3 inhibitor for the manufacture of a medicament for the treatment and/or prophylaxis of mood disorders, schizophrenia, neurotraumatic diseases, cancer or hair-loss.

A suitable GSK-3 inhibitor is a compound of formula (I) or a pharmaceutically acceptable derivative thereof.

The active compounds are usually administered as the sole medicament agent but they may be administered in combination with other medicament agents as dictated by the severity and type of disease being treated. For example in the treatment of diabetes, especially Type 2 diabetes, a compound of formula (I), or a pharmaceutically acceptable derivative thereof, may be used in combination with other medicament agents, especially antidiabetic agents such as insulin secretagogues, especially sulphonylureas, insulin sensitisers, especially glitazone insulin sensitisers (for example thiazolidinediones), or with biguanides or alpha glucosidase inhibitors or the compound of formula (I), or a pharmaceutically acceptable derivative thereof, may be administered in combination with insulin.

The said combination comprises co-administration of a compound of formula (I), or a pharmaceutically acceptable derivative thereof, and an additional medicament agent or the sequential administration of a compound of formula (I), or a pharmaceutically acceptable derivative thereof, and the additional medicament agent.

Co-administration includes administration of a pharmaceutical composition which contains both a compound of formula (I), or a pharmaceutically acceptable derivative thereof, and the additional medicament agent or the essentially simultaneous administration of separate pharmaceutical compositions of a compound of formula (I), or a pharmaceutically acceptable derivative thereof, and the additional medicament agent The compositions of the invention are preferably adapted for oral administration. However, they may be adapted for other modes of administration.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Preferably the composition are in unit dosage form. A unit dose will generally contain from 0.1 to 1000 mg of the active compound.

Generally an effective administered amount of a compound of the invention will depend on the relative efficacy of the compound chosen, the severity of the disorder being treated and the weight of the sufferer. However, active compounds will typically be administered once or more times a day for example 2, 3 or 4 times daily, with typical total daily doses in the range of from 0.1 to 800 mg/kg/day.

Suitable dose forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine, tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats: emulsifying agents, for example lecithin, sorbitan monooleate, or acacia: non-aqueous vehicles (which may include edible oils), for example almond oil, fractionated coconut oil, oily esters such as esters of glycerine, propylene glycol, or ethyl alcohol: preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and scaling. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The formulations mentioned herein are carried out using standard methods such as those described or referred to in reference texts such as the British and US Pharmacopoeias, Remington's Pharmaceutical Sciences (Mack Publishing Co.), Martindale The Extra Pharmacopoeia (London, The Pharmaceutical Press) or the above mentioned publications.

Suitable methods for preparing and suitable unit dosages for the additional medicament agent, such as the antidiabetic agent mentioned herein include those methods and dosages described or referred to in the above mentioned reference texts.

GSK-3 Assays

Types of GSK-3 assay used to test the compounds of the invention include the following:

Type 1: The GSK-3 specific peptide used in this assay was derived from the phosphorylation site of glycogen synthase and its sequence is: YRRAAVPPSPSLSRHS SPHQ(S)EDEEE. (S) is pre-phosphorylated as is glycogen synthase in vivo and the three consensus sites for GSK-3 specific phosphorylation are underlined. The buffer used to make up the glycogen synthase peptide and [γ-$^{33}$P] ATP consisted of MOPS 25 mM, EDTA 0.2 mM, MgAcetate 10 mM, Tween-20 0.01% and mercaptoethanol 7.5 mM at pH 7.00.

The compounds were dissolved in dimethyl sulphoxide (DMSO) to a final concentration of 100 mM. Various concentrations were made up in DMSO and mixed with the substrate (GSK-3 peptide) solution (to a final concentration 20 μM) described in the above section along with rabbit or human GSK-3α and GSK-3β (final concentration 0.5 U/ml enzyme). The reactions were initiated with the addition of [γ-$^{33}$P] ATP (500 cpm/pmole) spiked into a mixture of ATP (final concentration of 10 μM). After 30 min at room temperature the reaction was terminated by the addition of 10 μl of H$_3$PO$_4$/0.01%Tween-20 (2,5%). A volume (10 μl) of the mixture was spotted onto P-30 phosphocellulose paper (Wallac & Berthold, EG&G Instruments Ltd, Milton Keynes). The paper was washed four times in H$_3$PO$_4$ (0.5%), 2 mins for each wash, air dried and the radioactive phosphate incorporated into the synthetic glycogen synthase peptide, which binds to the P-30 phosphocellulose paper, was counted in a Wallac microbeta scintillation counter.

Analysis of Data: Values for IC$_{50}$ for each inhibitor were calculated by fitting a four-parameter logistic curve to the model: cpm=lower+(upper-lower)/(1+(concentration/IC$_{50}$)$^{slope}$).

Type 2: This protocol is based on the ability of the kinase to phosphorylate a biotinylated 26 mer peptide, sequence of which derived from the phosphorylation site of glycogen synthase and its sequence is Biot- YRRAAVPPSPSLSRHS SPHQ(S)EDEEE, with (S) is a pre-phosphorylated serine as is glycogen synthase in vivo and the three consensus sites for GSK-3 specific phosphorylation are underlined. The phosphorylated biotinylated peptide is then captured onto str-rptavidin coated SPA beads (Amersham Technology), where the signal from the 33P is amplified via the scintillant contained in the beads.

The kinase was assayed at a concentration of 10 nM final in 25 mM MOPS buffer, pH 7.0 containing 0.01% Tween-20, 7.5 mM 2-mercaptoethanol, 10 mM Magnesium acetate. and 10 uM [γ-$^{33}$P]-ATP. After 60 minutes incubation at room temperature, the reaction was stopped by addition of 50 mM EDTA solution containing the Streptavidin coated SPA beads to give a final 0.5 mgs of beads per assay well in a 384 microtiter plate format.

10 mM stock solutions of the compounds of the invention in 100% DMSO are generated as a first step in the screening process. The second step involves the creation of dose response plates where these compounds are diluted across the plate where the final low and high concentrations are to be 0.008 and 10 uM final in the kinase assay. The third step involves the creation of the assay plates. This is achieved by transferring the compounds from four 96 dose response plates to one 384 assay plate on the Robocon Robolab system. The fourth step is to perform the assay as described and count the resulting plates in the Trilux (Wallac 1450 microbeta liquid scintillation and luminescence counter). The final step is data acquisition and analysis where IC$_{50}$ values are generated for each compound in duplicate by fitting a four parameter logistic curve to the model: cpm=lower+(upper-lower)/(1+(concentration/IC$_{50}$)$^{slope}$) in a batch manner.

The most potent compounds of the present invention show IC$_{50}$ values in the range of from between 10 to 100 nM.

No adverse toxicological effects are expected for the compounds of the invention when administered in accordance with the invention.

The following Examples illustrate the invention, but do not limit it in any way.

EXAMPLE 1

3-(3-Bromophenylamino)-4-(4-chlorophenyl)-1H-pyrrole-2,5-dione

A solution of 3-bromoaniline (227 mL, 0.020 mol) and 3-chloro-4-(4-chlorophenyl)-1H-pyrrole-2,5-dione (2.02 g, 0.0083 mol; prepared by analogy with the methods described in WO97/34890 and Wiley, R P H, and Slaymaker, S. C. J. Am. Chem. Soc (80) 1385 (1958)) in methanol (50 mL) was heated at reflux for 40 hours, cooled and concentrated. The residue was acidified with aqueous hydrochloric acid (1M, 200 mL) and extracted with ethyl acetate (3×200 mL). The combined organic solutions were washed with water and brine, dried with magnesium sulphate, evaporated and the residue chromatographed on silica gel using dichloromethane-diethyl ether (gradient from 100:0 to 95:5 v/v) as eluent to afford the title compound as a solid.

$^1$H NMR (DMSO-d$_6$): δ 6.70–7.30 (8H, m), δ 9.65 (1H, br), δ 10.90 (1H, br). MS (APCI+ve): [M+H]$^+$ at m/z 377/379/381 (C$_{16}$H$_{10}$BrClN$_2$O$_2$ requires [M+H]$^+$ at m/z 377/379/381).

EXAMPLE 2

3-(4-Benzoylphenylamino)-4-(4-chlorophenyl)-1H-pyrrole-2-dione

A sealed tube (comprising threaded glass tube with resealable cap) containing a mixture of 4-aminobenzophenone (0.147 g, 0.75 mmol), 3-chloro-4-chlorophenyl)-1H-pyrrole-2,5-dione (0.061 g, 0.25 mmol) and 1-methyl-2-pyrrolidinone (0.5 mL) was irradiated in a microwave reactor for 12 minutes at 100 Watts. The mixture was diluted with aqueous hydrochloric acid (5 mL) and extracted with ethyl acetate (2×5 mL). The combined organic solutions were evaporated and the residue chromatographed on silica gel using dichloromethane as eluent to afford the title compound as a solid.

$^1$H NMR (DMSO-d$_6$): δ 6.85 (2H, d), δ 7.00 (2H, d), δ 7.25 (2H, d), δ 7.35 (2H, d), δ 7.50–7.70 (5H, m), δ 9.95 (1H, s), δ 10.95 (1H, s) MS (APCI–ve): [M]$^+$, at m/z 402/404 (C$_{23}$H$_{15}$ClN$_2$O$_3$ requires [M]$^+$, at m/z 402/404).

EXAMPLE 3

3-(3-Bromo-4-methylphenylamino)-4-(3-nitrophenyl)-1H-pyrrole-2,5-dione

A mixture of 3-bromo-4-methylaniline (0.220 g, 1.18 mmol), 3-chloro-4-(3-nitrophenyl)-1H-pyrrole-2,5-dione (0.100 g, 0.40 mmol) and 1-methyl-2-pyrrolidinone (1.0 mL) was heated in an oil bath at 200° C., for 51 minutes. The mixture was diluted with aqueous hydrochloric acid (5 mL) and extracted with ethyl acetate (5 mL). The combined organic solutions were evaporated and the residue chromatographed on silica gel using dichloromethane as eluent to afford the title compound, a solid, following trituration with dichloromethane-hexane (90:10 v/v).

$^1$H NMR (CDCl$_3$): δ 2.24 (3H, s), δ 6.65–7.70 (7H, m, reduces to 5H on D$_2$O exchange) and δ 8.05 (2H, m). MS (APCI−ve): [M−H]$^-$ at n/z 400/402 (C$_{17}$H$_{12}$BrN$_3$O$_4$ requires [M−H]$^-$ at m/z 400/402).

EXAMPLE 4

3-(4-Methylphenylamino)-4-hydroxyphenyl)-1H-pyrrole-2,5-dione

A mixture of 3-hydroxy-4-(4-hydroxyphenyl)-1H-pyrrole-2,5-dione (103 mg, 0.5 mmol) and 4-methylaniline (59 mg, 0.55 mmol) in 1-methyl-2-pyrrolidinone (1 mL) was heated in a sealed tube at 150° C., for 24 hours. The reaction mixture was dissolved in ethyl acetate(20 mL) and washed with 1N HCl (2×20 mL), water (3×20 mL) and brine (20 mL). The solution was dried over magnesium sulphate, evaporated and the residue chromatographed on silica gel using dichloromethane-diethyl ether (gradient from 100:0 to 90:10 v/v) as eluent to afford the title compound as a solid.

$^1$H NMR (DMSO-d$_6$): δ 2.35 (3H, s), δ 6.50 (2H, d), δ 6.64 (2H, d), δ 6.77 (2H, d), δ 6.90 (2H, d), δ 9.26 (1H, br), δ 9.44 (1H, br), δ 10.64 (1H, br). MS (APCI+ve): [M+H]$^+$ at m/z 295 (C$_{17}$H$_{14}$N$_2$O$_3$ requires [M+H]$^+$ at m/z 295).

EXAMPLE 5

3-(N-Methyl-N-phenylamino)-4-(indol-3-yl)-1H-pyrrole-2,5-dione

A mixture of 3-(N-methyl-N-phenylamino)-4-(indol-3-yl)-1-methyl-1H-pyrrole-2,5-dione (Table B, Example B1; 2.00 g, 0.006 mol), aqueous potassium hydroxide solution (10% w/v, 2 L), ethanol (50 mL) and n-butanol (200 mL) was heated at reflux for 5 hours. The cooled reaction mixture was filtered and the filtrate acidified to pH 1 by addition of one hydrochloric acid. The mixture was cooled to 0° C. and the resulting solid filtered, washed with water and recrystallised from acetonitrile to give the corresponding maleic anhydride. This anhydride (0.4 g, 1.25 mmol) was suspended in a mixture of concentrated aqueous ammonium hydroxide and DMF and heated in stainless steel bomb at 130° C. for 4 hours. The resulting mixture was diluted with water and extracted with dichloromethane and the dried organic solution evaporated to give a solid. This was chromatographed on silica gel using a gradient of 0–5% (v/v) of methanol in dichloromethane as eluent to afford the title compound, a solid.

$^1$H NMR (DMSO-d$_6$): δ 3.07 (3H, s), δ 6.75–7.45 (9H, m), δ 7.68 (1H, s), δ 10.70 (1H, br) and δ 11.70 (1H, br). MS (APCI+ve): [M+H]$^+$ at m/z 318 (C$_{19}$H$_{15}$N$_3$O$_2$ requires [M+H]$^+$ at m/z 318).

Further elution of the chromatography column afforded 3-amino-4-indol-3-yl)-1H-pyrrole-2,5-dione (Table B, Example B2) as a byproduct.

EXAMPLE 6

3-(Indan-5-ylamino)-4-(3-aminophenyl)-1H-pyrrole-2,5-dione 3-(Indan-5-ylamino)-4-(3-nitrophenyl)-1H-pyrrole-2,5-dione (Table A, Example A359: 0.3 g, 0.9 mmol) and 10% Pd/C (60 mg) in ethanol (25 mL) was hydrogenated at atmospheric temperature and pressure for 2 hours. The reaction mixture was filtered through Kieselguhr and the filtrate concentrated in vacuo to give an orange solid. The crude product was taken up in dichloromethane (10 mL) and treated with di-tert-butyl dicarbonate (0.216 g, 1 mmol) and the mixture stirred at ambient temperature for 18 hours. The reaction mixture was poured into saturated aqueous sodium bicarbonate (10 mL) and extracted into dichloromethane (3×10 mL). The combined organics were washed with brine, dried over anhydrous sodium sulfate and concentrated in vacuo. Chromatography on silica gel using dichloromethane-methanol gave the product amine as an orange powder.

$^1$H NMR (DMSO-d$_6$): δ 1.85 (2H, quintet), δ 2.50 (2H, t), δ 2.66 (2H, t), δ 4.82 (2H, s), δ 5.89 (1H, d), δ 6.36 (2H, m), δ 6.47 (1H, s), δ 6.25 (2H, m), δ 6.85 (1H, d), δ 9.13 (1H, br) and δ 10.59 (1H, br). MS (APCI+ve): [M+H]$^+$ at m/z 320 (C$_{19}$H$_{17}$N$_3$O$_2$ requires [M+H]$^+$ at m/z 320).

EXAMPLE 7

3-(Indan-5-ylamino)-4-(3-acetylaminophenyl)-1H-pyrrole-2,5-dione 3-(Indan-5-ylamino)-4-(3-nitrophenyl)-1H-pyrrole-2,5-dione (Table A, Example A359; 0.3 g, 0.9 mmol) and 10% Pd/C (60 mg) in ethanol (25 mL) was hydrogenated at atmospheric temperature and pressure for 2 hours. The reaction mixture was filtered through Kieselguhr and the filtrate concentrated in vacuo to give an orange solid. The crude product was taken up in dichloromethane (5 mL) and treated with acetic anhydride (85 μL, 0.9 mmol) and stirred for 3 hours at ambient temperature. The reaction mixture was poured onto saturated aqueous sodium bicarbonate solution (10 mL) and extracted into ethyl acetate (3×10 mL). The combined organics were washed with brine, dried over anhydrous sodium sulfate and concentrated in vacuo. Chromatography on silica gel using dichloromethane-methanol gave the desired compound as an orange powder.

$^1$H NMR (DMSO-d$_6$): δ 1.83 (2H, quintet), δ 2.02 (3H, s), δ 2.45 (2H, t), δ 2.66 (2H, t), δ 6.41 (2H, m), δ 6.59 (1H, d), δ 6.84 (2H, d), δ 6.90 (1H, t), δ 7.38 (1H, d), δ 9.30 (1H, bs), δ 9.68 (1H, s) and δ 10.61 (1H, bs)] MS (APCI−ve): [M−H]$^-$ at m/z 360 (C$_{21}$H$_{19}$N$_3$O$_3$ requires [M−H]$^-$ at m/z 360).

EXAMPLE 8

3-(Indan-5-ylamino)-4-[3-[(3-fluorophenylaminocarbonyl)amino]phenyl]-1H-pyrrole-2,5-dione 3-(Indan-5-ylamino)-4-(3-aminophenyl)-1H-pyrrole-2,5-dione (Table A, Example A599; 0.08 g, 0.3 mmol) in dichloromethane (10 mL) was was treated with 3-fluorophenyl isocyanate (0.038mg, 0.3 mmol). The mixture was shaken on an orbital shaker for 72 hours. Saturated aqueous sodium bicarbonate (5 mL) was added, shaking continued for 5 minutes and the organic layer transferred directly onto a column of silica gel. Elution with dichloromethane gave the product as a yellow solid.

$^1$H NMR (DMSO-d$_6$): δ 1.78 (2H, quintet), δ 2.44 (2H, t), δ 2.62 (2H, t), δ 6.47 (2H, m), δ 6.61 (1H, dd), δ 6.83 (2H, m), δ 6.93 (2H, m). δ 7.09 (1H, dd), δ 7.28 (2H, m), δ 7.45 (1H, dd). δ 8.42 (1H, br), δ 8.72 (1H, br). δ 9.30 (1H, br) and δ 10.65 (1H, br). MS (APCI−ve) [M]$^-$ at m/z 456 (C$_{26}$H$_{21}$FN$_4$O$_3$ requires [M]$^-$ at m/z 456).

EXAMPLE 9

3-(Indan-5-ylamino)-4-[3-(benzoylamino)phenyl]-1H-pyrrole-2,5-dione 3-(5-Indan-5-ylamino)-4-(3-aminophenyl)-1H-pyrrole-2,5-dione (Table A, Example A599; 0.100 g, 0.3 mmol) in dichloromethane (3 mL) was added to a solution of benzoic acid (0.042 g, 0.33 mmol), 1-hydroxybenzotriazole (0.047 g, 0.33 mmol) and 1-(3-dimethylaminopropyl)-3-ethylcarbodiimide hydrochloride (0.063 g, 0.33 mmol in dichloromethane (5 mL). The mixture was shaken on an orbital shaker for 72 hours. Saturated aqueous sodium bicarbonate (5 mL) was added, shaking continued for 5 minutes and the organic layer transferred directly onto a column of silica gel. Elution with dichloromethane gave the product as a yellow solid.

$^1$H NMR (DMSO-d$_6$): δ 1.83 (2H, quintet), δ 2.43 (2H, t), δ 2.57 (2H, t), δ 6.42 (1H, s), δ 6.30 (2H, m), δ 6.83 (1H, d), δ 7.02 (1H, t), δ 7.22 (1H, s), δ 7.56 (4H, m), δ 7.86 (2H, d), δ 9.38 (1H, br), δ 9.98 (1H, br) and δ 10.68 (1H, bs). MS (APCI−ve): [M−H]$^-$ at m/z 422 (C$_{26}$H$_{21}$N$_3$O$_3$ requires [M−H]$^-$ at m/z 422).

EXAMPLE 10

3-[4-(2-Aminoethyl)phenylamino]-4-(2-methoxyphenyl)-1H-pyrrole-2,5-dione

A solution of 3-[4-[2-(t-butoxycarbonylamino)ethyl] phenylamino]-4-(2-methoxyphenyl)-1H-pyrrole-2,5-dione (0.060 g. 0.13 mmol) and trifluoroacetic acid (4 drops) in dry DCM (5 mL) was stirred for 18 hours at room temperature. The suspension was diluted with ethyl acetate (10 mL), poured onto sodium bicarbonate (20 mL) and extracted with ethyl acetate (3×10 mL). The combined organic solutions were washed with brine, dried with magnesium sulfate, evaporated and the residue triturated with a mixture of hexane-dichloromethane (95:5 v/v) to afford the tide compound as an orange solid.

$^1$H NMR (CDCl$_3$); δ 1.52 (2H, br), δ 2.59 (2H, t), δ 2.83 (2H, t), δ 3.16 (3H, s), δ 6.44 (1H, d), δ 6.58 (2H, d), δ 6.79 (2H, d), δ 6.97–6.93 (1H, m), δ 7.22–7.17 (3H, m) and δ 7.33 (1H, d). MS (APCI+ve): [M+H]$^+$ at m/z 338 (C$_{19}$H$_{19}$N$_3$O$_3$ requires [M+H]$^+$ at 338).

EXAMPLE 11

3-(3-Fluoro-4-methylphenylamino)-4-[4-(methoxycarbonyl)phenyl]-1H-pyrrole-2,5-dione A mixture of 3-(3-Fluoro-4-methylphenyl-amino)-4-(4-iodophenyl)-1H-pyrrole-2,5-dione (Example A705, 126 mg, 0.3 mmol), tetrakis(triphenyl phosphine)-palladium(0) (35 mg, 0.03 mmol) and methanol (10 mL) was placed in a 50 mL two necked round bottomed flask. One arm of the flask was sealed with a septum and to the other arm was fitted a reflux condenser, topped with a multiway tap connected respectively to vacuum, a carbon monoxide cylinder and to a balloon. Using the multiway tap, the flask was alternately evacuated and flushed with carbon monoxide, and the process repeated several times to unsure an atmosphere of carbon monoxide within the flask. The balloon was charged with carbon monoxide and this was then opened to the reaction flask for the duration of the reaction in order to maintain a slight positive pressure of carbon monoxide within the flask. Triethylamine (100 uL, 0.7 mmol) was added and the mixture heated at reflux for 16 hours. The mixture was cooled and diluted with ethyl acetate and the resulting solution washed with aqueous hydrochloric acid (1M, 50 mL), water (50 mL) and brine (50 mL). The organic solution was dried over magnesium sulphate and evaporated to afford a solid. This was chromatographed on silica gel using dichloromethane-ether (98:2 v/v) as eluent to afford the tide compound, a solid.

$^1$H NMR (CDCl$_3$); δ 2.14 (3H, s), δ 3.90 (3H, s), δ 6.35–7.30 (7H, m) and δ 7.82 (2H, m). MS (APCI+ve): [M+H]$^+$ at m/z 355 (C$_{19}$H$_{15}$FN$_2$O$_4$ requires [M+H]$^+$ at 355).

EXAMPLE 12

3-[4-[2-[N-[6-(Acetyiamino)hexyl]aminocarbonyl] ethyl]phenylamino]-4-(3-nitrophenyl)-1H-pyrrole-2,5-dione A solution of triethylamine (81 mg, 0.8 mmol) in dry N,N-diethylformamide (5 mL) was added to a mixture of 3-[4-[2-(hydroxycarbonyl)ethyl]phenylamino]-4-(3-nitrophenyl)-1H-pyrrole-2,5-dione (Example A763, 152 mg, 0.4 mmol), N-(6-aminohexyl)acetamide hydrochloride (78 mg, 0.4 mmol), 1-(3-dimethylamino-propyl)-3-ethylcarbodiimide hydrochloride (77 mg, 0.4 mmol) and 1-hydroxybenzotriazole (54 mg, 0.4 mmol) and the resulting mixture stirred at room temperature for 18 hours. The mixture was diluted with ethyl acetate (25 mL) and washed successively with water (2×25 mL), saturated aqueous sodium bicarbonate solution (25 mL), water (2×25 mL), brine (25 mL), dried over magnesium sulphate and concentrated. The residue was redissolved in dichloromethane-methanol (1:1 v/v), filtered and evaporated to afford the title compound as a foam.

$^1$H NMR (DMSO-d$_6$); δ 1.10–1.40 (8H, m), δ 1.77 (3H, s), δ 2.15 (2H, m), δ 2.55 (2H, m), δ 3.00 (4H, m), δ 6.62 (2H, d), δ 6.77 (2H, d), δ 7.20–7.90 (6H, m), δ 9.80 (1H, br) and δ 10.85 (1H, br). MS (APCI+ve): (M+H]$^+$ at m/z 522 (C$_{27}$H$_{31}$N$_5$O$_6$ requires [M+H]$^+$ at 522).

EXAMPLE 13

3-[4-(trans-2-Carboxyethenyl)phenylamino]-4-(4-chlorophenyl)-1H-pyrrole-2,5-dione A mixture of trans-4-aminocinnamic acid (0.205 g, 1.26 mmol), 3-chloro-4-(4-chlorophenyl)-1H-pyrrole-2,5-dione (0.123 g, 0.51 mmol) and 1-methyl-2-pyrrolidinone (1.0 mL) was heated in a sealed tube in a hotblock set at 69° C., for 28.5 hours. The mixture was diluted with aqueous hydrochloric acid (10 mL) and extracted with ethyl acetate (2×20 mL). The combined organics were washed with brine (2×10 mL), dried over anhydrous magnesium sulphate and evaporated to dryness. The residue was triturated with a mixture of dichloromethane and ethyl acetate to afford the title compound as a solid.

$^1$H NMR (DMSO-d$_6$): δ 6.35 (1H, d), 6.74 (2H, d), 6.99 (2H, d), 7.19 (2H, d), 7.35 (2H, d), 7.42 (1H, d), 9.76 (1H, br), 10.89 (1H, br) and δ 12.23 (1H, br). MS (APCI+ve): [M+H]$^+$ at m/z 369/371. (C$_{19}$H$_{13}$N$_2$O$_4$ requires [M+H]$^+$ at m/z 369/371).

EXAMPLE 14

3-[4-(trans-2-carbamoylethenyl)phenylamino]-4-(4-chlorophenyl)-1H-pyrrole-2,5-dione 3-[4-[trans-2-(ethoxycarbonyl)ethenyl]phenylamino)]-4-(4-chlorophenyl)-1H-pyrrole-2,5-dione (50 mg, 0.126 mmol) was dissolved in 2N methanolic ammonia (5 ml) and allowed to stand at room temp for 12 days. Aqueous ammonia (d 0.88, 5 ml) was added and the solution stood at room temp for a further 8 days. The mixture was evaporated to dryness and the residue triturated with methanol then ether to give the title compound as a solid.

$^1$H NMR (DMSO-d$_6$): δ 10.75 (1H, br), δ 9.7 (1H, br), δ 7.44 (1H, br), δ 7.2 (5H, m), δ 7.2 (3H, m), δ 6.74 (2H, d),

δ 6.41 (1H, d). MS (APCI+ve): [M+H]$^+$ at m/z 368/370 (C$_{19}$H$_{14}$ClN$_3$O$_3$ requires [M+H]$^+$ at m/z 368/370).

EXAMPLE 15

3-(Indol-1-yl)-4-(3-nitrophenyl)-1H-pyrrole-2,5-dione

Sodium hydride (60% dispersion in mineral oil, 30 mg, 0.75 mmol) was added to a solution of indole (88 mg, 0.75 mmol) in THF (2 mL) at room temperature. The mixture was stirred for 30 minutes prior to the addition of a solution of 1-(tert-butyldimethylsilyl)-3-chloro-4-(3-nitrophenyl)-1H-pyrrole-2,5-dione (Procedure method 1, 180 mg, 0.5 mmol) in THF (1 mL). The mixture was stirred for 45 minutes then diluted with ethyl acetate (80 mL), washed with dilute hydrochloric acid (20 mL), dried (MgSO$_4$) and concentrated. The residue was chromatographed on silica gel using a gradient of hexane-ethyl acetate to afford the title compound, a solid.

$^1$H NMR (CD$_3$OD); δ 6.42 (1H, d), 6.77 (1H, d), 6.82 (1H, t), 7.00–7.60 (5H, m) and 8.05–8.25 (2H, m). MS (APCI+ve): [M+H]$^+$ at m/z 334 (C$_{18}$H$_{11}$N$_3$O$_4$ requires [M+H]$^+$ at 334).

EXAMPLE 16

3-Amino-4-(3-nitrophenyl)-1H-pyrrole-2,5-dione 3-chloro-4-(3-nitrophenyl)-1H-pyrrole-2,5-dione (1.0 g, 4 mmol) was suspended in a mixture of ethanol (20 mL) and aqueous 880 ammonia (5 mL) and the mixture heated to 80° C. whilst ammonia gas was bubbled through the mixture for 4 hours. The mixture was cooled and concentrated and the residue chromatographed on silica get using hexane-ethyl acetate (gradient from 1:1 v/v) as eluent to afford the title compound as a solid.

$^1$H NMR (CD$_3$COCD$_3$); δ 6.77 (2H, br), 7.60 (1H, t), 8.04 (2H, m), 8.50 (1H, t) and 9.33 (1H, br). MS (APCI+ve): [M+H]$^+$ at m/z 234 (C$_{10}$H$_7$N$_3$O$_4$ requires [M+H]$^+$ at 234).

EXAMPLE 17

3-[4-[2-Methoxyethylaminocarbonylmethylthio] phenylamino]-4-(4-chlorophenyl)-1H-pyrrole-2,5-dione A solution of 2-methoxyethylamine in THF (0.32M, 1 mL) was added to a mixture of 3-[4-(carboxymethylthio) phenylamino]-4-(4-chlorophenyl)-1H-pyrrole-2,5-dione (Example A941, 117 mg, 0.3 mmol), 1-(3-dimethylaminopropyl)-3-ethylcarbodiimide hydrochloride (57 mg, 0.3 mmol) and 1-hydroxybenzotriazole (40 mg, 0.3 mmol) in dry THF (1 mL). The resulting solution was stirred at room temperature for 57 hours, then diluted with ethyl acetate (50 mL) and washed with dilute hydrochloric acid (1M, 50 ml), water (50 mL) and brine (50 mL), dried over magnesium sulphate and evaporated. The resulting gum was chromatographed on silica gel using dichloromethane-methanol (98:2 v/v) as eluent to afford the tide compound, a solid.

$^1$H NMR (DMSO-d$_6$) d 3.20 (3H, s), 3.21 (2H, n), 3.25 (2H, t), 3,50 (2H, s), 6.60–7.20 (8H, m), 8.10 (1H, t, exchanges with D$_2$O), 9.65 (1H, br, exchanges with D$_2$O) and 10.82 (1H, br, exchanges with D$_2$O). MS (APCI+ve) [M+H]$^+$ at m/z 446/448. C$_{21}$H$_{20}$ClN$_3$O$_4$S requires [M+H]$^+$ at m/z 446/448.

EXAMPLE 18

3-(2-Methoxyethylamino)-4-(4-iodophenyl)-1H-pyrrole-2,5-dione

A solution of 3-(3-fluoro-4-methylphenylamino)-4-(4-iodophenyl)-1H-pyrrole-2,5-dione (Example A705, 126 mg, 0.3 mmol) and 2-methoxyethylazine (0.2 mL, 2,3 mmol) in DMF (2 mL) was stirred at room temperature for 113 hours then diluted with hydrochloric acid (0.5M, 50 mL) and extracted with ethyl acetate (50 mL). The ethyl acetate solution was washed with water (2×50 mL) and brine (50 mL), dried over magnesium sulphate and evaporated. The residue was chromatographed on silica gel using dichloromethane-diethyl ether (99:1 v/v) as eluent to afford the title compound, a solid.

$^1$H NMR (CDCl$_3$): 3.25 (2H, m), 3.35 (3H, s), 3,40 (2H, t), 5.67 (1H, br, exchanges with D$_2$O), 6.95 (1H, br, exchanges with D$_2$O), 7.05 (2H, d) and 7.70 (2H, d). MS (APCI+ve) [M+H]$^+$ at m/z 373. C$_{13}$H$_{13}$IN$_2$O$_3$ requires [M+H]$^+$ at m/z 373.

EXAMPLE 19

3-Amino-1-[4-(4-chlorophenyl)-2,5-dioxo-1H-pyrrol-3-yl]pyridinium chloride

A mixture of 3-chloro-4-(4-chlorophenyl)-1H-pyrrole-2,5-dione (100 mg, 0.41 mmol) and 3-aminopyridine (42.7 mg, 0.45 mmol) in dry THF (2.5 mL) was heated at 50° C. for 2 hours then stirred at room temperature overnight. The resulting suspension was filtered and the solid washed with dichloromethane (20 mL), then hexane (10 mL) to give the title compound as a solid.

$^1$H NMR (DMSO): δ 7.07 (2H, br), δ 7.43 (2H, d), δ 7.61 (2H, d), δ 7.93–7.81 (2H, m), δ 8.10–8.07 (2H, m) and δ 12.07 (1H, br). MS (APCI+ve): [M+H]$^+$ at m/z 301/303 (C$_{15}$H$_{11}$N$_3$O$_2$Cl requires [M+H]$^+$ at m/z 301/303).

EXAMPLE 20

3-[5-Methoxy-6-[4-ethylpiperazin-1-yl]-indolin-1-yl]-4-[3-fluorophenyl]-1H-pyrrole-2,5-dione A solution of 3-chloro-4-(3-fluorophenyl-1H-pyrrole-2,5-dione (100 mg, 0.44 mmol.), 5-methoxy-6-[4-ethylpiperazin-1-yl]-indoline (156 mg, 0.44 mmol.) and triethylamine (0.12 mL, 0.88 mmol.) in dry 1-methylpyrrolidin-2-one (2 mL) was heated under argon at 65° C. for 36 h. The mixture was allowed to stand overnight at RT then diluted with water (80 mL) and extracted with ethyl acetate (3×60 mL). The combined organic solutions were washed with water (2×60 mL), brine, dried with magnesium sulphate, evaporated and the residue triturated with a mixture of dichloromethane and hexane to afford the title compound as a solid.

$^1$H NMR (DMSO-d$_6$): δ 10.80 (1H, br), δ 7.23–7.17 (1H, m), δ 7.00 (1H, t), δ 6.92–6.85 (3H, m). δ 5.44 (1H, s), δ 4.42 (2H, t), δ 3.71 (3H, s), δ 3.12 (2H, t), δ 2.29 (10H, br, s), δ 0.96 (3H, t) MS (APCI+ve): [M+H]$^+$ at m/z 451 (C$_{25}$H$_{27}$N$_4$O$_3$F requires [M+H]$^+$ at m/z 451).

EXAMPLE 21

3-[2-(Hydroxymethyl)indolin-1-yl]-4-(3-nitrophenyl)-1H-pyrrole-2,5-dione Single Enantiomer A solution of racemic 3-[2-(Hydroxymethyl)indolin-1-yl]-4-(3-nitrophenyl)-1H-pyrrole-2,5-dione (Example D102, 30mg) in acetone (1 ml) was separated into it's two enantiomers by repeated high pressure liquid chromatography of aliquots of the solution. The chromatography was performed on a waters 6000 instrument equipped with a 10 mm chiracel AD column using hexane-ethanol (85:15 v/v) as eluent at 5 ml min$^{-1}$. The solvent was removed at reduced pressure to give the separated enantiomers as solids. Enantiomer 1 (12 mg, 100% chiral purity), enantiomer 2 (11 mg, 96% chiral purity).

$^1$H NMR (MeOH): δ 2.07–2.25 (2H, m), 2.48 (1H, dd), 2.65 (1H, dd), 4.10 (1H, hept), 4.45 (1H, d), 5.33 (1H, t), 5.52 (1H, t), 5.95 (1H, d), 6.16 (1H, t), 6.42 (1H, d), 6.78 (1H, dd), 6.85 (1H, d). MS (APCI+ve) [M+H]$^+$ at m/z 366. ($C_{19}H_{15}IN_3O_5$ requires [M+H]$^+$ at m/z 366).

EXAMPLE 22

3-(3,5-Di-fluorophenylamino)-4-(2,3-difluorophenyl)-1H-pyrrole-2,5-dione

A solution of 3,5-difluoroaniline (161 mg, 0.00125 mol) and 3-chloro-4-(2,3-di-fluorophenyl)-1H-pyrrole-2,5-dione (122 mg, 0.0005 mol) in methanol (2 mL) was heated in a sealed tube at 65° C. for 8 days. The mixture was acidified with aqueous hydrochloric acid (1M) and extracted with ethyl acetate. The combined organic solutions were washed with water and brine, dried with magnesium sulphate, evaporated and the residue triturated with hexanedichloromethane (95:5 v/v) to afford the title compound as a solid.

$^1$H NMR (DMSO-d$_6$): δ 6.40 (2H, m), δ 6.75 (1H, m), δ 7.00–7.40 (3H, m), δ 10.00 (1H, br) and δ 11.00 (1H, br). MS (APCI+ve): [M+H]$^+$ at m/z 337 ($C_{16}H_9F_4N_2O_2$ requires [M+H]$^+$ at m/z 337).

Procedure Method 1

1-(tert-Butyldimethylsilyl)-3-chloro-4-(3-nitrophenyl)-1H-pyrrole-2-dione

Triethylamine (1.1 mL, 8 mmol) was added to a stirred suspension of tert-butylchlorodimethylsilane (0.66 g, 4.4 mmol) and 3-chloro-4-(3-nitrophenyl)-1H-pyrrole-2,5-dione (1.0 g, 4 mmol) in dichlommethane (15 mL) at room temperature. The mixture was stirred overnight then chromatographed directly on silica gel using a hexane-acetone gradient to afford the title compound.

$^1$H NMR (CDCl$_3$): δ 0.51 (6H, s), 0.98 (9H, s), 7.70 (1H, t), 8.27 (2H, m) and 8.80 (1H, m). MS (APCI-ve): [M-H]$^-$ at m/z 366/368 ($C_{16}H_{19}ClN_2O_4Si$ requires [M-H]$^-$ at 366/368).

The following additional procedures (Procedure Methods 2 & 3) serve to illustrate a typical preparation of a non commercial aniline, by a method analogous to that described in *Synthesis* 1994, 1413.

Procedure Method 2

3-[(4-Nitrophenyl)thio]Benzoic Acid

A suspension of potassium carbonate (18 g) in acetone (140 mL) at ambient temperature was treated with 3-mercaptobenzoic acid (10 g, 64.4 mmol, 1 eq) followed by 4-nitrofluorobenzene (18 g, 127.7 mmol, 2 eq). The resultant mixture was stirred for 18 h and then poured onto saturated sodium bicarbonate and washed with ethyl acetate. The basic aqueous layer was acidified with 5N HCl and extracted into ethyl acetate (3×100 mL). The combined organics were dried with anhydrous sodium sulphate and concentrated in vacuo to give the product as a solid.

$^1$H NMR (DMSO): δ 7.35 (2H, d), 7.66 (1H, t), 7.81 (1H, m), 8.06 (2H, m), 8.16 (2H, d), and 13.31 (1H, bs). MS (APCI-ve): [M-H]$^-$ at m/z 274 ($C_{13}H_9NO_4S$ requires [M-H]$^-$ at m/z 274).

Procedure Method 3

3-[(4-Aminophenyl)thio]Benzoic Acid

A mixture of 3-[(4-nitrophenyl)thio]benzoic acid (11.2 g, 40.7 mmol) and 10% Pd/C (0.5 g) in ethanol (250 mL) was hydrogenated at atmospheric temperature and pressure for 24 h. The mixture was filtered through Celite and concentrated in vacuo to give the required aniline as a solid.

$^1$H NMR (DMSO): δ 5.59 (2H, bs), 6.64 (2H, d), 7.28 (3H, m), 7.37 (1H, t), 7.52 (1H, s), 7.65 (1H, d), and 12.32 (1H, bs). MS (APCI+ve): [M+H]$^+$ at m/z 246 ($C_{13}H_{11}NO_2S$ requires [M+H]$^+$ at m/z 246).

The further examples described herein were prepared according to the methods disclosed herein, with particular reference to Examples 1 to 22 above. Examples 1 to 22 themselves are shown as examples A1, A2, A3, A424, B3, A599, F1, F2, F6, A702, A770, A772, A832, A833, D19, B25, A968, B28,13, D36, D109 and A929 respectively in Tables A, B, D, F and I.

TABLE A

Encompassing compounds of general formula (XXX-1), wherein group R$^2$ of formula (I) is a phenyl ring, optionally substituted by one or more substituents R$^{10}$ and group R$^3$ of formula (I) is a phenyl ring, optionally substituted by one or more substituents R$^{11}$ and substituents R, R$^1$, R$^{10}$ and R$^{11}$ are listed in Table A.

(XXX-1)

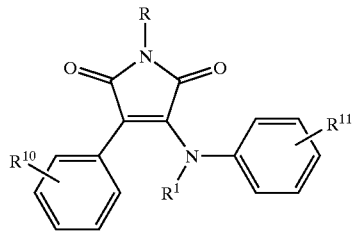

| Example No. | R | R$^1$ | R$^{10}$ | R$^{11}$ | [M + H]$^+$ Observed; (Unless [M]$^-$ or [M − H]$^-$ are Indicated) | For Procedure See Example No. |
|---|---|---|---|---|---|---|
| A1 | H | H | 4-Cl | 3-Br | 377/379/381 | 1 |
| A2 | H | H | 4-Cl | 4-COPh | 402/404 [M]- | 2 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

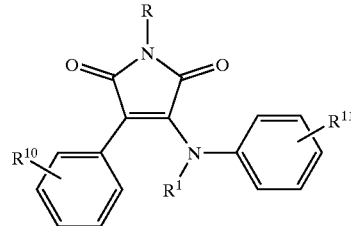

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A3 | H | H | 3-NO2 | 3-Br-4-Me | 400/402 [M − H]− | 3 |
| A4 | H | H | H | H | 265 | 1 |
| A5 | Me | H | H | H | 279 | 1 |
| A6 | H | H | H | 4-OMe | 295 | 1 |
| A7 | H | H | H | 4-Me | 279 | 1 |
| A8 | H | H | H | 4-Cl | 299/301 | 1 |
| A9 | H | H | H | 2-Me | 277 [M − H]− | 1 |
| A10 | H | H | H | 2-OMe | 295 | 1 |
| A11 | H | H | H | 4-OnBu | 337 | 1 |
| A12 | H | H | H | 4-nBu | 321 | 1 |
| A13 | Me | H | H | 4-Cl | 313/315 | 1 |
| A14 | Me | H | H | 4-OMe | 309 | 1 |
| A15 | Et | H | H | H | 293 | 1 |
| A16 | Et | H | H | 4-Cl | 327/329 | 1 |
| A17 | Et | H | H | 4-OMe | 323 | 1 |
| A18 | Ph | H | H | H | 341 | 1 |
| A19 | Ph | H | H | 4-Cl | 375/377 | 1 |
| A20 | Ph | H | H | 4-OMe | 371 | 1 |
| A21 | CH2Ph | H | H | H | 355 | 1 |
| A22 | CH2Ph | H | H | 4-Cl | 389 | 1 |
| A23 | CH2Ph | H | H | 4-OMe | 385 | 1 |
| A24 | H | H | H | 4-SMe | 311 | 1 |
| A25 | H | H | H | 4-(1-Morpholinyl) | 350 | 1 |
| A26 | H | H | H | 3-SMe | 311 | 1 |
| A27 | H | H | H | 3-OPh | 357 | 1 |
| A28 | H | H | H | 4-F | 283 | 1 |
| A29 | H | H | 4-Cl | 4-OMe | 329/331 | 1 |
| A30 | H | H | 4-OMe | 2-OMe | 325 | 1 |
| A31 | H | H | 4-OMe | 4-OnBu | 367 | 1 |
| A32 | H | H | 4-OMe | 3-OPh | 387 | 1 |
| A33 | H | H | 4-OMe | 3-SMe | 341 | 1 |
| A34 | H | H | 4-OMe | 4-F | 313 | 1 |
| A35 | H | H | 4-OMe | 4-SMe | 341 | 1 |
| A36 | H | H | 4-OMe | 4-nBu | 351 | 1 |
| A37 | H | H | 4-OMe | H | 295 | 1 |
| A38 | H | H | 4-OMe | 4-Cl | 329/331 | 1 |
| A39 | H | H | 4-Cl | 3-Cl | 333/335/337 | 1 |
| A40 | H | H | 4-Cl | 2-OMe | 329/331 | 1 |
| A41 | H | H | 4-Cl | 4-OnBu | 371/373 | 1 |
| A42 | H | H | 4-Cl | 3-OPh | 391/393 | 1 |
| A43 | H | H | 4-Cl | 3-SMe | 345/347 | 1 |
| A44 | H | H | 4-Cl | 4-CF3 | 367/369 | 1 |
| A45 | H | H | 4-Cl | 4-F | 317/319 | 1 |
| A46 | H | H | 4-Cl | 4-SMe | 345/347 | 1 |
| A47 | H | H | 4-Cl | 3-CF3 | 367/369 | 1 |
| A48 | H | H | 4-Cl | 4-nBu | 355/357 | 1 |
| A49 | H | H | 4-Cl | H | 299/301 | 1 |
| A50 | H | H | 4-Cl | 2-Me-4-Cl | 347/349/351 | 1 |
| A51 | H | H | 4-Cl | 4-Cl | 333/335/337 | 1 |
| A52 | H | H | 4-Cl | 2-Me | 313/315 | 1 |
| A53 | H | H | 4-Cl | 2,3-[(—CH═CH—)2] | 349/351 | 1 |
| A54 | H | H | 2,3-[(—CH═CH—)2] | 4-OnBu | 387 | 1 |
| A55 | H | H | 2,3-[(—CH═CH—)2] | 4-F | 331 [M − H]− | 1 |
| A56 | H | H | 2,3-[(—CH═CH—)2] | 4-SMe | 361 | 1 |
| A57 | H | H | 2,3-[(—CH═CH—)2] | 4-nBu | 371 | 1 |
| A58 | H | H | 2,3-[(—CH═CH—)2] | H | 315 | 1 |
| A59 | H | H | 4-OMe | 4-OMe | 325 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

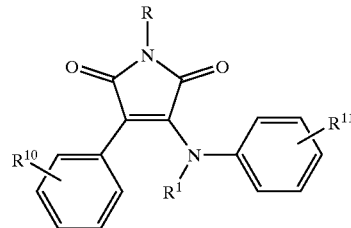

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A60 | H | H | 4-OMe | 3-Cl | 329/331 | 1 |
| A61 | H | H | 4-OMe | 2-Me | 309 | 1 |
| A62 | H | H | 3,4,5-tri-OMe | 4-OMe | 385 | 1 |
| A63 | H | H | 3,4,5-tri-OMe | H | 355 | 1 |
| A64 | H | H | H | 3-Cl | 299 | 1 |
| A65 | H | H | 4-CF3 | 2-Me | 345 [M − H]− | 1 |
| A66 | H | H | 4-CF3 | 2-Et | 359 [M − H]− | 1 |
| A67 | H | H | 4-CF3 | 2-iPr | 375 | 1 |
| A68 | H | H | 4-CF3 | 2-F | 349 [M − H]− | 1 |
| A69 | H | H | 4-CF3 | 2-Cl | 365/367 [M − H]− | 1 |
| A70 | H | H | 4-CF3 | 2-SMe | 379 | 1 |
| A71 | H | H | 4-CF3 | 3-SMe | 379 | 1 |
| A72 | H | H | 4-CF3 | 3-Me | 345 [M − H]− | 1 |
| A73 | H | H | 4-CF3 | 3-Et | 361 | 1 |
| A74 | H | H | 4-CF3 | 3-OMe | 363 | 1 |
| A75 | H | H | 4-CF3 | 3-Cl | 365/367 | 1 |
| A76 | H | H | 4-CF3 | 3-F | 349 [M − H]− | 1 |
| A77 | H | H | 4-CF3 | 3-Br | 409/411 [M − H]− | 1 |
| A78 | H | H | 4-CF3 | 3-I | 457 [M − H]− | 1 |
| A79 | H | H | 4-CF3 | 3-OCH2Ph | 439 | 1 |
| A80 | H | H | 4-CF3 | 3-CONH2 | 375 [M]− | 1 |
| A81 | H | H | 3,4,5-tri-OMe | 4-Cl | 389/391 | 1 |
| A82 | H | H | 4-Cl | 2-Et | 327/329 | 1 |
| A83 | H | H | 4-Cl | 2-iPr | 341/343 | 1 |
| A84 | H | H | 4-Cl | 2-F | 317/319 | 1 |
| A85 | H | H | 4-Cl | 2-SMe | 345/347 | 1 |
| A86 | H | H | 4-Cl | 3-Me | 313/315 | 1 |
| A87 | H | H | 4-Cl | 3-Et | 327/329 | 1 |
| A88 | H | H | 4-Cl | 3-OMe | 329/331 | 1 |
| A89 | H | H | 4-Cl | 3-F | 315/317 [M − H]− | 1 |
| A90 | H | H | 4-Cl | 3-I | 423/425 [M − H]− | 1 |
| A91 | H | H | 4-Cl | 3-OCH2Ph | 405/407 | 1 |
| A92 | H | H | 4-Cl | 3-CONH2 | 342/344 | 1 |
| A93 | H | H | 2-CF3 | 3-SMe | 377 [M − H]− | 1 |
| A94 | H | H | 2-CF3 | 3-Me | 347 | 1 |
| A95 | H | H | 2-CF3 | 3-Et | 361 | 1 |
| A96 | H | H | 4-OMe | 4-Me | 309 | 1 |
| A97 | H | H | 4-OMe | 4-tBu | 351 | 1 |
| A98 | H | H | 4-OMe | 3,4-[(CH2)3] | 335 | 1 |
| A99 | H | H | 4-OMe | 3,5-di-Me | 323 | 1 |
| A100 | H | H | 4-OMe | 3-OCH2Ph | 401 | 1 |
| A101 | H | H | 4-OMe | 3-OMe | 325 | 1 |
| A102 | H | H | 4-OMe | 3-I | 421 | 1 |
| A103 | H | H | 4-OMe | 3,4-[OCH2O] | 339 | 1 |
| A104 | H | H | 4-OMe | 3,5-di-OMe | 355 | 1 |
| A105 | H | H | 3-OMe | 4-nBu | 351 | 1 |
| A106 | H | H | 3-OMe | 3-OPh | 387 | 1 |
| A107 | H | H | 3-OMe | 4-SMe | 341 | 1 |
| A108 | H | H | 3-OMe | 4-Me | 309 | 1 |
| A109 | H | H | 3-OMe | 4-tBu | 351 | 1 |
| A110 | H | H | 3-OMe | 3,5-di-Me | 323 | 1 |
| A111 | H | H | 3-OMe | 3-OCH2Ph | 401 | 1 |
| A112 | H | H | 3-OMe | 3-OMe | 325 | 1 |
| A113 | H | H | 3-OMe | 3-I | 421 | 1 |
| A114 | H | H | 3-OMe | 3,4-[OCH2O] | 339 | 1 |
| A115 | H | H | 3-OMe | 3,5-di-OMe | 355 | 1 |
| A116 | H | H | 3-OMe | 4-OMe | 325 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

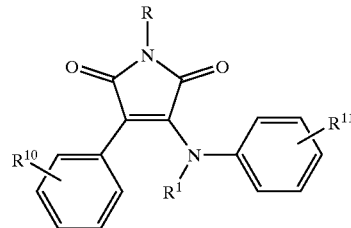

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A117 | H | H | 3-OMe | 3,4-[(CH2)3] | 335 | 1 |
| A118 | H | H | 3-OMe | 4-SCF3 | 395 | 1 |
| A119 | H | H | 2-OMe | 4-nBu | 351 | 1 |
| A120 | H | H | 2-OMe | 3-OPh | 387 | 1 |
| A121 | H | H | 2-OMe | 4-SMe | 341 | 1 |
| A122 | H | H | 2-OMe | 4-Me | 309 | 1 |
| A123 | H | H | 2-OMe | 4-tBu | 351 | 1 |
| A124 | H | H | 2-OMe | 3,4-[(CH2)3] | 335 | 1 |
| A125 | H | H | 2-OMe | 3,5-di-Me | 323 | 1 |
| A126 | H | H | 2-OMe | 3-OCH2Ph | 401 | 1 |
| A127 | H | H | 2-OMe | 3-OMe | 325 | 1 |
| A128 | H | H | 2-OMe | 3-I | 421 | 1 |
| A129 | H | H | 2-OMe | 3,5-di-OMe | 355 | 1 |
| A130 | H | H | 2-OMe | 4-OMe | 325 | 1 |
| A131 | H | H | 2-OMe | 3-CF3 | 363 | 1 |
| A132 | H | H | 4-OMe | 3-CF3 | 363 | 1 |
| A133 | H | H | 3-OMe | 3-CF3 | 363 | 1 |
| A134 | H | H | 2-OMe | 3,4-[OCH2O] | 339 | 1 |
| A135 | H | Me | 4-CF3 | H | 347 | 1 |
| A136 | H | H | 4-CF3 | H | 333 | 2 |
| A137 | H | H | 4-CF3 | 2,3-[(—CH=CH—)2] | 383 | 2 |
| A138 | H | H | 4-CF3 | 4-CF3 | 401 | 2 |
| A139 | H | H | 4-CF3 | 4-CN | 358 | 2 |
| A140 | H | H | 4-CF3 | 4-COPh | 437 | 2 |
| A141 | H | H | 2-CF3 | H | 333 | 2 |
| A142 | H | H | 2-CF3 | 2-Me | 347 | 2 |
| A143 | H | H | 4-CF3 | 2-Me-4-Cl | 381/383 | 2 |
| A144 | H | H | 4-OMe | 3-CH2OH | 325 | 1 |
| A145 | H | H | H | 2,3-[(—CH=CH—)2] | 315 | 1 |
| A146 | H | H | 4-Cl | 3-OH | 315/317 | 1 |
| A147 | H | Me | H | H | 279 | 1 |
| A148 | H | Me | 4-Ph | H | 355 | 1 |
| A149 | H | Me | 4-Cl | H | 313/315 | 1 |
| A150 | H | Me | 4-OMe | H | 309 | 1 |
| A151 | H | Me | 3-NO2 | H | 324 | 1 |
| A152 | H | Me | 3-OMe | H | 309 | 1 |
| A153 | H | H | 4-CF3 | 4-CO2H | 377 | 2 |
| A154 | H | H | 4-Ph | 4-Me | 355 | 1 |
| A155 | H | H | 4-Ph | 4-OnBu | 412 [M]- | 1 |
| A156 | H | H | 4-Ph | 4-nBu | 397 | 1 |
| A157 | H | H | 4-Ph | 4-SMe | 387 | 1 |
| A158 | H | H | 4-Ph | 2-Me | 355 | 1 |
| A159 | H | H | 4-Ph | 3-SMe | 387 | 1 |
| A160 | H | H | 4-Ph | 3-OPh | 433 | 1 |
| A161 | H | H | 4-Ph | 3-Cl | 375/377 | 1 |
| A162 | H | H | 4-Ph | 3-COMe | 383 | 1 |
| A163 | H | H | 4-Ph | 3-Br | 417/419 [M − H]- | 1 |
| A164 | H | H | 4-Ph | 3-(5-Oxazolyl) | 407 [M]- | 1 |
| A165 | H | H | 4-Ph | 3-OH | 357 | 1 |
| A166 | H | H | 3-NO2 | 4-Me | 324 | 1 |
| A167 | H | H | 3-NO2 | 4-OnBu | 382 | 1 |
| A168 | H | H | 3-NO2 | 4-SMe | 356 | 1 |
| A169 | H | H | 3-NO2 | 2-Me | 324 | 1 |
| A170 | H | H | 3-NO2 | 3-SMe | 356 | 1 |
| A171 | H | H | 3-NO2 | 3-OPh | 402 | 1 |
| A172 | H | H | 3-NO2 | 3-Cl | 344/346 | 1 |
| A173 | H | H | 3-NO2 | 3,5-di-Cl | 376/378/380 [M − H]- | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

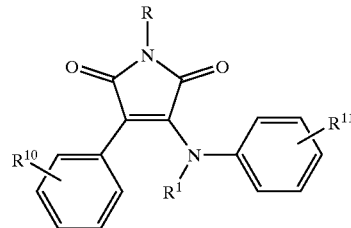

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A174 | H | H | 3-NO2 | 3-COMe | 350 [M − H]− | 1 |
| A175 | H | H | 3-NO2 | 3-Br | 388/390 | 1 |
| A176 | H | H | 3-NO2 | 3-(5-Oxazolyl) | 375 [M − H]− | 1 |
| A177 | H | H | 3-NO2 | 3-OH | 326 | 1 |
| A178 | H | H | 3-NO2 | 4-nBu | 366 | 1 |
| A179 | H | H | 4-CF3 | 4-NO2 | 378 | 2 |
| A180 | H | H | 3,4,5-tri-OMe | 4-Me | 369 | 1 |
| A181 | H | H | 3,4,5-tri-OMe | 4-OnBu | 427 | 1 |
| A182 | H | H | 3,4,5-tri-OMe | 4-nBu | 411 | 1 |
| A183 | H | H | 3,4,5-tri-OMe | 4-SMe | 401 | 1 |
| A184 | H | H | 3,4,5-tri-OMe | 3-SMe | 401 | 1 |
| A185 | H | H | 3,4,5-tri-OMe | 3-COMe | 397 | 1 |
| A186 | H | H | 3,4,5-tri-OMe | 3-(5-Oxazolyl) | 422 | 1 |
| A187 | H | H | 3,4,5-tri-OMe | 3-OH | 371 | 1 |
| A188 | H | H | H | 4-CF3 | 333 | 1 |
| A189 | H | H | 4-OMe | 4-(CH2)2OH | 337 [M − H]− | 1 |
| A190 | H | H | H | 4-(CH2)2OH | 309 | 1 |
| A191 | H | H | 2-Cl | 4-OMe | 329 | 1 |
| A192 | H | H | H | 3-CF3 | 331 [M − H]− | 1 |
| A193 | H | H | 4-Cl | 4-CN | 323/325 [M]− | 2 |
| A194 | H | H | 4-CF3 | 2,4,6-tri-Me | 375 | 2 |
| A195 | H | H | 4-Cl | 2,3-[(CH2)4] | 353/355 | 1 |
| A196 | H | H | 4-Cl | 4-tBu | 355/357 | 1 |
| A197 | H | H | 4-Cl | 4-CH2P(O)(OEt)2 | 449/451 | 1 |
| A198 | H | H | 4-Cl | 4-OPh | 391/393 | 1 |
| A199 | H | H | 4-Cl | 4-(Cyclohexyl) | 381/383 | 1 |
| A200 | H | H | 4-Cl | 2-CH2Ph | 389/391 | 1 |
| A201 | H | H | 4-Cl | 4-Br-3-Cl | 411/413/415/417 | 1 |
| A202 | H | H | 4-Cl | 4-I-3-Cl | 459/461/463 | 1 |
| A203 | H | H | 4-Cl | 3,4-di-Cl | 367/369/371/373 | 1 |
| A204 | H | H | 4-Cl | 3,5-di-Cl | 367/369/371/373 | 1 |
| A205 | H | H | 4-Cl | 3,5-di-Cl-4-OH | 383/385/387/389 | 1 |
| A206 | H | H | 4-Cl | 3,5-di-F | 335/337 | 1 |
| A207 | H | H | 4-Cl | 4-Br | 377/379/381 | 1 |
| A208 | H | H | 4-Cl | 4-I | 425/427 | 1 |
| A209 | H | H | 4-Cl | 3-NO2 | 344/346 | 1 |
| A210 | H | H | 4-Cl | 2-OH | 315/317 | 1 |
| A211 | H | H | 4-Cl | 4-OH | 315/317 | 1 |
| A212 | H | H | 4-Cl | 3,5-di-Br-4-Me | 469/471/473/475 | 1 |
| A213 | H | H | 4-Cl | 3,4-[OCH2O] | 343/345 | 1 |
| A214 | H | H | 4-Cl | 3,4-[CH=N—NH] | 339/341 | 1 |
| A215 | H | H | 4-Cl | 3,4-[NH—N=CH] | 339/341 | 1 |
| A216 | H | H | 4-Cl | 3-Br-2-Me | 391/393/395 | 1 |
| A217 | H | H | 4-Cl | 3-Br-4-Me | 391/393/395 | 1 |
| A218 | H | H | 4-Cl | 3-Cl-2-Me | 347/349/351 | 1 |
| A219 | H | H | 4-Cl | 3-F-4-Me | 331/333 | 1 |
| A220 | H | H | 4-Cl | 3-F-6-Me | 331/333 | 1 |
| A221 | H | H | 4-Cl | 4-Me | 313/315 | 1 |
| A222 | H | H | 4-Cl | 2-CH2OH | 329/331 | 1 |
| A223 | H | H | 4-Cl | 3-CH2OH | 329/331 | 1 |
| A224 | H | H | 4-Cl | 4-OH-2-Me | 329/331 | 1 |
| A225 | H | H | 4-Cl | 4-NHCOMe | 356/358 | 1 |
| A226 | H | H | 4-Cl | 2,3-di-Me | 327/329 | 1 |
| A227 | H | H | 4-Cl | 2,4-di-Me | 327/329 | 1 |
| A228 | H | H | 4-Cl | 3,4-di-Me | 327/329 | 1 |
| A229 | H | H | 4-Cl | 3,5-di-Me | 327/329 | 1 |
| A230 | H | H | 4-Cl | 3-CH2OH-6-Me | 343/345 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

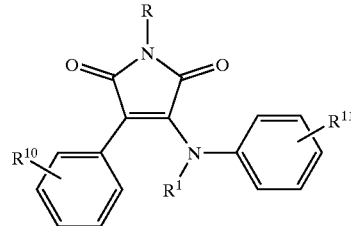

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A231 | H | H | 4-Cl | 4-OMe-2-Me | 343/345 | 1 |
| A232 | H | H | 4-Cl | 4-(CH2)2OH | 343/345 | 1 |
| A233 | H | H | 4-Cl | 3,5-di-OMe | 359/361 | 1 |
| A234 | H | H | 4-Cl | 4-CH2CN | 338/340 | 1 |
| A235 | H | H | 4-Cl | 3,4-[CH=CH—NH] | 338/340 | 1 |
| A236 | H | H | 4-Cl | 3-COMe | 341/343 | 1 |
| A237 | H | H | 4-Cl | 4-CH2CO2H | 357/359 | 1 |
| A238 | H | H | 4-Cl | 3,4-[(CH2)3] | 337/339 [M − H]− | 1 |
| A239 | H | H | 4-Cl | 4-N(Me)COMe | 370/372 | 1 |
| A240 | H | H | 4-Cl | 3-OiPr | 357/359 | 1 |
| A241 | H | H | 4-Cl | 4-(CH2)2CONH2 | 370/372 | 1 |
| A242 | H | H | 3,4-[OCH2O] | 3-OPh | 401 | 1 |
| A243 | H | H | 4-Cl | 4-CONH2 | 340/342 [M − H]− | 3 |
| A244 | H | H | 4-F | 2-Me | 297 | 1 |
| A245 | H | H | 4-F | 3-SMe | 329 | 1 |
| A246 | H | H | 4-F | 3-Cl | 317/319 | 1 |
| A247 | H | H | 4-F | 4-Cl-2-Me | 331/333 | 1 |
| A248 | H | H | 4-F | 3-OPh | 375 | 1 |
| A249 | H | H | 4-F | 4-SMe | 329 | 1 |
| A250 | H | H | 4-F | 4-tBu | 339 | 1 |
| A251 | H | H | 4-F | 3,4-[(CH2)3] | 323 | 1 |
| A252 | H | H | 2-OMe | 3-Me | 309 | 1 |
| A253 | H | H | 2-OMe | 3-F | 313 | 1 |
| A254 | H | H | 2-OMe | 2-F | 313 | 1 |
| A255 | H | H | 2-OMe | 4-Cl-2-Me | 343/345 | 1 |
| A256 | H | H | 2-OMe | 2-Me | 309 | 1 |
| A257 | H | H | 2-OMe | 3-SMe | 341 | 1 |
| A258 | H | H | 3-Cl | 2-Me | 313/315 | 1 |
| A259 | H | H | 3-Cl | 3-SMe | 345/347 | 1 |
| A260 | H | H | 3-Cl | 3-Cl | 333/335/337 | 1 |
| A261 | H | H | 3-Cl | 4-Cl-2-Me | 347/349/351 | 1 |
| A262 | H | H | 3-Cl | 3-OPh | 391/393 | 1 |
| A263 | H | H | 3-Cl | 4-SMe | 345/347 | 1 |
| A264 | H | H | 3-Cl | 4-tBu | 355/357 | 1 |
| A265 | H | H | 3-Cl | 3,4-[(CH2)3] | 339/341 | 1 |
| A266 | H | H | 3,4-[(—CH=CH—)2] | 3-Me | 329 | 1 |
| A267 | H | H | 3,4-[(—CH=CH—)2] | 3-F | 333 | 1 |
| A268 | H | H | 3,4-[(—CH=CH—)2] | 4-Cl-2-Me | 363/365 | 1 |
| A269 | H | H | 3,4-[(—CH=CH—)2] | 2-Me | 329 | 1 |
| A270 | H | H | 3,4-[(—CH=CH—)2] | 3-SMe | 361 | 1 |
| A271 | H | H | 3,4-[(—CH=CH—)2] | 3-Cl | 349/351 | 1 |
| A272 | H | H | 4-I | 2-Me | 405 | 1 |
| A273 | H | H | 4-I | 3-SMe | 437 | 1 |
| A274 | H | H | 4-I | 3-Cl | 425/427 | 1 |
| A275 | H | H | 4-I | 4-Cl-2-Me | 439/441 | 1 |
| A276 | H | H | 4-I | 3-OPh | 483 | 1 |
| A277 | H | H | 4-I | 4-SMe | 437 | 1 |
| A278 | H | H | 4-I | 4-tBu | 447 | 1 |
| A279 | H | H | 4-I | 3,4-[(CH2)3] | 431 | 1 |
| A280 | H | H | 4-OMe | 3-Me | 309 | 1 |
| A281 | H | H | 4-OMe | 3-F | 313 | 1 |
| A282 | H | H | 3-OMe | 2-Me | 309 | 1 |
| A283 | H | H | 3-OMe | 3-SMe | 341 | 1 |
| A284 | H | H | 3-OMe | 3-Cl | 329/331 | 1 |
| A285 | H | H | 2-OMe | 3-Cl | 329/331 | 1 |
| A286 | H | H | 4-F | 3-Br | 361/363 | 1 |
| A287 | H | H | 4-OMe | 3-Br | 373/375 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

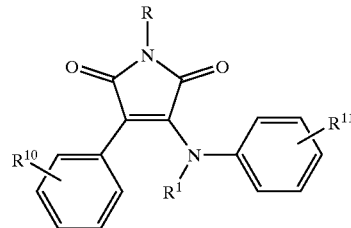

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A288 | H | H | 3,4-[(—CH=CH—)2] | 3-Br | 393/395 | 1 |
| A289 | H | H | 4-I | 3-Br | 469/471 | 1 |
| A290 | H | H | 4-Cl | 4-NO2 | 342/344 [M − H]− | 3 |
| A291 | H | H | 3,4-di-Cl | 3-Br | 411/413/415/417 | 1 |
| A292 | H | H | 3-Cl | 3-Br | 377/379/381 | 1 |
| A293 | H | H | 2-Cl | 3-OPh | 391/393 | 3 |
| A294 | H | H | 2-Cl | 3-Cl | 333/335 | 3 |
| A295 | H | H | 2-Cl | 3-SMe | 345/347 | 1 |
| A296 | H | H | 2-Cl | 4-SMe | 345/347 | 1 |
| A297 | H | H | 3-OMe | 4-CONH2 | 337 [M]− | 3 |
| A298 | H | H | 4-Cl | 4-CO2H | 297/299 Fragmention [M − CO2H]− | 3 |
| A299 | H | H | 4-OMe | 4-CN | 320 | 3 |
| A300 | H | H | 2-Cl | 4-nBu | 355/357 | 1 |
| A301 | H | H | 2-Cl | 3-Br | 375/377/379 [M]− | 1 |
| A302 | H | H | 2-Cl | 4-Me | 313/315 | 1 |
| A303 | H | H | 4-Cl | 3-Cl-6-Me | 347/349/351 | 3 |
| A304 | H | H | 3-NO2 | 3-Cl-4-Me | 356/358 [M − H]− | 3 |
| A305 | H | H | 3-NO2 | 4-COPh | 414 | 3 |
| A306 | H | H | 3,5-di-F | 3-Br | 379/381 | 1 |
| A307 | H | H | 3-CF3 | 3-Br | 411/413 | 1 |
| A308 | H | H | 4-Me | 3-Br | 357/359 | 1 |
| A309 | H | H | 4-Br | 3-SMe | 389/391 | 1 |
| A310 | H | H | 4-Br | 4-Me | 357/359 | 1 |
| A311 | H | H | 4-Br | 3,5-di-Cl | 409/411/413/415 [M − H]− | 1 |
| A312 | H | H | 4-Br | 3-OPh | 435/437 | 1 |
| A313 | H | H | 4-Br | 3,4-[(CH2)3] | 383/385 | 1 |
| A314 | H | H | 4-Me | 3-SMe | 325 | 1 |
| A315 | H | H | 4-Me | 4-Me | 293 | 1 |
| A316 | H | H | 4-Me | 3-OPh | 371 | 1 |
| A317 | H | H | 4-Me | 3,4-[(CH2)3] | 319 | 1 |
| A318 | H | H | 4-Me | 4-SMe | 325 | 1 |
| A319 | H | H | 4-SMe | 3-SMe | 357 | 1 |
| A320 | H | H | 4-SMe | 4-Me | 325 | 1 |
| A321 | H | H | 4-SMe | 3-OPh | 403 | 1 |
| A322 | H | H | 4-SMe | 3,4-[(CH2)3] | 351 | 1 |
| A323 | H | H | 4-SMe | 4-SMe | 357 | 1 |
| A324 | H | H | 3-CF3 | 3-SMe | 379 | 1 |
| A325 | H | H | 3-CF3 | 4-Me | 347 | 1 |
| A326 | H | H | 3-CF3 | 3,5-di-Cl | 399/401/403 [M − H]− | 1 |
| A327 | H | H | 3-CF3 | 3-OPh | 425 | 1 |
| A328 | H | H | 3-CF3 | 3,4-[(CH2)3] | 373 | 1 |
| A329 | H | H | 3-CF3 | 4-SMe | 379 | 1 |
| A330 | H | H | 3,5-di-F | 3-SMe | 347 | 1 |
| A331 | H | H | 3,5-di-F | 4-Me | 315 | 1 |
| A332 | H | H | 3,5-di-F | 3,5-di-Cl | 367/369/371 [M]− | 1 |
| A333 | H | H | 3,5-di-F | 3-OPh | 393 | 1 |
| A334 | H | H | 3,5-di-F | 3,4-[(CH2)3] | 341 | 1 |
| A335 | H | H | 3,5-di-F | 4-SMe | 347 | 1 |
| A336 | H | H | 3,4-di-Cl | 3-SMe | 379/381/383 | 1 |
| A337 | H | H | 3,4-di-Cl | 4-Me | 347/349/351 | 1 |
| A338 | H | H | 3,4-di-Cl | 3,5-di-Cl | 399/401/403/405/407 [M − H]− | 1 |
| A339 | H | H | 3,4-di-Cl | 3-OPh | 423/425/427 [M]− | 1 |
| A340 | H | H | 3,4-di-Cl | 3,4-[(CH2)3] | 373/375/377 | 1 |
| A341 | H | H | 3,4-di-Cl | 4-SMe | 379/381/383 | 1 |
| A342 | H | H | 3-Br | 3-SMe | 389/391 | 1 |
| A343 | H | H | 3-Br | 4-Me | 355/357 [M]− | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

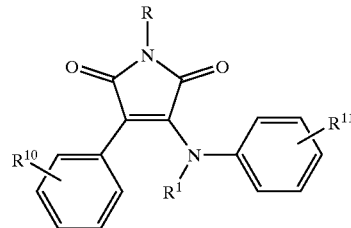

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A344 | H | H | 3-Br | 3,5-di-Cl | 409/411/413/415 [M − H]− | 1 |
| A345 | H | H | 3-Br | 3-OPh | 435/437 | 1 |
| A346 | H | H | 3-Br | 3,4-[(CH2)3] | 383/385 | 1 |
| A347 | H | H | 3-Br | 4-SMe | 389/391 | 1 |
| A348 | H | H | 4-NO2 | 3-SMe | 356 | 1 |
| A349 | H | H | 4-NO2 | 4-Me | 324 | 1 |
| A350 | H | H | 4-NO2 | 3,5-di-Cl | 376/378/380 [M − H]− | 1 |
| A351 | H | H | 4-NO2 | 3-OPh | 402 | 1 |
| A352 | H | H | 4-NO2 | 3,4-[(CH2)3] | 350 | 1 |
| A353 | H | H | 4-NO2 | 4-SMe | 356 | 1 |
| A354 | H | H | 4-Br | 4-SMe | 389/391 | 1 |
| A355 | H | H | 3-NO2 | 4-NO2 | 353 [M]− | 3 |
| A356 | H | H | 3-NO2 | 3,5-di-Cl-4-OH | 392/394/396 [M − H]− | 1 |
| A357 | H | H | 3-NO2 | 4-tBu | 366 | 1 |
| A358 | H | H | 3-NO2 | 3,5-di-Br-4-OH | 482/484/486 | 1 |
| A359 | H | H | 3-NO2 | 3,4-[(CH2)3] | 350 | 1 |
| A360 | H | H | 3-NO2 | 3-Br-4-OCF3 | 470/472 [M − H]− | 1 |
| A361 | H | H | 3-NO2 | 3-Br-5-CF3 | 454/456 [M − H]− | 1 |
| A362 | H | H | 3-NO2 | 4-CH2CN | 349 | 1 |
| A363 | H | H | 3-NO2 | 4-(CH2)2CONH2 | 381 | 1 |
| A364 | H | H | 3-NO2 | 3-F | 326 [M − H]− | 1 |
| A365 | H | H | 3-NO2 | 3-F-4-Me | 342 | 1 |
| A366 | H | H | 3-NO2 | 4-Cl | 342/344 [M − H]− | 1 |
| A367 | H | H | 3-NO2 | 4-OMe | 340 | 1 |
| A368 | H | H | 3-NO2 | 3-Et | 338 | 1 |
| A369 | H | H | 3-NO2 | 2-F | 328 | 1 |
| A370 | H | H | 3-NO2 | 3,5-di-F | 344 [M − H]− | 1 |
| A371 | H | H | 3-NO2 | 3,4-[S—CH=N] | 367 | 1 |
| A372 | H | H | 3-NO2 | 4-OPh | 402 | 1 |
| A373 | H | H | 3-NO2 | 4-trans-CH=CHCO2H | 378 [M − H]− | 1 |
| A374 | H | H | 3-NO2 | 4-OCH2Ph | 416 | 1 |
| A375 | H | H | 3-NO2 | 3-CO(CH2)2CO2Me | 422 [M − H]− | 1 |
| A376 | H | H | 3-NO2 | 3-NO2 | 353 [M]− | 3 |
| A377 | H | H | 3-NO2 | 4-CN | 333 [M]− | 3 |
| A378 | H | H | 4-Cl | 4-OH-3-CO2H | 359/361 | 1 |
| A379 | H | H | 4-Cl | 3-CO2H | 341/343 [M − H]− | 1 |
| A380 | H | H | 4-Cl | 4-SCH2CO2Me | 403/405 | 1 |
| A381 | H | H | 4-Cl | 4-OH-3-NO2 | 360/362 | 1 |
| A382 | H | H | 4-Cl | 4-(CH2)2CO2H | 371/373 | 1 |
| A383 | H | H | 4-Cl | 4-Cl-3-CO2H | 375/377/379 [M − H]− | 1 |
| A384 | H | H | 4-Cl | 4-(CH2)3CO2H | 385/387 | 1 |
| A385 | H | H | 4-Cl | 3-SO2CF3 | 429/431 [M − H]− | 1 |
| A386 | H | H | 4-Cl | 3-COPh | 403/405 | 1 |
| A387 | H | H | 4-Cl | 3,5-di-Br-4-OH | 471/473/475/477 | 1 |
| A388 | H | H | 4-Cl | 4-CPh3 | 541/543 | 1 |
| A389 | H | H | 4-Cl | 3-CH2CO2H | 355/357 [M − H]− | 1 |
| A390 | H | H | 4-Cl | 4-(1-Adamantyl) | 433/435 | 1 |
| A391 | H | H | 4-Cl | 3-CO2H-4-[S-(2-CO2H—Ph)] | 373/375 Fragmention [M − C7H5O2]− | 1 |
| A392 | H | H | 4-Cl | 2-[O(CH2)2OMe]-5-(CH2)2CO2H | 443/445 [M − H]− | 1 |
| A393 | H | H | 4-Cl | 3-Br-4-Cl | 411/413/415/417 | 1 |
| A394 | H | H | 4-Cl | 2-OPh | 391/393 | 1 |
| A395 | H | H | 4-Cl | 4-CH2SO2NHMe | 311/313 Fragmention [M − CH4NO2S]+ | 1 |
| A396 | H | H | 3-NO2 | 4-CO2H | 352 [M − H]− | 3 |
| A397 | H | H | 3-NO2 | 3-COPh | 414 | 3 |
| A398 | H | H | 4-Cl | 3-CH2CO2Me | 371/373 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

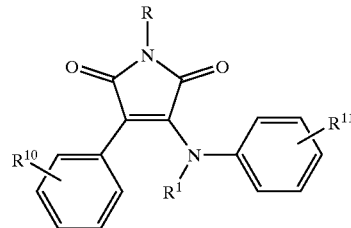

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A399 | H | H | 4-OH | 3-Br | 359/361 | 4 |
| A400 | H | H | 4-Br | 4-COPh | 447/449 | 3 |
| A401 | H | H | 4-SMe | 4-COPh | 415 | 3 |
| A402 | H | H | 4-OH | 4-SMe | 327 | 4 |
| A403 | H | H | 4-iPr | 3-SMe | 351 [M − H]- | 1 |
| A404 | H | H | 4-iPr | 4-Me | 319 [M − H]- | 1 |
| A405 | H | H | 4-iPr | 3,4-[(CH2)3] | 345 [M − H]- | 1 |
| A406 | H | M | 3,5-di-Me | 3-SMe | 337 [M − H]- | 1 |
| A407 | H | H | 3,5-di-Me | 4-Me | 305 [M − H]- | 1 |
| A408 | H | H | 3,5-di-Me | 3,4-[(CH2)3] | 331 [M − H]- | 1 |
| A409 | H | H | 3,5-di-Me | 4-SMe | 337 [M − H]- | 1 |
| A410 | H | H | 4-iPr | 4-SMe | 351 [M − H]- | 1 |
| A411 | H | H | 2-Br | 3-SMe | 387/389 [M − H]- | 1 |
| A412 | H | H | 2-Br | 4-Me | 355/357 [M − H]- | 1 |
| A413 | H | H | 2-Br | 3,4-[(CH2)3] | 381/383 [M − H]- | 1 |
| A414 | H | H | 2-Br | 4-SMe | 387/389 [M − H]- | 1 |
| A415 | H | H | 3,5-bis-CF3 | 3-SMe | 446 [M]- | 1 |
| A416 | H | H | 3,5-bis-CF3 | 4-Me | 414 [M]- | 1 |
| A417 | H | H | 3,5-bis-CF3 | 3,5-di-Cl | 468/470/472 [M]- | 1 |
| A418 | H | H | 3,5-bis-CF3 | 3,4-[(CH2)3] | 440 [M]- | 1 |
| A419 | H | H | 3,5-bis-CF3 | 4-SMe | 446 [M]- | 1 |
| A420 | H | H | 4-OPh | 3-SMe | 401 [M − H]- | 1 |
| A421 | H | H | 4-OPh | 4-Me | 369 [M]- | 1 |
| A422 | H | H | 4-OPh | 3,4-[(CH2)3] | 395 [M − H]- | 1 |
| A423 | H | H | 4-OPh | 4-SMe | 401 [M − H]- | 1 |
| A424 | H | H | 4-OH | 4-Me | 295 | 4 |
| A425 | H | H | 4-OCH2Ph | 3-SMe | 415 [M − H]- | 1 |
| A426 | H | H | 4-OCH2Ph | 3,4-[(CH2)3] | 409 [M − H]- | 1 |
| A427 | H | H | 4-OCH2Ph | 4-SMe | 415 [M − H]- | 1 |
| A428 | H | H | 3,4-di-OMe | 3-SMe | 371 | 1 |
| A429 | H | H | 3,4-di-OMe | 4-Me | 337 [M − H]- | 1 |
| A430 | H | H | 3,4-di-OMe | 3,4-[(CH2)3] | 363 [M − H]- | 1 |
| A431 | H | H | 3-Cl-4-OMe | 4-SMe | 373/375 [M − H]- | 1 |
| A432 | H | H | 3-Cl-4-OMe | 3-SMe | 373/375 [M − H]- | 1 |
| A433 | H | H | 3-Cl-4-OMe | 4-Me | 341/343 [M − H]- | 1 |
| A434 | H | H | 3-Cl-4-OMe | 3,4-[(CH2)3] | 369/371 | 1 |
| A435 | H | H | 3-NO2 | 4-COMe | 352 | 3 |
| A436 | H | H | 4-OH | 3-OPh | 371 [M − H]- | 4 |
| A437 | H | H | 4-OH | 3-Br-4-Me | 371/373 [M − H]- | 4 |
| A438 | H | H | 4-OH | 3,4-[(CH2)3] | 321 | 4 |
| A439 | H | H | 3,5-di-Me | 3-OPh | 383 [M − H]- | 1 |
| A440 | H | H | 2-Br | 3-OPh | 434 [M − H]- | 1 |
| A441 | H | H | 3,5-bis-CF3 | 3-OPh | 492 [M]- | 1 |
| A442 | H | H | 4-OCH2Ph | 3-OPh | 461 [M − H]- | 1 |
| A443 | H | H | 3-Cl-4-OMe | 3-OPh | 419/421 [M − H]- | 1 |
| A444 | H | H | 3,4-di-OMe | 3-OPh | 415 [M − H]- | 1 |
| A445 | H | H | 4-OPh | 3-OPh | 447 [M − H]- | 1 |
| A446 | H | H | 4-OCH2Ph | 4-Me | 383 [M − H]- | 1 |
| A447 | H | H | 2-Cl | 3-Cl-4-Me | 347/349/351 | 3 |
| A448 | H | H | 3,4-[OCH2O] | 3-SMe | 353 [M − H]- | 1 |
| A449 | H | H | 3,4-[OCH2O] | 4-Me | 323 | 1 |
| A450 | H | H | 3,4-[OCH2O] | 3,4-[(CH2)3] | 349 | 1 |
| A451 | H | H | 3,4-[OCH2O] | 4-SMe | 355 | 1 |
| A452 | H | H | 3,4-[OCH2O] | 3-Br | 387/389 | 1 |
| A453 | H | H | 3,4-[OCH2O] | 3-Br-4-Me | 401/403 | 1 |
| A454 | H | H | 2-Me | 4-Me | 293 | 1 |
| A455 | H | H | 2-Me | 3,4-[(CH2)3] | 319 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

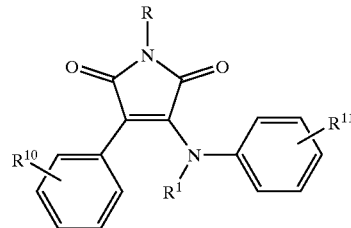

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A456 | H | H | 2-Me | 4-SMe | 325 | 1 |
| A457 | H | H | 3-Me | 3-OPh | 371 | 1 |
| A458 | H | H | 3-Br | 4-Cl | 375/377/379 [M − H]− | 1 |
| A459 | H | H | 4-iPr | 3-OPh | 397 [M − H]− | 1 |
| A460 | H | H | 4-CH2OMe | 3-SMe | 353 [M − H]− | 1 |
| A461 | H | H | 4-CH2OMe | 4-Me | 321 [M − H]− | 1 |
| A462 | H | H | 4-CH2OMe | H | 307 [M − H]− | 1 |
| A463 | H | H | 4-CH2OMe | 3-OPh | 399 [M − H]− | 1 |
| A464 | H | H | 4-CH2OMe | 3,4-[(CH2)3] | 347 [M − H]− | 1 |
| A465 | H | H | 4-CH2OMe | 4-SMe | 353 [M − H]− | 1 |
| A466 | H | H | 4-CH2OMe | 3-Br | 385/387 [M − H]− | 1 |
| A467 | H | H | 4-CH2OMe | 3-Br-4-Me | 399/401 [M − H]− | 1 |
| A468 | H | H | 2-Me | 4-Cl | 313/315 | 1 |
| A469 | H | H | 2,5-di-OMe | 3-SMe | 369 [M − H]− | 1 |
| A470 | H | H | 2,5-di-OMe | 4-Me | 337 [M − H]− | 1 |
| A471 | H | H | 2,5-di-OMe | H | 323 [M − H]− | 1 |
| A472 | H | H | 2,5-di-OMe | 3-OPh | 415 [M − H]− | 1 |
| A473 | H | H | 2,5-di-OMe | 3,4-[(CH2)3] | 363 [M − H]− | 1 |
| A474 | H | H | 2,5-di-OMe | 4-SMe | 369 [M − H]− | 1 |
| A475 | H | H | 2,5-di-OMe | 3-Br | 401/403 [M − H]− | 1 |
| A476 | H | H | 2,5-di-OMe | 3-Br-4-Me | 415/417 [M − H]− | 1 |
| A477 | H | H | 4-OCF3 | 3-SMe | 393 [M − H]− | 1 |
| A478 | H | H | 4-OCF3 | 4-Me | 361 [M − H]− | 1 |
| A479 | H | H | 4-OCF3 | H | 347 [M − H]− | 1 |
| A480 | H | H | 4-OCF3 | 3-OPh | 439 [M − H]− | 1 |
| A481 | H | H | 4-OCF3 | 3,4-[(CH2)3] | 387 [M − H]− | 1 |
| A482 | H | H | 4-OCF3 | 3-Br | 425/427 [M − H]− | 1 |
| A483 | H | H | 4-OCF3 | 3-Br-4-Me | 439/441 [M − H]− | 1 |
| A484 | H | H | 4-OCF3 | 4-SMe | 393 [M − H]− | 1 |
| A485 | H | H | 3-SCF3 | 3-SMe | 409 [M − H]− | 1 |
| A486 | H | H | 3-SCF3 | 4-Me | 377 [M − H]− | 1 |
| A487 | H | H | 3-SCF3 | H | 363 [M − H]− | 1 |
| A488 | H | H | 3-SCF3 | 3-OPh | 455 [M − H]− | 1 |
| A489 | H | H | 3-SCF3 | 3,4-[(CH2)3] | 403 [M − H]− | 1 |
| A490 | H | H | 3-SCF3 | 4-SMe | 409 [M − H]− | 1 |
| A491 | H | H | 3-SCF3 | 3-Br | 441/443 [M − H]− | 1 |
| A492 | H | H | 3-SCF3 | 3-Br-4-Me | 455/457 [M − H]− | 1 |
| A493 | H | H | 3-Cl | 4-Cl | 333/335/337 | 1 |
| A494 | H | H | 4-Cl | 3,4-[S—CH=N] | 356/358 | 1 |
| A495 | H | H | 2-OMe | 3,4-[S—CH=N] | 352 | 1 |
| A496 | H | H | 4-OMe | 3,4-[S—CH=N] | 352 | 1 |
| A497 | H | H | 4-Br | 4-CH=CHCO2H | 411/413 [M − H]− | 1 |
| A498 | H | H | 4-Br | 4-CH(OMe)Me | 401/403 | 1 |
| A499 | H | H | 2-Me | 3-SMe | 325 | 1 |
| A500 | H | H | 2-Me | 3-Br-4-Me | 371/373 | 1 |
| A501 | H | H | 3-F | 3-SMe | 329 | 1 |
| A502 | H | H | 3-F | 4-Me | 297 | 1 |
| A503 | H | H | 3-F | 3,5-di-Cl | 351/353/355 | 1 |
| A504 | H | H | 3-F | 3-OPh | 375 | 1 |
| A505 | H | H | 3-F | 3,4-[(CH2)3] | 323 | 1 |
| A506 | H | H | 3-F | 4-SMe | 329 | 1 |
| A507 | H | H | 3-F | 3-Br | 361/363 | 1 |
| A508 | H | H | 3-F | 3-Br-4-Me | 375/377 | 1 |
| A509 | H | H | 2,4-di-Cl | 3-SMe | 379/381/383 | 1 |
| A510 | H | H | 2,4-di-Cl | 4-Me | 347/349/350 | 1 |
| A511 | H | H | 2,4-di-Cl | 3-OPh | 425/427/429 | 1 |
| A512 | H | H | 2,4-di-Cl | 3,4-[(CH2)3] | 373/375/377 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

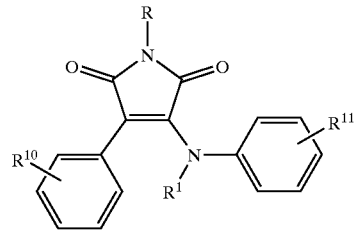

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A513 | H | H | 2,4-di-Cl | 4-SMe | 379/381/383 | 1 |
| A514 | H | H | 2,4-di-Cl | 3-Br | 411/413/415/417 | 1 |
| A515 | H | H | 2,4-di-Cl | 3-Br-4-Me | 425/427/429/431 | 1 |
| A516 | H | H | 3-Me | 3-SMe | 325 | 1 |
| A517 | H | H | 3-Me | 4-Me | 293 | 1 |
| A518 | H | H | 3-Me | 3,4-[(CH2)3] | 319 | 1 |
| A519 | H | H | 3-Me | 4-SMe | 325 | 1 |
| A520 | H | H | 3-Me | 3-Br | 357/359 | 1 |
| A521 | H | H | 3-Me | 3-Br-4-Me | 371/373 | 1 |
| A522 | H | H | 4-Cl-3-NO2 | 3-SMe | 388/390 [M − H]− | 1 |
| A523 | H | H | 4-Cl-3-NO2 | 4-Me | 356/358 [M − H]− | 1 |
| A524 | H | H | 4-Cl-3-NO2 | 3,5-di-Cl | 410/412/414/416 [M − H]− | 1 |
| A525 | H | H | 4-Cl-3-NO2 | 3-OPh | 434/436 [M − H]− | 1 |
| A526 | H | H | 4-Cl-3-NO2 | 3,4-[(CH2)3] | 384/386 | 1 |
| A527 | H | H | 4-Cl-3-NO2 | 4-SMe | 390/392 | 1 |
| A528 | H | H | 4-Cl-3-NO2 | 3-Br-4-Me | 434/436/438 [M − H]− | 1 |
| A529 | H | H | 4-OH | 3,4-[S—CH=N] | 338 | 4 |
| A530 | H | H | 4-SMe | 3,4-[S—CH=N] | 368 | 1 |
| A531 | H | H | 4-I | 3,4-[S—CH=N] | 448 | 1 |
| A532 | H | H | 2-Cl | 3,4-[S—CH=N] | 356/358 | 1 |
| A533 | H | H | 4-Cl-3-NO2 | 3-Br | 420/422/424 [M − H]− | 1 |
| A534 | H | H | 3-NO2 | 3-CH2OH | 338 [M − H]− | 1 |
| A535 | H | H | 3-NO2 | 3-CONH2 | 351 [M − H]− | 1 |
| A536 | H | H | 3-NO2 | 3-OCH2CO2Et | 410 [M − H]− | 1 |
| A537 | H | H | 3-NO2 | 3,4-di-Me | 336 [M − H]− | 1 |
| A538 | H | H | 3-NO2 | 3-CO2H | 352 [M − H]− | 1 |
| A539 | H | H | 3-NO2 | 3,4-[OCH2O] | 352 [M − H]− | 1 |
| A540 | H | H | 3-NO2 | 3-CH2CO2Me | 380 [M − H]− | 1 |
| A541 | H | H | 3-NO2 | 3-OCH2CO2Me | 396 [M − H]− | 1 |
| A542 | H | H | 4-Br | 3-Cl-4-Me | 391/393/395 | 1 |
| A543 | H | H | 4-Me | 3-Cl-4-Me | 327/329 | 1 |
| A544 | H | H | 4-SMe | 3-Cl-4-Me | 359/361 | 1 |
| A545 | H | H | 2-OMe | 3-Cl-4-Me | 343/345 | 1 |
| A546 | H | H | 4-OMe | 3-Cl-4-Me | 343/345 | 1 |
| A547 | H | H | 2-Cl | 3-Br-4-Me | 391/393/395 | 1 |
| A548 | H | H | 4-Br | 3-Br-4-Me | 435/437/439 | 1 |
| A549 | H | H | 4-Me | 3-Br-4-Me | 371/373 | 1 |
| A550 | H | H | 4-SMe | 3-Br-4-Me | 403/405 | 1 |
| A551 | H | H | 2-OMe | 3-Br-4-Me | 387/389 | 1 |
| A552 | H | H | 4-OMe | 3-Br-4-Me | 387/389 | 1 |
| A553 | H | H | 2-Cl | H | 299/301 | 1 |
| A554 | H | H | 4-Br | H | 343/345 | 1 |
| A555 | H | H | 4-Me | H | 279 | 1 |
| A556 | H | H | 4-SMe | H | 311 | 1 |
| A557 | H | H | 2-OMe | H | 295 | 1 |
| A558 | H | H | 3-NO2 | 3-Cl-4-OH | 358/360 [M − H]− | 1 |
| A559 | H | H | 3-NO2 | 3-Cl-4-OMe | 374/376 | 1 |
| A560 | H | H | 3-NO2 | 3-F-4-OMe | 358 | 1 |
| A561 | H | H | 3-NO2 | 3,5-di-Br | 464/466/468 [M − H]− | 1 |
| A562 | H | H | 3-NO2 | 3,5-di-Br-4-Me | 478/480/482 [M − H]− | 1 |
| A563 | H | H | 3-NO2 | 3,5-di-Me | 338 | 1 |
| A564 | H | H | 3-NO2 | H | 310 | 1 |
| A565 | H | H | 2-Me | 3-OPh | 371 | 1 |
| A566 | H | H | 3-NO2 | 4-(CH2)2OH | 352 [M − H]− | 1 |
| A567 | H | H | 3-NO2 | 4-CH2CO2H | 366 [M − H]− | 1 |
| A568 | H | H | 3-NO2 | 4-CH2P(O)(OEt)2 | 460 | 1 |
| A569 | H | H | 3-NO2 | 4-CH2SO2NHMe | 415 [M − H]− | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

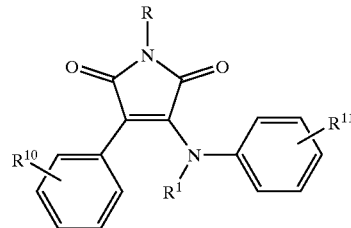

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
| --- | --- | --- | --- | --- | --- | --- |
| A570 | H | H | 3-NO2 | 4-SCH2CO2H | 398 [M − H]− | 1 |
| A571 | H | H | 3-NO2 | 4-OH | 324 [M − H]− | 1 |
| A572 | H | H | 3-NO2 | 4-(CH2)3CO2H | 394 [M − H]− | 1 |
| A573 | H | H | 3-NO2 | 4-CH2CO2Me | 380 [M − H]− | 1 |
| A574 | H | H | 3-NO2 | 4-SCH2CO2Me | 412 [M − H]− | 1 |
| A575 | H | H | 3-NO2 | 4-(CH2)3CO2Me | 410 | 1 |
| A576 | H | H | 3-NO2 | 3,4-[CH=N—NH] | 350 | 1 |
| A577 | H | H | 3-NO2 | 3,4-[NH—N=CH] | 350 | 1 |
| A578 | H | H | 4-Me | 3,4-[S—CH=N] | 336 | 1 |
| A579 | H | H | 4-Br | 3,4-[S—CH=N] | 400/402 | 1 |
| A580 | H | H | 3,5-di-F | 3,4-[S—CH=N] | 358 | 1 |
| A581 | H | H | 3-NO2 | 2-Ph | 384 [M − H]− | 1 |
| A582 | H | H | 2-OMe | 3-Et | 323 | 1 |
| A583 | H | H | 2-OMe | 3-OH | 311 | 1 |
| A584 | H | H | 2-OMe | 3-Br | 373/375 | 1 |
| A585 | H | H | 2-OMe | 3-COMe | 337 | 1 |
| A586 | H | H | 2-OMe | 3-COPh | 399 | 1 |
| A587 | H | H | 2-OMe | 3-F-4-Me | 327 | 1 |
| A588 | H | H | 2-OMe | 3,5-di-Br-4-OH | 467/469/471 | 1 |
| A589 | H | H | 2-OMe | 4-CH2CN | 334 | 1 |
| A590 | H | H | 2-OMe | 4-(CH2)2CONH2 | 366 | 1 |
| A591 | H | H | 2-OMe | 4-Cl | 329/321 | 1 |
| A592 | H | H | 2-OMe | 4-OPh | 387 | 1 |
| A593 | H | H | 2-OMe | 4-OCH2Ph | 401 | 1 |
| A594 | H | H | 2-OMe | 3-F-4-OMe | 343 | 1 |
| A595 | H | H | 2-OMe | 3-Cl-4-OMe | 357/359 [M − H]− | 1 |
| A596 | H | H | 2-OMe | 3-Cl-4-OH | 345/347 | 1 |
| A597 | H | H | 2-OMe | 4-Br-3-Cl | 407/409/411 | 1 |
| A598 | H | H | 2-OMe | 3-Br-4-OCF3 | 457/459 | 1 |
| A599 | H | H | 3-NH2 | 3,4-[(CH2)3] | 320 | 6 |
| A600 | H | H | 4-SMe | 2-Ph | 385 [M − H]− | 1 |
| A601 | H | H | 3-NO2 | 4-I | 435 [M]− | 1 |
| A602 | H | H | 2-OMe | 3-NO2 | 340 | 1 |
| A603 | H | H | 2-OMe | 3,5-di-F | 331 | 1 |
| A604 | H | H | 2-OMe | 3-Br-5-CF3 | 441/443 | 1 |
| A605 | H | H | 2-OMe | 3,5-di-Cl-4-OH | 379/381/383 | 1 |
| A606 | H | H | 2-OMe | 4-trans-CH=CHCO2H | 363 [M − H]− | 1 |
| A607 | H | H | 3-OPh | 4-Me | 371 | 1 |
| A608 | H | H | 3-OPh | 3-Br | 433/435 [M − H]− | 1 |
| A609 | H | H | 3-OPh | 4-SMe | 401 [M − H]− | 1 |
| A610 | H | H | 3-OPh | 3-OPh | 447 [M − H]− | 1 |
| A611 | H | H | 3-OPh | 3,4-[(CH2)3] | 395 [M − H]− | 1 |
| A612 | H | H | 3-OPh | H | 357 | 1 |
| A613 | H | H | 3-OPh | 3-SMe | 403 | 1 |
| A614 | H | H | 3-OPh | 3-Br-4-Me | 447/449 [M − H]− | 1 |
| A615 | H | H | 4-OnBu | 4-Me | 349 [M − H]− | 1 |
| A616 | H | H | 4-OnBu | 3-OPh | 428 [M]− | 1 |
| A617 | H | H | 4-OnBu | 3,4-[(CH2)3] | 377 | 1 |
| A618 | H | H | 4-OnBu | H | 337 | 1 |
| A619 | H | H | 4-OnBu | 3-SMe | 383 | 1 |
| A620 | H | H | 4-OnBu | 3-Br-4-Me | 427/429 [M − H]− | 1 |
| A621 | H | H | 2,6-di-Cl | 4-Me | 347/349/351 | 1 |
| A622 | H | H | 2,6-di-Cl | H | 331/333/335 [M − H]− | 1 |
| A623 | H | H | 2,6-di-Cl | 3-SMe | 377/379/381 [M − H]− | 1 |
| A624 | H | H | 4-SMe | 3-Br | 389/391 | 1 |
| A625 | H | H | 4-SMe | 3-Cl | 345/347 | 1 |
| A626 | H | H | 3,5-di-F | 3-NO2 | 344 [M − H]− | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

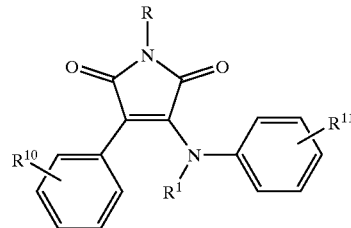

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A627 | H | H | 2-Cl | 3,4-di-Me | 327/329 | 1 |
| A628 | H | H | 4-Br | 3,4-di-Me | 369/371 [M − H]− | 1 |
| A629 | H | H | 4-Br | 3-Br | 419/421/423 [M − H]− | 1 |
| A630 | H | H | 4-Br | 3-Cl | 375/377/379 [M − H]− | 1 |
| A631 | H | H | 3-Br | 3-NO2 | 386/388 [M − H]− | 1 |
| A632 | H | H | 2-OMe | 3,4-di-Me | 323 | 1 |
| A633 | H | H | 3-OMe | 3,4-di-Me | 323 | 1 |
| A634 | H | H | 3-OPh | 3,4-di-Me | 385 | 1 |
| A635 | H | H | 4-SMe | 3,4-di-Me | 337 [M − H]− | 1 |
| A636 | H | H | 3-OPh | 4-Br | 433/435 [M − H]− | 1 |
| A637 | H | H | 4-Me | 3-Cl | 313/315 | 1 |
| A638 | H | H | 2-OMe | 4-(CH2)2NHCO2tBu | 436 [M − H]− | 1 |
| A639 | H | H | 3-NO2 | 2,3-[(CH2)4] | 362 [M − H]− | 1 |
| A640 | H | H | 3-Cl | 3-NO2 | 342/344 [M − H]− | 1 |
| A641 | H | H | 2-OMe | 4-CH2NHCO2tBu | 422 [M − H]− | 1 |
| A642 | H | H | 4-OnBu | 4-SMe | 383 | 1 |
| A643 | H | H | 4-C(OMe)2Ph | 3-Cl | 417/419 Fragmention [M − OMe]+ | 1 |
| A644 | H | H | 4-COPh | 3-Cl | 403/405 | 1 |
| A645 | H | H | 3-NO2-4-OMe | 3-Cl | 374/376 | 1 |
| A646 | H | H | 2-NO2 | 3-Cl | 344/346 | 1 |
| A647 | H | H | 2,4-di-OMe | 3-SMe | 369 [M − H]− | 1 |
| A648 | H | H | 2,4-di-OMe | 4-Me | 337 [M − H]− | 1 |
| A649 | H | H | 2,4-di-OMe | H | 323 [M − H]− | 1 |
| A650 | H | H | 2,4-di-OMe | 3-OPh | 415 [M − H]− | 1 |
| A651 | H | H | 2,4-di-OMe | 3,4-[(CH2)3] | 363 [M − H]− | 1 |
| A652 | H | H | 2,4-di-OMe | 4-SMe | 369 [M − H]− | 1 |
| A653 | H | H | 2,4-di-OMe | 3-Br | 403/404 | 1 |
| A654 | H | H | 2,4-di-OMe | 3-Br-4-Me | 415/417 [M − H]− | 1 |
| A655 | H | H | 3-NO2 | 3-Cl-4-SMe | 388/390 [M − H]− | 1 |
| A656 | H | H | 2-OMe | 3-Cl-4-SMe | 373/375 [M − H]− | 1 |
| A657 | H | H | 3-NO2 | 4-CH2NHBoc | 437 [M − H]− | 1 |
| A658 | H | H | 4-Br | 4-NMe2 | 386/388 | 1 |
| A659 | H | H | 2-OMe | 4-NMe2 | 338 | 1 |
| A660 | H | H | 3-NO2 | 4-NMe2 | 353 | 1 |
| A661 | H | H | 3-NO2 | 3-OMe | 373/375 | 1 |
| A662 | H | H | 3-NO2 | 3-OMe | 340 | 1 |
| A663 | H | H | 4-Br | 3,4-di-OMe | 403/405 | 1 |
| A664 | H | H | 2-OMe | 3,4-di-OMe | 355 | 1 |
| A665 | H | H | 3-NO2 | 3,4-di-OMe | 370 | 1 |
| A666 | H | H | 4-SO2Me | 3-Br-4-Me | 433/435 [M − H]− | 1 |
| A667 | H | H | 4-SO2Me | 3-Br | 419/421 [M − H]− | 1 |
| A668 | H | H | 4-SO2Me | 4-SMe | 388 [M]− | 1 |
| A669 | H | H | 4-SO2Me | 3,4-[(CH2)3] | 382 [M]− | 1 |
| A670 | H | H | 4-SO2Me | 3-OPh | 434 [M]− | 1 |
| A671 | H | H | 4-SO2Me | H | 342 [M]− | 1 |
| A672 | H | H | 4-SO2Me | 4-Me | 356 [M]− | 1 |
| A673 | H | H | 4-SO2Me | 3-SMe | 388 [M]− | 1 |
| A674 | H | H | 2-F | 3-SMe | 327 [M − H]− | 1 |
| A675 | H | H | 2-F | 4-Me | 295 [M − H]− | 1 |
| A676 | H | H | 2-F | 3-OPh | 373 [M − H]− | 1 |
| A677 | H | H | 2-F | 3,4-[(CH2)3] | 321 [M − H]− | 1 |
| A678 | H | H | 2-F | 4-SMe | 327 [M − H]− | 1 |
| A679 | H | H | 2-F | 3-Br | 359/361 [M − H]− | 1 |
| A680 | H | H | 2-F | 3-Br-4-Me | 373/375 [M − H]− | 1 |
| A681 | H | H | 2,3-di-F | 3-Br-4-Me | 391/393 [M − H]− | 1 |
| A682 | H | H | 2,3-di-F | 3-Br | 377/379 [M − H]− | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

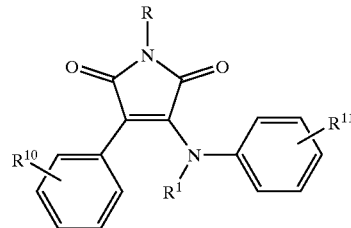

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A683 | H | H | 2,3-di-F | 4-SMe | 345 [M − H]− | 1 |
| A684 | H | H | 2,3-di-F | 3,4-[(CH2)3] | 339 [M − H]− | 1 |
| A685 | H | H | 2,3-di-F | 3-OPh | 391 [M − H]− | 1 |
| A686 | H | H | 2,3-di-F | H | 299 [M − H]− | 1 |
| A687 | H | H | 2,3-di-F | 4-Me | 313 [M − H]− | 1 |
| A688 | H | H | 2,3-di-F | 3-SMe | 345 [M − H]− | 1 |
| A689 | H | H | 3-NO2 | 3,4-[N=N—NH] | 351 | 1 |
| A690 | H | Me | 3-NO2 | 2-Me | 338 | 1 |
| A691 | H | H | 3-NO2 | 2-OH | 326 | 1 |
| A692 | H | H | 3-NO2 | 3-CF3 | 376 [M − H]− | 1 |
| A693 | H | H | 3-NO2 | 3-OCH2Ph | 414 [M − H]− | 1 |
| A694 | H | H | 3-NO2 | 3-CO2H-4-Cl | 386 [M − H]− | 1 |
| A695 | H | H | 3-NO2 | 3-CO2Me | 368 | 1 |
| A696 | H | H | 3-NO2 | 2-OMe | 340 | 1 |
| A697 | H | H | 3-NO2 | 3-I | 436 | 1 |
| A698 | H | H | 3-NO2 | 3-CO2Me-4-Cl | 402/404 | 1 |
| A699 | H | H | 3-NO2-4-OMe | 3,4-[(CH2)3] | 380 | 1 |
| A700 | H | H | 3-NO2-4-OMe | 3-Br-4-Me | 432/434 | 1 |
| A701 | H | H | 3-NO2 | 4-(CH2)2NHBoc | 451 [M − H]− | 1 |
| A702 | H | H | 2-OMe | 4-(CH2)2NH2 | 338 | 10 |
| A703 | H | H | 2-F | H | 281 [M − H]− | 1 |
| A704 | H | H | 4-Br | 4-CH2NHBoc | 470/472 [M − H]− | 1 |
| A705 | H | H | 4-I | 3-F-4-Me | 421 [M − H]− | 1 |
| A706 | H | H | 2-OCH2Ph | 3-Cl | 405/407 | 1 |
| A707 | H | H | 2-Cl | 3,5-di-Cl-4-OH | 383/385/387/389 | 1 |
| A708 | H | H | 2-Cl | 3,5-di-Br-4-OH | 471/473/475/477 | 1 |
| A709 | H | H | 2-Cl | 3-CO2H-4-Cl | 377/379/381 | 1 |
| A710 | H | H | 2-Cl | 3-CO2H | 343/345 | 1 |
| A711 | H | H | 2-Cl | 3-OH | 315/317 | 1 |
| A712 | H | H | 2-Cl | 3,4-[OCH2O] | 343/345 | 1 |
| A713 | H | H | 2-Cl | 3,4-[(CH2)3] | 339/341 | 1 |
| A714 | H | H | H | 3,5-di-Cl-4-OH | 349/351/353 | 1 |
| A715 | H | H | H | 3,5-di-Br-4-OH | 437/439/441 | 1 |
| A716 | H | H | H | 3-CO2H-4-Cl | 343/345 | 1 |
| A717 | H | H | H | 3-CO2H | 309 | 1 |
| A718 | H | H | H | 3-OH | 281 | 1 |
| A719 | H | H | H | 3,4-[OCH2O] | 309 | 1 |
| A720 | H | H | H | 3,4-[(CH2)3] | 305 | 1 |
| A721 | H | H | 3-NO2-4-OMe | H | 340 | 1 |
| A722 | H | H | 3-NO2-4-OMe | 4-SMe | 386 | 1 |
| A723 | H | H | 4-Br | 3,5-di-Cl-4-OH | 427/429/431/433 | 1 |
| A724 | H | H | 4-Br | 3,5-di-Br-4-OH | 515/517/519/521 | 1 |
| A725 | H | H | 4-Br | 3-CO2H-4-Cl | 419/421/423 [M − H]− | 1 |
| A726 | H | H | 4-Br | 3-CO2H | 387/389 | 1 |
| A727 | H | H | 4-Br | 3-OH | 359/361 | 1 |
| A728 | H | H | 4-Br | 3,4-[OCH2O] | 387/389 | 1 |
| A729 | H | H | 4-I | 3,5-di-Cl-4-OH | 475/477/479 | 1 |
| A730 | H | H | 4-I | 3,5-di-Br-4-OH | 563/565/567 | 1 |
| A731 | H | H | 4-I | 3-CO2H-4-Cl | 469/471 | 1 |
| A732 | H | H | 4-I | 3-CO2H | 435 | 1 |
| A733 | H | H | 4-I | 3-OH | 407 | 1 |
| A734 | H | H | 4-I | 3,4-[OCH2O] | 435 | 1 |
| A735 | H | H | 3-Me | 3,5-di-Cl-4-OH | 363/365/367 | 1 |
| A736 | H | H | 3-Me | 3,5-di-Br-4-OH | 451/453/455 | 1 |
| A737 | H | H | 3-Me | 3-CO2H-4-Cl | 357/359 | 1 |
| A738 | H | H | 3-Me | 3-CO2H | 323 | 1 |
| A739 | H | H | 3-Me | 3-OH | 295 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

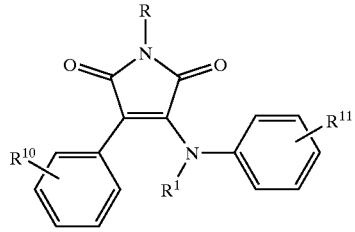

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A740 | H | H | 3-Me | 3,4-[OCH2O] | 323 | 1 |
| A741 | H | H | 3-F | 3,5-di-Cl-4-OH | 367/369/371 | 1 |
| A742 | H | H | 3-F | 3,5-di-Br-4-OH | 455/457/459 | 1 |
| A743 | H | H | 3-F | 3-CO2H-4-Cl | 361/363 | 1 |
| A744 | H | H | 3-F | 3-CO2H | 327 | 1 |
| A745 | H | H | 3-F | 3-OH | 299 | 1 |
| A746 | H | H | 3-F | 3,4-[OCH2O] | 327 | 1 |
| A747 | H | H | 4-OMe | 3,5-di-Cl-4-OH | 379/381/383 | 1 |
| A748 | H | H | 4-OMe | 3,5-di-Br-4-OH | 467/469/471 | 1 |
| A749 | H | H | 4-OMe | 3-CO2H | 339 | 1 |
| A750 | H | H | 4-OMe | 3-OH | 311 | 1 |
| A751 | H | H | 3-OMe | 3,5-di-Cl-4-OH | 379/381/383 | 1 |
| A752 | H | H | 3-OMe | 3,5-di-Br-4-OH | 467/469/471 | 1 |
| A753 | H | H | 3-OMe | 3-CO2H-4-Cl | 373/375 | 1 |
| A754 | H | H | 3-OMe | 3-CO2H | 339 | 1 |
| A755 | H | H | 3-OMe | 3-OH | 311 | 1 |
| A756 | H | H | 3-NO2 | 4-CH2NH2 | 337 [M − H]− | 10 |
| A757 | H | H | 2-OMe | 4-CH2NH2 | 322 [M − H]− | 10 |
| A758 | H | H | 3-Me | 3,4-[S—CH=N] | 336 | 1 |
| A759 | H | H | 3-OMe | 3,4-[S—CH=N] | 352 | 1 |
| A760 | H | H | 4-OH | 3-CO2H-4-Cl | 359/361 | 4 |
| A761 | H | H | 4-NMe2 | 4-SMe | 354 | 1 |
| A762 | H | H | 4-Cl | 3-OH-4-OMe | 345/347 | 1 |
| A763 | H | H | 3-NO2 | 4-(CH2)2CO2H | 380 [M − H] | 1 |
| A764 | H | H | 3-NO2 | 4-(CH2)2CO2Me | 396 | 1 |
| A765 | H | H | 4-Cl | 4-(CH2)2CO2Me | 385/387 | 1 |
| A766 | H | H | 2-OMe | 4-(CH2)2CO2H | 367 | 1 |
| A767 | H | H | 2-OMe | 4-(CH2)2CO2Me | 381 | 1 |
| A768 | H | H | 4-Cl | 3,5-di-Cl-4-Me | 381/383/385/387 | 1 |
| A769 | H | H | 4-Cl | 4-trans-CH=CHCO2Et | 397/399 | 1 |
| A770 | H | H | 4-CO2Me | 3-F-4-Me | 355 | 11 |
| A771 | H | Me | 4-Cl | 2-Me | 327/329 | 1 |
| A772 | H | H | 3-NO2 | 4-[(CH2)2CONH(CH2)6—NHCOMe] | 522 | 12 |
| A773 | H | H | 4-Cl | 4-[(CH2)2CONH(CH2)6—NHCOMe] | 511/643 | 12 |
| A774 | H | H | 2-OMe | 4-[(CH2)2CONH(CH2)6—NHCOMe] | 507 | 12 |
| A775 | H | H | 3,5-di-Me | 3,5-di-Cl-4-OH | 377/379/381 | 1 |
| A776 | H | H | 3,5-di-Me | 3,5-di-Br-4-OH | 465/467/469 | 1 |
| A777 | H | H | 3,5-di-Me | 3-CO2H-4-Cl | 371/373 | 1 |
| A778 | H | H | 3,5-di-Me | 3-CO2H | 337 | 1 |
| A779 | H | H | 3,5-di-Me | 3-OMe | 323 | 1 |
| A780 | H | H | 3,5-di-Me | 3,4-[OCH2O] | 337 | 1 |
| A781 | H | H | 4-iPr | 3,5-di-Cl-4-OH | 391/393/395 | 1 |
| A782 | H | H | 4-iPr | 3,5-di-Br-4-OH | 479/481/483 | 1 |
| A783 | H | H | 4-iPr | 3-CO2H-4-Cl | 385/387 | 1 |
| A784 | H | H | 4-iPr | 3-CO2H | 351 | 1 |
| A785 | H | H | 4-iPr | 3-OMe | 337 | 1 |
| A786 | H | H | 4-iPr | 3,4-[OCH2O] | 351 | 1 |
| A787 | H | H | 2-Br | 3,5-di-Cl-4-OH | 427/429/431/433 | 1 |
| A788 | H | H | 2-Br | 3,5-di-Br-4-OH | 515/517/519/521 | 1 |
| A789 | H | H | 2-Br | 3-CO2H | 387/389 | 1 |
| A790 | H | H | 2-Br | 3-OMe | 373/375 | 1 |
| A791 | H | H | 2-Br | 3,4-[OCH2O] | 387/389 | 1 |
| A792 | H | H | 3,4-di-OMe | 3-OMe | 355 | 1 |
| A793 | H | H | 3-Cl-4-OMe | 3,5-di-Cl-4-OH | 413/415/417/419 | 1 |
| A794 | H | H | 3-Cl-4-OMe | 3,5-di-Br-4-OH | 501/503/505/507 | 1 |
| A795 | H | H | 3-Cl-4-OMe | 3-CO2H-4-Cl | 407/409/411 | 1 |
| A796 | H | H | 3-Cl-4-OMe | 3-CO2H | 371/373 [M − H]− | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

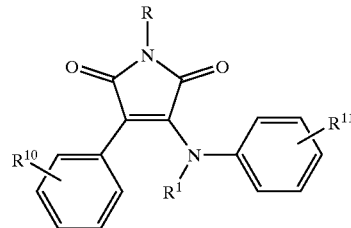

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A797 | H | H | 3-Cl-4-OMe | 3-OMe | 359/361 | 1 |
| A798 | H | H | 4-Me | 3,5-di-Cl-4-OH | 363/365/367 | 1 |
| A799 | H | H | 4-Me | 3,5-di-Br-4-OH | 451/453/455 | 1 |
| A800 | H | H | 4-Me | 3-CO2H | 323 | 1 |
| A801 | H | H | 4-Me | 3-OMe | 309 | 1 |
| A802 | H | H | 4-Me | 3,4-[OCH2O] | 323 | 1 |
| A803 | H | H | 2,4-di-Cl | 3,5-di-Cl-4-OH | 415/417/419/421/423 [M − H]− | 1 |
| A804 | H | H | 2,4.di-Cl | 3,5-di-Br-4-OH | 503/505/507/509/511 [M − H]− | 1 |
| A805 | H | H | 2,4-di-Cl | 3-CO2H | 377/379/381 | 1 |
| A806 | H | H | 2,4-di-Cl | 3-OMe | 363/365/367 | 1 |
| A807 | H | H | 2,4-di-Cl | 3,4-[OCH2O] | 375/377/379 [M − H]− | 1 |
| A808 | H | H | 3-Cl | 3,5-di-Cl-4-OH | 381/383/385/387 [M − H]− | 1 |
| A809 | H | H | 3-Cl | 3-CO2H | 343/345 | 1 |
| A810 | H | H | 3-Cl | 3-OMe | 329/331 | 1 |
| A811 | H | H | 3-Cl-4-OMe | 3,4-[OCH2O] | 373/375 | 1 |
| A812 | H | H | 3-Br | 3,5-di-Cl-4-OH | 425/427/429/431 [M − H]− | 1 |
| A813 | H | H | 4-SMe | 3,5-di-Cl-4-OH | 393/395/397 [M − H]− | 1 |
| A814 | H | H | 4-F | 3,5-di-Cl-4-OH | 365/367/369 [M − H]− | 1 |
| A815 | H | H | 3-Cl | 3,4-[OCH2O] | 343/345 | 1 |
| A816 | H | H | 4-Cl | 3,4-[CO(CH2)4] | 381/383 | 1 |
| A817 | H | H | 4-Cl | 3,4-[CH2SO2CH2] | 387/389 [M − H]− | 1 |
| A818 | H | H | 4-Cl | 3,4-[O—C(Me)=N] | 354/356 | 1 |
| A819 | H | H | 4-Cl | 3,4-[OCF2O] | 379/381 | 1 |
| A820 | H | H | 4-Cl | 3,4-[O(CH2)3O] | 371/373 | 1 |
| A821 | H | H | 2,3-di-F | 3,5-di-Cl-4-OH | 383/385/387 [M − H]− | 1 |
| A822 | H | H | 2,6-di-Cl | 3,5-di-Cl-4-OH | 415/417/419/421/423 [M − H]− | 1 |
| A823 | H | H | 3,4-di-Cl | 3,5-di-Cl-4-OH | 415/417/419/421/423 [M − H]− | 1 |
| A824 | H | H | 2-F | 3,5-di-Cl-4-OH | 367/369/371 | 1 |
| A825 | H | H | 2-Me | 3,5-di-Cl-4-OH | 363/365/367 | 1 |
| A826 | H | H | 4-NO2 | 3,5-di-Cl-4-OH | 392/394/396 [M − H]− | 1 |
| A827 | H | H | 3-OPh | 3,5-di-Cl-4-OH | 441/443/445 | 1 |
| A828 | H | H | 4-OPh | 3,5-di-Cl-4-OH | 441/443/445 | 1 |
| A829 | H | H | 3-NO2-4-Cl | 3,5-di-Cl-4-OH | 426/428/430/432 [M − H]− | 1 |
| A830 | H | H | 4-OH | 3-Cl-4-OH | 331/333 | 4 |
| A831 | H | H | 4-OH | 3-Br-4-OH | 375/377 | 4 |
| A832 | H | H | 4-Cl | 4-trans-CH=CHCO2H | 369/371 | 13 |
| A833 | H | H | 4-Cl | 4-trans-CH=CHCONH2 | 368/370 | 14 |
| A834 | H | Me | 4-Cl | 4-OMe | 343/345 | 1 |
| A835 | H | H | 3,4,5-tri-F | 3,5-di-Cl-4-OH | 401/403/405 [M − H]− | 1 |
| A836 | H | H | 2-NO2 | 3,5-di-Cl-4-OH | 392/395/397 [M − H]− | 1 |
| A837 | H | H | 3,5-di-F | 3,5-di-Cl-4-OH | 383/385/387 [M − H]− | 1 |
| A838 | H | H | 4-Cl | 3-[OC6F5] | 481/483 | 1 |
| A839 | H | H | 4-Cl | 2,3-[OCF2O] | 377/379 [M − H]− | 1 |
| A840 | H | H | 2-F | 3,4-[S—CH=N] | 340 | 1 |
| A841 | H | H | 3-F | 3,4-[S—CH=N] | 340 | 1 |
| A842 | H | H | 3-Cl | 3,4-[S—CH=N] | 356/358 | 1 |
| A843 | H | H | 4-CF3 | 3,5-di-Cl-4-OH | 415/417/419 [M − H]− | 1 |
| A844 | H | H | 3-SCF3 | 3,5-di-Cl-4-OH | 447/449/451 [M − H]− | 1 |
| A845 | H | H | 4-OCF3 | 3,5-di-Cl-4-OH | 431/433/435 [M − H]− | 1 |
| A846 | H | H | 3-CF3 | 3,5-di-Cl-4-OH | 415/417/419 [M − H]− | 1 |
| A847 | H | H | 3,5-bis-CF3 | 3,5-di-Cl-4-OH | 483/485/487 [M − H]− | 1 |
| A848 | H | H | 3,4-[OCH2O] | 3,5-di-Cl-4-OH | 393/395/397 | 1 |
| A849 | H | H | 2-OCH2Ph | 3,5-di-Cl-4-OH | 455/457/459 | 1 |
| A850 | H | H | 3,4-[(—CH=CH—)2] | 3,5-di-Cl-4-OH | 399/401/403 | 1 |
| A851 | H | H | 4-Cl | 3,4-[N=C(Me)—O] | 354/356 | 1 |
| A852 | H | H | 4-F | 3,4-[S—CH=N] | 340 | 1 |
| A853 | H | H | 3-Br | 3,4-[S—CH=N] | 400/402 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

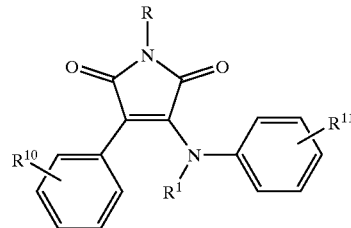

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A854 | H | H | 2-Br | 3,4-[S—CH=N] | 400/402 | 1 |
| A855 | Me | H | 4-Cl | 3-CO2H-4-Cl | 389/391/393 [M − H]− | 1 |
| A856 | Me | H | 4-Cl | 4-CH2SO2NHMe | 420/422 | 1 |
| A857 | Me | H | 4-Cl | 3,5-di-F | 349/351 | 1 |
| A858 | Me | H | 4-Cl | 3,4-[OCH2O] | 357/359 | 1 |
| A859 | Me | H | 4-Cl | 3,5-di-Cl-4-OH | 397/399/401/403 | 1 |
| A860 | Me | H | 4-Cl | 4-(CH2)2CO2Me | 399/401 | 1 |
| A861 | Me | H | 4-Cl | 4-(CH2)2CO2H | 385/387 | 1 |
| A862 | H | H | 4-COPh | 3,5-di-Cl-4-OH | 453/455/457 | 1 |
| A863 | H | H | 3,4-di-F | 4-SMe | 347 | 1 |
| A864 | H | H | 3,4-di-F | 3,4-[(CH2)3] | 341 | 1 |
| A865 | H | H | 2,4-di-Cl | 3,4-[S—CH=N] | 390/392/394 | 1 |
| A866 | H | H | 3,4-di-Cl | 3,4-[S—CH=N] | 390/392/394 | 1 |
| A867 | H | H | 3-F | 3,5-di-F | 317 [M − H]− | 1 |
| A868 | H | H | 3-F | 4-CH2SO2NHMe | 390 | 1 |
| A869 | H | H | 3-F | 4-(CH2)2CO2H | 355 | 1 |
| A870 | H | H | 3-F | 3-OMe | 313 | 1 |
| A871 | H | H | 3-F | 3-Cl | 317/319 | 1 |
| A872 | H | H | 3-F | 3-Cl-4-OMe | 347/349 | 1 |
| A873 | H | H | 3-F | 3-Cl-4-OH | 333/335 | 1 |
| A874 | H | H | 3-F | 4-(CH2)3CO2H | 367 [M − H]− | 1 |
| A875 | H | H | 3-F | 3,5-di-Me | 311 | 1 |
| A876 | H | H | 3-F | 3-Cl-4-Me | 331/333 | 1 |
| A877 | H | H | 3-F | H | 283 | 1 |
| A878 | H | H | 2-Cl | 3-F | 315/317 [M − H]− | 1 |
| A879 | H | H | 2-Cl | 3-OMe | 329/331 | 1 |
| A880 | H | H | 2-Cl | 3-Cl-4-OMe | 363/365/367 | 1 |
| A881 | H | H | 2-Cl | 3-Cl-4-OH | 349/351/353 | 1 |
| A882 | H | H | 2-Cl | 4-(CH2)3CO2H | 385/387 | 1 |
| A883 | H | H | 2-Cl | 3,5-di-OMe | 359/361 | 1 |
| A884 | H | H | 2-Cl | 3-NO2-4-OH | 360/362 | 1 |
| A885 | H | H | 2-Cl | 4-CH2P(O)(OEt)2 | 449/451 | 1 |
| A886 | H | H | 2-Cl | 4-NHCOMe | 356/358 | 1 |
| A887 | H | H | 2-Cl | 4-(CH2)2CONH2 | 370/372 | 1 |
| A888 | H | H | 2-Cl | 3-CH2OH | 329/331 | 1 |
| A889 | H | H | 4-Cl | 3-Cl-4-OMe | 363/365/367 | 1 |
| A890 | H | H | 4-Cl | 3-Cl-4-OH | 349/351/353 | 1 |
| A891 | H | H | 4-Cl | 3-CN | 322/324 [M − H]− | 1 |
| A892 | H | H | 4-Cl | 3-CO2Me | 357/359 | 1 |
| A893 | H | H | 4-Cl | 2-Me-5-CO2Me | 371/373 | 1 |
| A894 | H | H | 4-Cl | 3-Cl-4-Me | 347/349/351 | 1 |
| A895 | H | H | 3,4-di-F | 3-CO2Me | 359 | 1 |
| A896 | H | H | 3,4-di-F | 3-CO2H | 343 [M − H]− | 1 |
| A897 | H | H | 4-Cl | 2,3-[S—CH=N] | 356/358 | 1 |
| A898 | H | H | 4-Cl | 3,4-[N=CH—S] | 356/358 | 1 |
| A899 | H | H | 4-Cl | 3,4-[(CH2)2N(COMe)] | 380/382 [M − H]− | 1 |
| A900 | H | H | 4-Cl | 3,4-[N(COMe)(CH2)2] | 380/382 [M − H]− | 1 |
| A901 | H | H | 3,4-di-F | 3,4-[S—CH=N] | 358 | 1 |
| A902 | H | H | 4-Cl | 3,4-[CH=CHCO—O] | 367/369 | 1 |
| A903 | H | H | 2-Cl | 4-CH2NHCONHPh | 445/447 [M − H]− | 1 |
| A904 | H | H | 4-Cl | 4-OCH2CO2Me | 385/387 [M − H]− | 1 |
| A905 | H | H | 2-Cl | 4-(CH2)2CO2H | 371/373 | 1 |
| A906 | H | H | 2,6-di-Cl | 3,4-[S—CH=N] | 390/392/394 | 1 |
| A907 | H | H | 3-Cl | 3-CO2H-4-Cl | 377/379/381 | 1 |
| A908 | H | H | 3-Cl | 3-Cl-4-OH | 349/351/353 | 1 |
| A909 | H | H | 3-Cl | 3,5-di-F | 335/337 | 1 |
| A910 | H | H | 3-Cl | 3-CH2OH | 329/331 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

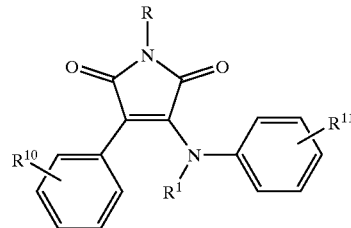

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A911 | H | H | 3-Cl | 3-OH | 315/317 | 1 |
| A912 | H | H | 3-Cl | 4-CH2SO2NHMe | 406/408 | 1 |
| A913 | H | H | 2,4-di-OMe | 3,5-di-Cl-4-OH | 407/409/411 [M − H]− | 13 |
| A914 | H | H | 2-OEt | 3,5-di-Cl-4-OH | 391/393/395 [M − H]− | 13 |
| A915 | H | H | 4-OnBu | 3,5-di-Cl-4-OH | 419/421/423 [M − H]− | 13 |
| A916 | H | H | 3,4,5-tri-OMe | 3,5-di-Cl-4-OH | 439/441/443 | 13 |
| A917 | H | H | 2-OPh | 3,5-di-Cl-4-OH | 441/443/445 | 13 |
| A918 | H | H | 4-Ph | 3,5-di-Cl-4-OH | 425/427/429 | 13 |
| A919 | H | H | 2-OMe-5-Br | 3,5-di-Cl-4-OH | 457/459/461 | 13 |
| A920 | H | H | 4-Cl | 4-CH2NHCONHPh | 445/447 [M − H] | 1 |
| A921 | H | H | 4-Cl | 3-CO2Me-4-Cl | 391/393/395 | 1 |
| A922 | H | H | 2,3-di-F | 3-CO2H-4-Cl | 379/381 | 1 |
| A923 | H | H | 3,4,5-tri-F | 3-CO2H-4-Cl | 395/397 [M − H]− | 1 |
| A924 | H | H | 3,5-di-F | 3-CO2H-4-Cl | 377/379 [M − H]− | 1 |
| A925 | H | H | 2-NO2 | 3-CO2H-4-Cl | 388/390 | 1 |
| A926 | H | H | 3,4-di-F | 3-CO2H-4-Cl | 377/379 [M − H]− | 1 |
| A927 | H | H | 2,3-di-F | 3,4-[OCH2O] | 345 | 1 |
| A928 | H | H | 3,4,5-tri-F | 3,4-[OCH2O] | 363 | 1 |
| A929 | H | H | 2,3-di-F | 3,5-di-F | 337 | 22 |
| A930 | H | H | 2-F | 3-CH2OH | 313 | 1 |
| A931 | H | H | 2,3-di-F | 3-CH2OH | 331 | 1 |
| A932 | H | H | 3,4,5-tri-F | 3-CH2OH | 349 | 1 |
| A933 | H | H | 3,5-di-F | 3-CH2OH | 331 | 1 |
| A934 | H | H | 2-NO2 | 3-CH2OH | 338 [M − H]− | 1 |
| A935 | H | H | 3,4-di-F | 3-CH2OH | 331 | 1 |
| A936 | H | H | 2-OPh | 3-CH2OH | 387 | 1 |
| A937 | H | H | 2,4-di-Cl | 3-CH2OH | 363/365/367 | 1 |
| A938 | H | H | 2,3-di-F | 3-OH | 317 | 1 |
| A939 | H | H | 3,5-di-F | 3-OH | 317 | 1 |
| A940 | H | H | 2,3-[(—CH=CH—)2] | 3,5-di-Cl-4-OH | 399/401/403 | 13 |
| A941 | H | H | 4-Cl | 4-SCH2CO2H | 389/391 | 13 |
| A942 | H | H | 4-Cl | 3,4-[O(CH2)2O] | 357/359 | 1 |
| A943 | H | H | 3,4-di-Cl | 3-CO2H-4-Cl | 409/411/413/415 [M − H]− | 1 |
| A944 | H | H | 3,4-di-Cl | 3-Cl-4-OH | 383/385/387/389 | 1 |
| A945 | H | H | 3,4-di-Cl | 3,5-di-F | 367/369/371 [M − H]− | 1 |
| A946 | H | H | 3,4-di-Cl | 3-CH2OH | 363/365/367 | 1 |
| A947 | H | H | 3,4-di-Cl | 3-OH | 349/351/353 | 1 |
| A948 | H | H | 3,4-di-Cl | 4-CH2SO2NHMe | 438/440/442 [M − H]− | 1 |
| A949 | H | H | 4-SO2Me | 3-CO2H-4-Cl | 419/421 [M − H]− | 1 |
| A950 | H | H | 4-SO2Me | 3,4-[OCH2O] | 386 [M]− | 1 |
| A951 | H | H | 4-SO2Me | 3-Cl-4-OH | 391/393 [M − H]− | 1 |
| A952 | H | H | 4-SO2Me | 3,5-di-F | 379 | 1 |
| A953 | H | H | 2-OMe-5-Br | 3-CO2H-4-Cl | 451/453/455 | 1 |
| A954 | H | H | 2-OMe-5-Br | 3,4-[OCH2O] | 417/419 | 1 |
| A955 | H | H | 2-OMe-5-Br | 3-Cl-4-OH | 423/425/427 | 1 |
| A956 | H | H | 2-OMe-5-Br | 3,5-di-F | 409/411 | 1 |
| A957 | H | H | 2-OMe-5-Br | 3-CH2OH | 403/405 | 1 |
| A958 | H | H | 2-OMe-5-Br | 3-OH | 389/391 | 1 |
| A959 | H | H | 2-Me | 3,4-[OCH2O] | 323 | 1 |
| A960 | H | H | 2-Me | 3-Cl-4-OH | 329/331 | 1 |
| A961 | H | H | 2-Me | 3-CH2OH | 309 | 1 |
| A962 | H | H | 2-Me | 3-OH | 295 | 1 |
| A963 | H | H | 3-Br | 3-CO2H-4-Cl | 419/421/423 [M − H]− | 1 |
| A964 | H | H | 3-Br | 3,4-[OCH2O] | 387/389 | 1 |
| A965 | H | H | 3-Br | 3-Cl-4-OH | 393/395/397 | 1 |
| A966 | H | H | 3-Br | 3,5-di-F | 379/381 | 1 |
| A967 | H | H | 4-Cl | 4-trans-CH=CHPh | 401/403 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

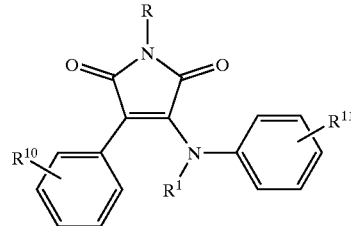

(XXX-1)

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A968 | H | H | 4-Cl | 4-SCH2CONH(CH2)2OMe | 446/448 | 17 |
| A969 | H | H | 2-F | 3-CO2H-4-Cl | 361/363 | 1 |
| A970 | H | H | 2,4-di-Cl | 3-CO2H-4-Cl | 411/413/415/417 | 1 |
| A971 | H | H | 2-F | 3,4-[OCH2O] | 327 | 1 |
| A972 | H | H | 3,5-di-F | 3,4-[OCH2O] | 345 | 1 |
| A973 | H | H | 2-NO2 | 3,4-[OCH2O] | 354 | 1 |
| A974 | H | H | 3,4-di-F | 3,4-[OCH2O] | 345 | 1 |
| A975 | H | H | 2-OPh | 3,4-[OCH2O] | 401 | 1 |
| A976 | H | H | 3,4-di-Cl | 3,4-[OCH2O] | 377/379/381 | 1 |
| A977 | H | H | 2-F | 3-Cl-4-OH | 333/335 | 1 |
| A978 | H | H | 2,3-di-F | 3-Cl-4-OH | 351/353 | 1 |
| A979 | H | H | 3,4,5-tri-F | 3-Cl-4-OH | 369/371 | 1 |
| A980 | H | H | 3,5-di-F | 3-Cl-4-OH | 351/353 | 1 |
| A981 | H | H | 2-NO2 | 3-Cl-4-OH | 360/362 | 1 |
| A982 | H | H | 3,4-di-F | 3-Cl-4-OH | 351/353 | 1 |
| A983 | H | H | 2-OPh | 3-Cl-4-OH | 407/409 | 1 |
| A984 | H | H | 2,4-di-Cl | 3-Cl-4-OH | 383/385/387/389 | 1 |
| A985 | H | H | 2-F | 3,5-di-F | 319 | 1 |
| A986 | H | H | 3,4,5-tri-F | 3,5-di-F | 353 [M − H]− | 1 |
| A987 | H | H | 3,5-di-F | 3,5-di-F | 335 [M − H]− | 1 |
| A988 | H | H | 3,4-di-F | 3,5-di-F | 335 [M − H]− | 1 |
| A989 | H | H | 2-F | 3-OH | 299 | 1 |
| A990 | H | H | 3,4,5-tri-F | 3-OH | 335 | 1 |
| A991 | H | H | 2-NO2 | 3-OH | 326 | 1 |
| A992 | H | H | 3,4-di-F | 3-OH | 317 | 1 |
| A993 | H | H | 2-OPh | 3-OH | 373 | 1 |
| A994 | H | H | 2,4-di-Cl | 3-OH | 349/351/352 | 1 |
| A995 | H | H | 4-Br | 4-SO2NH2 | 420/422 [M − H]− | 3 |
| A996 | H | H | 4-Cl | 3-SO2NHnBu | 434/436 | 1 |
| A997 | H | H | 4-Cl | 2,3-[N=CH—CH=CH] | 350/352 | 13 |
| A998 | H | H | 2-OEt | 3-Cl | 343/345 | 1 |
| A999 | H | H | 2-OPh | 3-Cl | 391/393 | 1 |
| A1000 | H | H | 2-OMe-5-Br | 3-Cl | 405/407/409 [M − H]− | 1 |
| A1001 | H | H | 3-F | 3-SO2NHnBu | 418 | 1 |
| A1002 | H | H | 4-Cl | 2-Me-5-CO2H | 355/357 [M − H]− | 13 |
| A1003 | H | H | 2-Cl | 3-CH2CO2H | 357/359 | 13 |
| A1004 | H | H | 4-Cl | 2-OH-5-CO2H | 359/361 | 13 |
| A1005 | H | H | 2-F-6-Cl | H | 317/319 | 1 |
| A1006 | H | H | 2-F-6-Cl | 3-Br | 395/397/399 | 1 |
| A1007 | H | H | 2-F-6-Cl | 4-SMe | 363/365 | 1 |
| A1008 | H | H | 2-F-6-Cl | 4-Me | 331/333 | 1 |
| A1009 | H | H | 2-F-6-Cl | 3,4-[OCH2O] | 361/363 | 1 |
| A1010 | H | H | 2-F-6-Cl | 3,4-[(CH2)3] | 357/359 | 1 |
| A1011 | H | H | 2-F-6-Cl | 4-CH2SO2NHMe | 424/426 | 1 |
| A1012 | H | H | 4-I | H | 391 | 1 |
| A1013 | H | H | 3-F | 2-Me | 297 | 1 |
| A1014 | H | H | 3-F | 3-Me | 297 | 1 |
| A1015 | H | H | 3-F | 3-CH2OH | 313 | 1 |
| A1016 | H | H | 3-F | 3-F | 301 | 1 |
| A1017 | H | H | 3-F | 3,5-di-OMe | 343 | 1 |
| A1018 | H | H | 3-F | 3,5-di-Br-4-Me | 453/455/457 | 1 |
| A1019 | H | H | 3-F | 4-CH2P(O)(OEt)2 | 433 | 1 |
| A1020 | H | H | 3-F | 4-F | 301 | 1 |
| A1021 | H | H | 3-F | 4-OMe | 313 | 1 |
| A1022 | H | H | 3-F | 4-CH2NHCOPh | 416 | 13 |
| A1023 | H | H | 3-F | 4-CH2NHCOMe | 354 | 13 |
| A1024 | H | H | 4-Cl | 4-CH2NHCOMe | 368/370 [M − H]− | 13 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

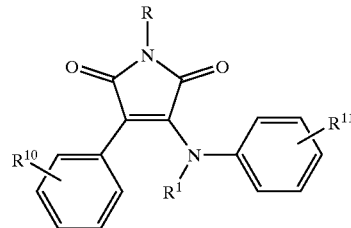

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A1025 | H | H | 2,6-di-F | 3,5-di-Cl-4-OH | 385/387/389 | 13 |
| A1026 | H | H | 4-I | 4-CH2SO2NHMe | 498 | 1 |
| A1027 | H | H | 2,5-di-Me | 3,5-di-Cl-4-OH | 375/377/379 [M − H]− | 13 |
| A1028 | H | H | 2-F-6-Cl | 3,5-di-Cl-4-OH | 399/401/403/405 [M − H]− | 13 |
| A1029 | H | H | 2-OCF3 | 3,5-di-Cl-4-OH | 431/433/435 [M − H]− | 13 |
| A1030 | H | H | 3-F | 3-CN | 306 [M − H]− | 1 |
| A1031 | H | H | 3-F | 3,4-di-Cl | 351/353/355 | 1 |
| A1032 | H | H | 4-I | 4-Me | 403 [M − H]− | 1 |
| A1033 | H | H | 4-I | 3-[trans-CH=CHCONMe2]-4-Cl | 522/524 | 1 |
| A1034 | H | H | 3-F | 3-[trans-CH=CHCONMe2]-4-Cl | 412/414 [M − H]− | 1 |
| A1035 | H | H | 3-F | 2-F | 301 | 1 |
| A1036 | H | H | 3-F | 2-Me-5-Cl | 331/333 | 1 |
| A1037 | H | H | 3-F | 2-Me-4-OMe | 327 | 1 |
| A1038 | H | H | 3-F | 3-COPh | 387 | 1 |
| A1039 | H | H | 3-F | 3-COMe | 325 | 1 |
| A1040 | H | H | 3-F | 4-(CH2)2CONH2 | 354 | 1 |
| A1041 | H | H | 2,6-di-F | 3-Cl | 335/337 | 1 |
| A1042 | H | H | 2-F-6-Cl | 3-Cl | 351/353/355 | 1 |
| A1043 | H | H | 2,5-di-F | 3-Cl | 335/337 | 1 |
| A1044 | H | H | 2,5-di-Me | 3-Cl | 327/329 | 1 |
| A1045 | H | H | 2-I | 3-Cl | 425/427 | 1 |
| A1046 | H | H | 2-OCF3 | 3-Cl | 383/385 | 1 |
| A1047 | H | H | 2-F-6-Cl | 4-(CH2)2CONH2 | 388/390 | 1 |
| A1048 | H | H | 4-I | 3,5-di-Cl | 457/459/461 [M − H]− | 1 |
| A1049 | H | H | 4-I | 4-(CH2)2CONH2 | 462 | 1 |
| A1050 | H | H | 3-F | 4-OPh | 375 | 1 |
| A1051 | H | H | 4-I | 3,5-di-Cl-4-OH | 347/349/351 [M − I]− | 13 |
| A1052 | H | H | 3-F | 4-(CH2)2NHCOPh | 430 | 13 |
| A1053 | H | H | 3-F | 3-[4-Methylpiperazin-1-yl]-4-OMe | 411 | 20 |
| A1054 | H | H | 3-F | 3,5-di-Cl-4-Me | 363/365/367 [M − H]− | 1 |
| A1055 | H | H | 2,3-di-F | 3,5-di-Cl-4-Me | 383/385/387 | 1 |
| A1056 | H | H | 4-Br | 3,5-di-Cl-4-Me | 425/427/429/431 | 1 |
| A1057 | H | H | 2,5-di-F | 3-Br | 379/381 | 1 |
| A1058 | H | H | 2-OCF3 | 3-Br | 427/429 | 1 |
| A1059 | H | H | 2,5-di-Me | 4-Me | 307 | 1 |
| A1060 | H | H | 2-I | 4-Me | 405 | 1 |
| A1061 | H | H | 2-OCF3 | 4-Me | 363 | 1 |
| A1062 | H | H | 4-I | 3,5-di-Cl-4-Me | 473/475/477 | 1 |
| A1063 | H | H | 2-Cl | 3,5-di-Cl-4-Me | 381/383/385/387 | 1 |
| A1064 | H | H | 3-Me | 3,5-di-Cl-4-Me | 361/363/365 | 1 |
| A1065 | H | H | 2,4-di-Cl | 3,5-di-Cl-4-Me | 415/417/419/421/423 | 1 |
| A1066 | H | H | 2-I | 3-Br | 469/471 | 1 |
| A1067 | H | H | 2,6-di-F | 3-Br | 379/381 | 1 |
| A1068 | H | H | 2,5-di-F | 4-SMe | 347 | 1 |
| A1069 | H | H | 2,5-di-Me | 4-SMe | 339 | 1 |
| A1070 | H | H | 2-I | 4-SMe | 437 | 1 |
| A1071 | H | H | 2-OCF3 | 4-SMe | 395 | 1 |
| A1072 | H | H | 2,6-di-F | 4-SMe | 347 | 1 |
| A1073 | H | H | 2,5-di-F | 4-Me | 315 | 1 |
| A1074 | H | H | 2,6-di-F | 4-Me | 315 | 1 |
| A1075 | H | H | 2,5-di-F | 3,4-[OCH2O] | 345 | 1 |
| A1076 | H | H | 2,5-di-Me | 3,4-[OCH2O] | 337 | 1 |
| A1077 | H | H | 2-I | 3,4-[OCH2O] | 435 | 1 |
| A1078 | H | H | 2-OCF3 | 3,4-[OCH2O] | 393 | 1 |
| A1079 | H | H | 2,5-di-F | 3,4-[(CH2)3] | 341 | 1 |
| A1080 | H | H | 2,5-di-Me | 3,4-[(CH2)3] | 333 | 1 |
| A1081 | H | H | 2-I | 3,4-[(CH2)3] | 431 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

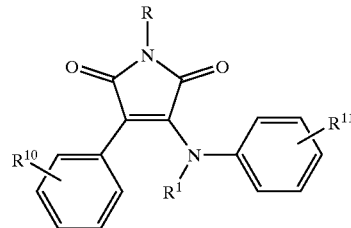

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A1082 | H | H | 2-OCF3 | 3,4-[(CH2)3] | 389 | 1 |
| A1083 | H | H | 2,6-di-F | 3,4-[(CH2)3] | 341 | 1 |
| A1084 | H | H | 2-OCF3 | 4-(CH2)2CONH2 | 420 | 1 |
| A1085 | H | H | 2,5-di-F | H | 301 | 1 |
| A1086 | H | H | 2,5-di-Me | H | 293 | 1 |
| A1087 | H | H | 2-I | H | 391 | 1 |
| A1088 | H | H | 2-OCF3 | H | 349 | 1 |
| A1089 | H | H | 2,6-di-F | H | 301 | 1 |
| A1090 | H | H | 2,3-di-F | 3-CH2CONH2 | 358 | 1 |
| A1091 | H | H | 2,3-di-F | 3-CH2CONHMe | 372 | 1 |
| A1092 | H | H | 2,3-di-F | 3-CONHMe | 358 | 1 |
| A1093 | H | H | 2,3-di-F | 3-CONH2-4-Me | 358 | 1 |
| A1094 | H | H | 2,3-di-F | 3-CONH(CH2)2OMe | 402 | 1 |
| A1095 | H | H | 3-F | 3-CH2CONH2 | 340 | 1 |
| A1096 | H | H | 3-F | 3-CH2CONHMe | 354 | 1 |
| A1097 | H | H | 3-F | 3-CONHMe | 340 | 1 |
| A1098 | H | H | 3-F | 3-CONH2-4-Me | 340 | 1 |
| A1099 | H | H | 3-F | 3-CONH(CH2)2OMe | 384 | 1 |
| A1100 | H | H | 3-F | 3-CF3 | 351 | 1 |
| A1101 | H | H | 3-F | 4-nBu | 339 | 1 |
| A1102 | H | H | 3-F | 4-OnBu | 355 | 1 |
| A1103 | H | H | 3-F | 2-Et | 311 | 1 |
| A1104 | H | H | 3-F | 2-iPr | 325 | 1 |
| A1105 | H | H | 3-F | 3,4-[OCF2O] | 363 | 1 |
| A1106 | H | H | 3-F | 3,4-[(CH2)2N(COMe)] | 366 | 1 |
| A1107 | H | H | 3-F | 3,4-[O(CH2)3O] | 355 | 1 |
| A1108 | H | H | 3-F | 3,4-di-Me | 311 | 1 |
| A1109 | H | H | 3-F | 3,4-di-OMe | 343 | 1 |
| A1110 | H | H | 3-F | 3-Br-4-OCF3 | 445/447 | 1 |
| A1111 | H | H | 3-F | 3-CO2Me | 341 | 1 |
| A1112 | H | H | 3-F | 3-CONH2 | 326 | 1 |
| A1113 | H | H | 3-F | 3-F-4-Me | 315 | 1 |
| A1114 | H | H | 3-F | 3-I | 409 | 1 |
| A1115 | H | H | 3-F | 3-OCH2Ph | 389 | 1 |
| A1116 | H | H | 3-F | 4-CH2NHBOC | 410 $[M - H]^-$ | 1 |
| A1117 | H | H | 3-F | 4-Cl | 317/319 | 1 |
| A1118 | H | H | 3-F | 4-NHCOMe | 340 | 1 |
| A1119 | H | H | 3-F | 4-OCH2Ph | 389 | 1 |
| A1120 | H | H | 3-F | 4-tBu | 339 | 1 |
| A1121 | H | H | 3-F | 2,3-[OCF2O] | 363 | 1 |
| A1122 | H | H | 3-F | 2-Me-3-Br | 375/377 | 1 |
| A1123 | H | H | 3-F | 2-Me-3-Cl | 331/333 | 1 |
| A1124 | H | H | 3-F | 2-Me-5-CH2OH | 325 $[M - H]^-$ | 1 |
| A1125 | H | H | 3-F | 2-OPh | 375 | 1 |
| A1126 | H | H | 3-F | 3,4-[CH2SO2CH2] | 373 | 1 |
| A1127 | H | H | 3-F | 3-Br-4-Cl | 395/397/399 | 1 |
| A1128 | H | H | 3-F | 3-OiPr | 341 | 1 |
| A1129 | H | H | 3-F | 3-SO2CF3 | 413 $[M - H]^-$ | 1 |
| A1130 | H | H | 3-F | 2,3-di-Me | 311 | 1 |
| A1131 | H | H | 3-F | 2,4-di-Me | 311 | 1 |
| A1132 | H | H | 3-F | 2-Me-4-Cl | 331/333 | 1 |
| A1133 | H | H | 3-F | 2-OMe | 313 | 1 |
| A1134 | H | H | 3-F | 2-Ph | 359 | 1 |
| A1135 | H | H | 3-F | 2-SMe | 329 | 1 |
| A1136 | H | H | 3-F | 3-Et | 311 | 1 |
| A1137 | H | H | 2,5-di-Me | 4-(CH2)2CONH2 | 364 | 1 |
| A1138 | H | H | 2,5-di-F | 4-(CH2)2CONH2 | 372 | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

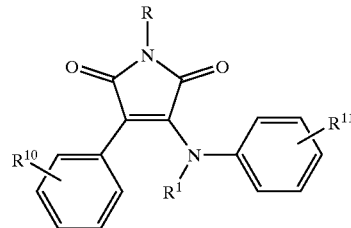

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A1139 | H | H | 2-I | 4-(CH2)2CONH2 | 462 | 1 |
| A1140 | H | H | 2,6-di-F | 4-(CH2)2CONH2 | 372 | 1 |
| A1141 | H | H | 2,6-di-F | 3,4-[OCH2O] | 345 | 1 |
| A1142 | H | H | 3,5-di-F | 3,5-di-Cl-4-Me | 383/385/387 | 1 |
| A1143 | H | H | 2,5-di-F | 4-CH2SO2NHMe | 408 | 1 |
| A1144 | H | H | 2,5-di-Me | 4-CH2SO2NHMe | 400 | 1 |
| A1145 | H | H | 2-I | 4-CH2SO2NHMe | 498 | 1 |
| A1146 | H | H | 2-OCF3 | 4-CH2SO2NHMe | 456 | 1 |
| A1147 | H | H | 2,6-di-F | 4-CH2SO2NHMe | 408 | 1 |
| A1148 | H | H | 4-Cl | 4-CH2NHCOPh | 432/434 | 13 |
| A1149 | H | H | 2,3-di-F | 3,4-[S—CH=N] | 358 | 1 |
| A1150 | H | H | 4-Cl | 4-trans-CH=CH-(4-OH—Ph) | 417/419 | 1 |
| A1151 | H | H | 4-I | 4-Cl | 425/427 | 1 |
| A1152 | H | H | 4-I | 4-OMe | 421 | 1 |
| A1153 | H | H | 3-F | 4-trans-CH=CHCONH2 | 352 | 13 |
| A1154 | H | H | 2,3-di-F | 4-trans-CH=CHCONH2 | 370 | 13 |
| A1155 | H | H | 3-F | 3-[4-(COCHCl2)-Piperazin-1-yl]-4-OMe | 507/509/511 | 13 |
| A1156 | H | H | 3-F | 4-trans-CH=CH-(4-OH—Ph) | 401 | 1 |
| A1157 | H | H | 3-F | 4-[1,2,3-Thiadiazol-4-yl] | 367 | 1 |
| A1158 | H | H | 3-F | 3-[O-(Pyrimidin-2-yl)] | 377 | 13 |
| A1159 | H | H | 3-F | 4-[N(Me)(Pyrimidin-2-yl)] | 390 | 20 |
| A1160 | H | H | 3-F | 3,4-[S—C(Me)=N] | 354 | 1 |
| A1161 | H | H | 3-F | 3,4-[O—C(NHMe)=N] | 353 | 1 |
| A1162 | H | H | 2,3-di-F | 4-[Morpholin-1-yl] | 386 | 1 |
| A1163 | H | H | 2,3-di-F | 3,4-[OC(NHMe)=N] | 371 | 13 |
| A1164 | H | H | 3-F | 3,4-[OC(=O)NH] | 340 | 13 |
| A1165 | H | H | 3-F | 3-(CH2OH)-4-OMe | 341 [M − H]− | 13 |
| A1166 | H | H | 3-F | 3-(CH2NMe2)-4-OMe | 370 | 13 |
| A1167 | H | H | 2,3-di-F | 3-Cl | 335/337 | 1 |
| A1168 | H | (CH2)2OH | 2,3-di-F | H | 345 | 1 |
| A1169 | H | H | 2,3-di-F | 4-CH2SO2NHMe | 408 | 1 |
| A1170 | H | H | 2,3-di-F | 3-CH2CO2H | 359 | 13 |
| A1171 | H | H | 2,3-di-F | 4-CH2CO2H | 359 | 13 |
| A1172 | H | H | 2,3-di-F | 4-OCH2CO2H | 375 | 13 |
| A1173 | H | H | 2,3-di-F | 4-(CH2)2CO2H | 373 | 13 |
| A1174 | H | H | 2,3-di-F | 4-(CH2)3CO2H | 385 [M − H]− | 13 |
| A1175 | H | H | 2,3-di-F | 4-NMe2 | 344 | 1 |
| A1176 | H | H | 2,3-di-F | 2,4-di-F | 337 | 1 |
| A1177 | H | H | 2,3-di-F | 3,4-di-F | 337 | 1 |
| A1178 | H | H | 2,3-di-F | 2,3-di-F | 337 | 1 |
| A1179 | H | H | 2,3-di-F | 2,5-di-F | 337 | 1 |
| A1180 | H | H | 2,3-di-F | 4-SPh | 409 | 1 |
| A1181 | H | H | 2,3-di-F | 4-OPh | 393 | 1 |
| A1182 | H | H | 2,3-di-F | 4-NHPh | 392 | 1 |
| A1183 | H | H | 2,3-di-F | 2-OMe-3-F | 349 | 1 |
| A1184 | H | H | 2,3-di-F | 3-Cl-4-Me | 349/351 | 1 |
| A1185 | H | H | 2,3-di-F | 4-NHSO2Me | 394 | 1 |
| A1186 | H | H | 2,3-di-F | 3-[CH2-(1,3-Thiazolidine-2,4-dion-5-yl) | 430 | 1 |
| A1187 | H | H | 3-F | 4-[OCH2-(1-Methyl-piperazine-4-yl)] | 410 | 1 |
| A1188 | H | (CH2)2OH | 2-Cl | H | 343/345 | 3 |
| A1189 | H | (CH2)2OH | 3,5-di-Me | H | 337 | 3 |
| A1190 | H | H | 2,3-di-F | 3,4-[N=N—NH] | 342 | 1 |
| A1191 | H | H | 2,3-di-F | 3,4-[CH=N—NH] | 341 | 1 |
| A1192 | H | H | 2,3-di-F | 3,4-[NH—N=CH] | 341 | 1 |
| A1193 | H | H | 2,3-di-F | 3,4-[OCF2O] | 379 [M − H]− | 1 |
| A1194 | H | H | 2,3-di-F | 3,5-di-Cl | 367/369/371 [M − H]− | 1 |

TABLE A-continued

Encompassing compounds of general formula (XXX-1), wherein group $R^2$ of formula (I) is a phenyl ring, optionally substituted by one or more substituents $R^{10}$ and group $R^3$ of formula (I) is a phenyl ring, optionally substituted by one or more substituents $R^{11}$ and substituents R, $R^1$, $R^{10}$ and $R^{11}$ are listed in Table A.

(XXX-1)

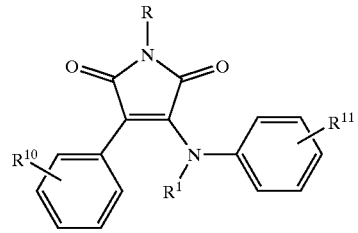

| Example No. | R | $R^1$ | $R^{10}$ | $R^{11}$ | $[M + H]^+$ Observed; (Unless $[M]^-$ or $[M - H]^-$ are Indicated) | For Procedure See Example No. |
|---|---|---|---|---|---|---|
| A1195 | H | H | 2,3-di-F | 3,5-di-Me | 327 [M − H]− | 1 |
| A1196 | H | H | 2,3-di-F | 2-F | 317 [M − H]− | 1 |
| A1197 | H | H | 2,3-di-F | 3-Cl-4-OMe | 363/365 [M − H]− | 1 |
| A1198 | H | H | 2,3-di-F | 3-CO2H | 343 [M − H]− | 1 |
| A1199 | H | H | 2,3-di-F | 3-F | 319 | 1 |
| A1200 | H | H | 2,3-di-F | 3-F-4-Me | 333 | 1 |
| A1201 | H | H | 2,3-di-F | 3-I | 425 [M − H]− | 1 |
| A1202 | H | H | 2,3-di-F | 3-OMe | 329 [M − H]− | 1 |
| A1203 | H | H | 2,3-di-F | 4-CH2CH2CONH2 | 370 [M − H]− | 1 |
| A1204 | H | H | 2,3-di-F | 4-F | 317 [M − H]− | 1 |
| A1205 | H | H | 2,3-di-F | 4-Cl | 333/335 [M − H]− | 1 |
| A1206 | H | H | 2,3-di-F | 4-NHCOMe | 358 | 1 |
| A1207 | H | H | 2,3-di-F | 4-OMe | 331 | 1 |
| A1208 | H | H | 2,3-di-F | 4-CH2CONH2 | 358 | 1 |
| A1209 | H | H | 2,3-di-F | 3-CH2OMe | 343 [M − H]− | 1 |
| A1210 | H | H | 2,3-di-F | 3-CH(OH)Ph | 405 [M − H]− | 1 |
| A1211 | H | H | 3,5-di-Cl | 4-CH2SO2NHMe | 438/440/442 [M − H]− | 1 |
| A1212 | H | H | 3,5-di-Cl | 4-CH2CH2CONH2 | 402/404/406 [M − H]− | 1 |
| A1213 | H | H | 3,5-di-Cl | 3,5-di-F | 367/369/371 [M − H]− | 1 |
| A1214 | H | H | 3,5-di-Cl | 4-Me | 345/347/349 [M − H]− | 1 |
| A1215 | H | H | 3,5-di-Cl | 3-Cl | 365/367/369/371 [M − H]− | 1 |
| A1216 | H | H | 3,5-di-Cl | H | 331/333/335 [M − H]− | 1 |
| A1217 | H | H | 2,3,5-tri-F | 4-CH2SO2NHMe | 424 [M − H]− | 1 |
| A1218 | H | H | 2,3,5-tri-F | 4-CH2CH2CONH2 | 390 | 1 |
| A1219 | H | H | 2,3,5-tri-F | 3,5-di-F | 353 [M − H]− | 1 |
| A1220 | H | H | 2,3,5-tri-F | 4-Me | 333 | 1 |
| A1221 | H | H | 2,3,5-tri-F | 3-Cl | 351/353 [M − H]− | 1 |
| A1222 | H | H | 2,3,5-tri-F | 3,4-[(CH2)3] | 359 | 1 |
| A1223 | H | H | 2,3,5-tri-F | H | 319 | 1 |
| A1224 | H | H | 2,3-di-F | 3,4-[O(CH2)3O] | 373 | 1 |
| A1225 | H | H | 2,3-di-F | 3-F-4-OMe | 349 | 1 |
| A1226 | H | H | 2,3-di-F | 4-(CH2)2OH | 345 | 1 |
| A1227 | H | H | 2,3-di-F | 4-CH2CN | 340 | 1 |
| A1228 | H | H | 3,5-di-Cl | 3,4-[(CH2)3] | 371/373/375 [M − H]− | 1 |
| A1229 | H | H | 2,3-di-F | 3-[CO2H]-4-[CH2CO2H] | 401 | 1 |
| A1230 | H | H | 2,3-di-F | 4-[4-Methyl-piperazin-1-yl] | 399 | 20 |
| A1231 | H | H | 2,3-di-F | 3,4-[O(CH2)2O] | 357 [M − H]− | 1 |
| A1232 | H | H | 2,3-di-F | 4-[CH2CO-Morpholin-1-yl)] | 426 [M − H]− | 1 |
| A1233 | H | H | 2,3-di-F | 4-CH2CONH(CH2)2OMe] | 416 | 1 |
| A1234 | H | H | 3-NO2 | 4-[(CH2)2CONH(CH2)6NHBOC] | 578 [M − H]− | 12 |
| A1235 | H | H | 3-NO2 | 4-[(CH2)2CONH(CH2)6NH2] | 480 | 10 |
| A1236 | H | H | 3-NO2 | 4-[(CH2)2CONH(CH2)6NH-Biotinyl] | 706 | 9 |
| A1237 | H | H | 2,3-di-F | 3-[CH2CH(Me)CO2H] | 385 [M − H]− | 13 |
| A1238 | H | H | 2,3,5-tri-F | 3,5-di-Cl-4-OH | 401/403/405 [M − H]− | 13 |
| A1239 | H | H | 3,5-di-Cl | 3,5-di-Cl-4-OH | 415/417/419/421/423 [M − H]− | 13 |
| A1240 | H | H | 3,5-di-F | 2,3-di-F | 337 | 1 |
| A1241 | H | H | 2,3-di-F | 4-[SCH2CO2H] | 391 | 13 |

TABLE B

Encompassing compounds of general formula (I) and substituents R, $R^1$, $R^2$ and $R^3$ are listed in Table B.

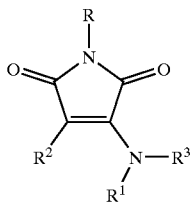

(I)

| Example No. | R | $R^1$ | $R^2$ | $R^3$ | $[M + H]^+$ Observed; (Unless $[M]^-$ or $[M - H]^-$ are Indicated) | For Procedure See Example No. |
|---|---|---|---|---|---|---|
| B1 | Me | Me | Indol-3-yl | Ph | 332 | 3 |
| B2 | H | H | Indol-3-yl | H | 228 | 5 |
| B3 | H | Me | Indol-3-yl | Ph | 318 | 5 |
| B4 | H | H | Ph | H | 189 | 1 |
| B5 | H | H | Ph | CH2Ph | 279 | 1 |
| B6 | CH2Ph | H | Ph | CH2Ph | 369 | 1 |
| B7 | H | Et | 4-CF3-Ph | Et | 313 | 1 |
| B8 | H | Me | 4-OMe-Ph | CH2Ph | 323 | 1 |
| B9 | H | Et | 4-Cl—Ph | Et | 279/281 | 1 |
| B10 | H | Me | 4-Cl—Ph | CH2Ph | 327/329 | 1 |
| B11 | H | Me | 4-Cl—Ph | (CH2)2Ph | 341/343 | 1 |
| B12 | H | Et | Ph | Et | 245 | 1 |
| B13 | H | Me | Ph | CH2Ph | 293 | 1 |
| B14 | H | Me | Ph | (CH2)2Ph | 307 | 1 |
| B15 | H | (CH2)2OMe | 4-Cl—Ph | (CH2)2OMe | 339/341 | 1 |
| B16 | H | H | 3-NO2—Ph | 4-Me-Oxazol-2-yl | 315 | 1 |
| B17 | H | Me | 3-NO2—Ph | CH2Ph | 338 | 1 |
| B18 | H | Me | 3-NO2—Ph | (CH2)2Ph | 352 | 1 |
| B19 | H | H | 3-NO2—Ph | Cyclohexyl | 314 [M − H]- | 1 |
| B20 | H | H | 2-OMe-Ph | Fluoren-2-yl | 383 | 1 |
| B21 | H | H | 3-NO2—Ph | Fluoren-2-yl | 396 [M − H]- | 1 |
| B22 | H | H | 4-Cl—Ph | Dibenzofuran-2-yl | 389/391 | 1 |
| B23 | H | H | 4-Cl—Ph | Dibenzofuran-3-yl | 389/391 | 1 |
| B24 | H | H | 4-Cl—Ph | (2-Acetylbenzofuran-5-yl) | 381/383 | 1 |
| B25 | H | H | 3-NO2—Ph | H | 234 | 16 |
| B26 | H | H | 4-Cl—Ph | 2,6-di-Me-pyridin-3-yl | 328/330 | 13 |
| B27 | H | H | 4-Cl—Ph | (CH2)2OMe | 281/283 | 18 |
| B28 | H | H | 4-I—Ph | (CH2)2OMe | 373 | 18 |
| B29 | H | H | 4-Cl—Ph | 2-Methylpyridin-3-yl | 314/316 | 13 |
| B30 | H | H | 4-Cl—Ph | 2-Chloropyridin-5-yl | 332/334/336 [M − H]- | 13 |
| B31 | H | H | 4-Cl—Ph | Quinolin-3-yl | 350/352 | 13 |
| B32 | H | H | 4-Cl—Ph | Pyrimidin-2-yl | 301/303 | 13 |
| B33 | Me | H | 3-F—Ph | H | 219 [M − H]- | 16 |
| B34 | H | H | 2,3-di-F—Ph | 2,6-di-Me-pyridin-3-yl | 330 | 13 |

TABLE C

Encompassing compounds of general formula (XXX-2), wherein group $R^2$ of formula (I) is a phenyl ring, optionally substituted by one or more substituents $R^{10}$ and the moiety —$NR^1R^3$ of formula (I) represents a heterocyclyl moiety of general formula (XXX-3) and substituents R, $R^{10}$ and P-Q are listed in Table C.

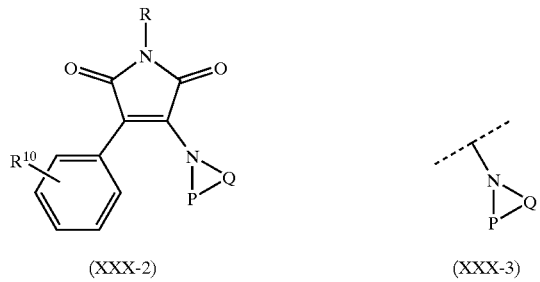

(XXX-2)    (XXX-3)

| Example No. | R | $R^{10}$ | P-Q | $[M + H]^+$ Observed; (Unless $[M]^-$ or $[M - H]^-$ are Indicated) | For Procedure See Example No. |
|---|---|---|---|---|---|
| C1  | H | 4-OMe     | (CH2)2O(CH2)2       | 289 | 1 |
| C2  | H | 4-Cl      | (CH2)4              | 277/279 | 1 |
| C3  | H | 4-Cl      | (CH2)2O(CH2)2       | 293/295 | 1 |
| C4  | H | 4-Cl      | (CH2)3CH(Me)CH2     | 305/307 | 1 |
| C5  | H | 4-Cl      | (CH2)3CH(CONH2)CH2  | 332/334 $[M - H]^-$ | 1 |
| C6  | H | H         | (CH2)3CH(CONH2)CH2  | 300 | 1 |
| C7  | H | 4-OMe     | (CH2)3CH(CONH2)CH2  | 330 | 1 |
| C8  | H | H         | (CH2)4              | 243 | 1 |
| C9  | H | 4-Cl      | (CH2)3CH(CH2OH)CH2  | 321/323 | 1 |
| C10 | H | 4-Cl      | (CH2)5              | 291/293 | 1 |
| C11 | H | 4-Cl      | (CH2)2CH(CH2Ph)(CH2)2 | 381/383 | 1 |
| C12 | H | 4-Cl      | (CH2)2CH(OH)(CH2)2  | 307/309 | 1 |
| C13 | H | 3-NO2     | (CH2)3CH(Me)CH2     | 316 | 1 |
| C14 | H | 2,4-di-Cl | (CH2)5              | 325/327/329 | 1 |
| C15 | H | 2,4-di-Cl | (CH2)2O(CH2)2       | 327/329/331 | 1 |
| C16 | H | 2,4-di-Cl | (CH2)2S(CH2)2       | 341/343/345 $[M - H]^-$ | 1 |

TABLE D

Encompassing compounds of general formula (XXX-4), wherein group $R^2$ of formula (I) is a phenyl ring, optionally substituted by one or more substituents $R^{10}$ and the moiety —$NR^1R^3$ of formula (I) represents a heterocyclyl moiety of general formula (XXX-5), optionally substituted by substituents $R^{12a}$, $R^{12b}$ and $R^{12c}$ and substituents R, $R^{10}$, $R^{12a}$, $R^{12b}$, $R^{12c}$, X-Y and Z are listed in Table D.

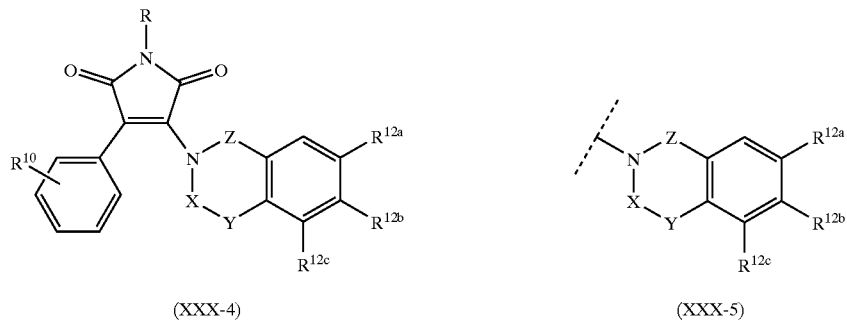

(XXX-4)    (XXX-5)

| Example No. | R | $R^{10}$ | $R^{12a}$ | $R^{12b}$ | $R^{12c}$ | X-Y | Z | $[M + H]^+$ Observed; (Unless $[M]^-$ or $[M - H]^-$ are Indicated) | For Procedure See Example No. |
|---|---|---|---|---|---|---|---|---|---|
| D1 | H | 4-CF3 | H   | H | H | CH=N  | bond | 358 | 2 |
| D2 | H | 4-Cl  | H   | H | H | (CH2)2 | bond | 325/327 | 1 |
| D3 | H | 4-Cl  | H   | H | H | (CH2)2 | CH2  | 339/341 | 1 |
| D4 | H | 4-Cl  | H   | H | H | (CH2)3 | bond | 339/341 | 1 |
| D5 | H | 4-Cl  | NO2 | H | H | (CH2)2 | bond | 370/372 | 1 |
| D6 | H | 3-NO2 | H   | H | H | (CH2)2 | CH2  | 350 | 1 |

TABLE D-continued

Encompassing compounds of general formula (XXX-4), wherein group $R^2$ of formula (I) is a phenyl ring, optionally substituted by one or more substituents $R^{10}$ and the moiety —$NR^1R^3$ of formula (I) represents a heterocyclyl moiety of general formula (XXX-5), optionally substituted by substituents $R^{12a}$, $R^{12b}$ and $R^{12c}$ and substituents R, $R^{10}$, $R^{12a}$, $R^{12b}$, $R^{12c}$;X-Y and Z are listed in Table D.

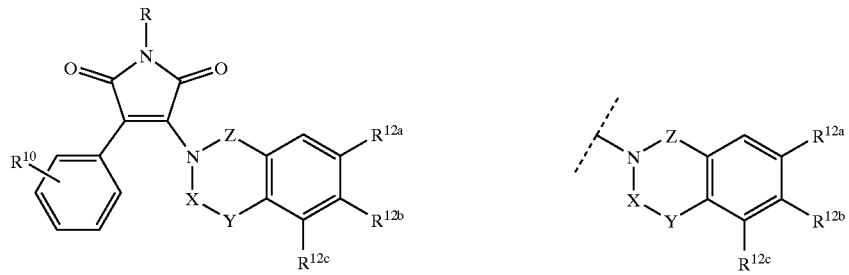

(XXX-4) (XXX-5)

| Example No. | R | $R^{10}$ | $R^{12a}$ | $R^{12b}$ | $R^{12c}$ | X-Y | Z | [M + H]+ Observed; (Unless [M]- or [M − H]- are Indicated) | For Procedure See Example No. |
|---|---|---|---|---|---|---|---|---|---|
| D7 | H | 4-OMe | H | H | H | (CH2)2 | bond | 321 | 1 |
| D8 | H | 4-Cl | H | H | H | (CH2)2 | (CH2)2 | 353/355 | 1 |
| D9 | H | 3-NO2 | H | H | H | (CH2)2 | (CH2)2 | 364 | 1 |
| D10 | H | 3-CF3 | H | H | H | (CH2)2 | bond | 359 | 1 |
| D11 | H | 3,5-di-F | H | H | H | (CH2)2 | bond | 327 | 1 |
| D12 | H | 3-NO2 | H | H | H | (CH2)2 | bond | 336 | 1 |
| D13 | H | 2-OMe | H | H | H | (CH2)2 | bond | 321 | 1 |
| D14 | H | 2-Cl | H | H | H | (CH2)2 | bond | 325/327 | 1 |
| D15 | H | 2-OMe | H | H | H | (CH2)2 | CH2 | 335 | 1 |
| D16 | H | 2-OMe | H | H | H | CH(Me)CH2 | bond | 335 | 1 |
| D17 | H | 2-Cl | H | H | H | CH(Me)CH2 | bond | 339/341 | 1 |
| D18 | H | 3,5-di-F | H | H | H | CH(Me)CH2 | bond | 341 | 1 |
| D19 | H | 3-NO2 | H | H | H | CH=CH | bond | 334 | 15 |
| D20 | H | 3-NO2 | H | H | H | CH(CO2H)CH2 | bond | 380 | 1 |
| D21 | H | 3,4-di-F | H | H | H | (CH2)2 | bond | 327 | 1 |
| D22 | H | 3-NO2 | H | H | H | CH(CO2Me)CH2 | bond | 392 [M − H]- | 1 |
| D23 | H | 4-I | H | H | H | (CH2)2 | bond | 417 | 1 |
| D24 | H | 3-Cl | H | H | H | (CH2)2 | bond | 325/327 | 1 |
| D25 | H | 4-Br | H | H | H | (CH2)2 | bond | 369/171 | 1 |
| D26 | H | 3-Br | H | H | H | (CH2)2 | bond | 369/371 | 1 |
| D27 | H | 2-Me | H | H | H | (CH2)2 | bond | 305 | 1 |
| D28 | H | 3-F | H | H | H | (CH2)2 | bond | 309 | 1 |
| D29 | H | 2,4-di-Cl | H | H | H | (CH2)2 | bond | 359/361/363 | 1 |
| D30 | H | 2-Br | H | H | H | (CH2)2 | bond | 369/371 | 1 |
| D31 | H | 2-F | H | H | H | (CH2)2 | bond | 309 | 1 |
| D32 | H | 4-COPh | H | H | H | (CH2)2 | bond | 394 [M]- | 1 |
| D33 | H | 2-NO2 | H | H | H | (CH2)2 | bond | 336 | 1 |
| D34 | H | 3,4,5-tri-F | H | H | H | (CH2)2 | bond | 343 [M − H]- | 1 |
| D35 | H | 2-OEt | H | H | H | (CH2)2 | bond | 335 | 1 |
| D36 | H | 3-F | [4-Ethyl-piperazin-1-yl] | OMe | H | (CH2)2 | bond | 451 | 20 |
| D37 | H | 3-F | H | H | H | CH(Me)CH2 | bond | 323 | 1 |
| D38 | H | 2,3-di-F | H | H | H | CH(Me)CH2 | bond | 341 | 1 |
| D39 | H | 2-F | H | H | H | CH(Me)CM2 | bond | 323 | 1 |
| D40 | H | 2-Me | H | H | H | CH(Me)CH2 | bond | 319 | 1 |
| D41 | H | 2-Br | H | H | H | CH(Me)CH2 | bond | 383/385 | 1 |
| D42 | H | 4-OMe | H | H | H | CH(Me)CH2 | bond | 335 | 1 |
| D43 | H | 4-Cl | H | H | H | CH(Me)CH2 | bond | 339/341 | 1 |
| D44 | H | 4-I | H | H | H | CH(Me)CH2 | bond | 431 | 1 |
| D45 | H | 3-Me | H | H | H | CH(Me)CH2 | bond | 319 | 1 |
| D46 | H | 3,5-di-Me | H | H | H | CH(Me)CH2 | bond | 333 | 1 |
| D47 | H | 3-F | H | H | H | (CH2)3 | bond | 323 | 1 |
| D48 | H | 3-F | [4-(BOC)-Piperazin-1-yl] | OMe | H | (CH2)2 | bond | 521 [M − H]- | 20 |
| D49 | H | 3-F | [4-Me-Piperazin-1-yl] | Cl | H | (CH2)2 | bond | 441/443 | 20 |
| D50 | H | 3-F | [4-Me-Piperazin-1-yl] | Me | H | (CH2)2 | bond | 421 | 20 |
| D51 | H | 2-Cl | H | H | H | CH(CH2OH)CH2 | bond | 355/357 | 1 |
| D52 | H | 2-OMe | H | H | H | CH(CH2OH)CH2 | bond | 351 | 1 |
| D53 | H | 3-F | H | H | H | CH(CH2OH)CH2 | bond | 339 | 1 |
| D54 | H | 2,3-di-F | H | H | H | CH(CH2OH)CH2 | bond | 357 | 1 |

TABLE D-continued

Encompassing compounds of general formula (XXX-4), wherein group $R^2$ of formula (I) is a phenyl ring, optionally substituted by one or more substituents $R^{10}$ and the moiety —$NR^1R^3$ of formula (I) represents a heterocyclyl moiety of general formula (XXX-5), optionally substituted by substituents $R^{12a}$, $R^{12b}$ and $R^{12c}$ and substituents R, $R^{10}$, $R^{12a}$, $R^{12b}$, $R^{12c}$;X-Y and Z are listed in Table D.

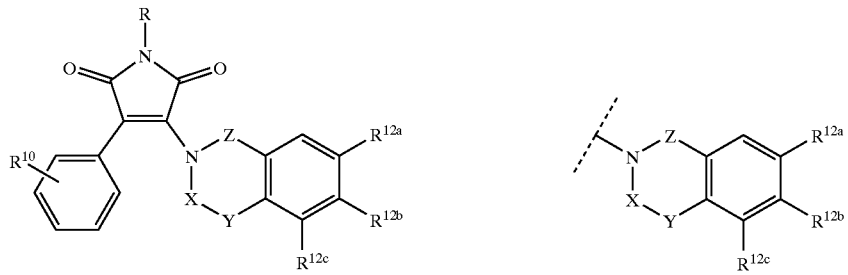

(XXX-4)                                                                 (XXX-5)

| Example No. | R | $R^{10}$ | $R^{12a}$ | $R^{12b}$ | $R^{12c}$ | X-Y | Z | [M + H]+ Observed; (Unless [M]- or [M − H]- are Indicated) | For Procedure See Example No. |
|---|---|---|---|---|---|---|---|---|---|
| D55 | H | 3,5-di-F | H | H | H | CH(CH2OH)CH2 | bond | 357 | 1 |
| D56 | H | 3,5-di-Me | H | H | H | CH(CH2OH)CH2 | bond | 349 | 1 |
| D57 | H | 2-Cl | H | H | H | CH2CH(Me) | bond | 339/341 | 1 |
| D58 | H | 3-F | H | H | H | CH2CH(Me) | bond | 323 | 1 |
| D59 | H | 3-F | [Piperazin-1-yl] | OMe | H | (CH2)2 | bond | 421 [M − H]- | 20 |
| D60 | H | 2-Cl | H | H | H | CH2CH(CH2OH) | bond | 355/357 | 20 |
| D61 | H | 3-F | H | H | H | CH2CH(CH2OH) | bond | 339 | 20 |
| D62 | H | 2,3-di-F | H | H | H | CH2CH(CH2OH) | bond | 357 | 20 |
| D63 | H | 2,3-di-F | H | H | H | CH2 | CH2 | 325 [M − H]- | 20 |
| D64 | H | 2,3-di-F | H | H | H | CH2C(Me2) | bond | 355 | 1 |
| D65 | H | 2,3-di-F | OMe | H | H | (CH2)2 | bond | 357 | 1 |
| D66 | H | 2,3-di-F | H | Br | H | (CH2)2 | bond | 405/407 | 1 |
| D67 | H | 2-Cl | H | H | H | CH2C(Me2) | bond | 353/355 | 1 |
| D68 | H | 2-Cl | H | F | H | (CH2)2 | bond | 343/345 | 1 |
| D69 | H | 2,3-di-F | NO2 | H | H | (CH2)2 | bond | 372 | 1 |
| D70 | H | 3,5-di-Me | OMe | H | H | (CH2)2 | bond | 349 | 1 |
| D71 | H | 2,3-di-F | H | H | H | CH2CH(Me) | bond | 341 | 1 |
| D72 | H | 2,3-di-F | OMe | OMe | H | (CH2)2 | bond | 387 | 1 |
| D73 | H | 2,3-di-F | H | H | Br | (CH2)2 | bond | 405/407 | 1 |
| D74 | H | 2,3-di-F | H | F | H | (CH2)2 | bond | 345 | 1 |
| D75 | H | 2,3-di-F | F | H | H | (CH2)2 | bond | 345 | 1 |
| D76 | H | 2,3-di-F | CF3 | Me | H | (CH2)2 | bond | 409 | 1 |
| D77 | H | 2,3-di-F | CF3 | OMe | H | (CH2)2 | bond | 425 | 1 |
| D78 | H | 2-Cl | OMe | H | H | (CH2)2 | bond | 355/357 | 1 |
| D79 | H | 2-Cl | H | H | Br | (CH2)2 | bond | 403/405/407 | 1 |
| D80 | H | 2-Cl | H | Br | H | (CH2)2 | bond | 403/405/407 | 1 |
| D81 | H | 2-Cl | F | H | H | (CH2)2 | bond | 343/345 | 1 |
| D82 | H | 2-Cl | NO2 | H | H | (CH2)2 | bond | 370/372 | 1 |
| D83 | H | 2-Cl | CF3 | Me | H | (CH2)2 | bond | 407/409 | 1 |
| D84 | H | 2-Cl | CF3 | OMe | H | (CH2)2 | bond | 423/425 | 1 |
| D85 | H | 3,5-di-Me | H | H | H | CH2CH(Me) | bond | 333 | 1 |
| D86 | H | 3,5-di-Me | H | H | H | CH2C(Me)2 | bond | 347 | 1 |
| D87 | H | 3,5-di-Me | OMe | OMe | H | (CH2)2 | bond | 379 | 1 |
| D88 | H | 3,5-di-Me | H | H | Br | (CH2)2 | bond | 397/399 | 1 |
| D89 | H | 3,5-di-Me | H | Br | H | (CH2)2 | bond | 397/399 | 1 |
| D90 | H | 3,5-di-Me | F | H | H | (CH2)2 | bond | 337 | 1 |
| D91 | H | 2,3-di-F | H | NHSO2Me | H | (CH2)2 | bond | 420 | 1 |
| D92 | H | 2-Cl | H | NHSO2Me | H | (CH2)2 | bond | 418/420 | 1 |
| D93 | H | 2,3-di-F | H | H | H | (CH2)2 | bond | 327 | 1 |
| D94 | H | 3,5-di-Me | H | H | H | (CH2)2 | bond | 319 | 1 |
| D95 | H | 2-Cl | OMe | OMe | H | (CH2)2 | bond | 385/387 | 1 |
| D96 | H | 3,5-di-Me | NO2 | H | H | (CH2)2 | bond | 364 | 1 |
| D97 | H | 2-Cl | H | H | H | CH(CONH2)CH2 | bond | 368/370 | 3 |
| D98 | H | 2,3-di-F | H | H | H | CH(CONH2)CH2 | bond | 370 | 3 |
| D99 | H | 3,5-di-Me | H | H | H | CH(CONH2)CH2 | bond | 362 | 3 |
| D100 | H | 3,5-di-Cl | H | H | H | (CH2)2 | bond | 359/361/363 | 1 |
| D101 | H | 2,3,5-tri-F | H | H | H | (CH2)2 | bond | 343 [M − H]- | 1 |
| D102 | H | 3-NO2 | H | H | H | CH(CH2OH)CH2 | bond | 366 | 13 |
| D103 | H | 4-I | H | H | H | CH(CH2OH)CH2 | bond | 447 | 13 |
| D104 | H | 4-I | H | H | H | CH(CO2H)CH2 | bond | 415 [M − CO2H]- | 13 |
| D105 | H | 4-I | H | H | H | C(=O)—C(Me)2 | bond | 459 | 15 |
| D106 | H | 3-NO2 | H | H | H | C(=O)—C(Me)2 | bond | 378 | 15 |

TABLE D-continued

Encompassing compounds of general formula (XXX-4), wherein group $R^2$ of formula (I) is a phenyl ring, optionally substituted by one or more substituents $R^{10}$ and the moiety —$NR^1R^3$ of formula (I) represents a heterocyclyl moiety of general formula (XXX-5), optionally substituted by substituents $R^{12a}$, $R^{12b}$ and $R^{12c}$ and substituents R, $R^{10}$, $R^{12a}$, $R^{12b}$, $R^{12c}$; X-Y and Z are listed in Table D.

(XXX-4) (XXX-5)

| Example No. | R | $R^{10}$ | $R^{12a}$ | $R^{12b}$ | $R^{12c}$ | X-Y | Z | [M + H]+ Observed; (Unless [M]- or [M − H]- are Indicated) | For Procedure See Example No. |
|---|---|---|---|---|---|---|---|---|---|
| D107 | H | 3-NO2 | H | H | H | C(=O)—O— | bond | 352 | 15 |
| D108 | H | 4-I | H | H | H | C(=O)—O— | bond | 433 | 15 |
| D109 | H | 3-NO2 | H | H | H | CH(CH2OH)CH2 Isomer 1 | bond | 366 | 21 |
| D110 | H | 3-NO2 | H | H | H | CH(CH2OH)CH2 Isomer 2 | bond | 366 | 21 |
| D111 | H | 4-I | H | H | H | CH(CH2OH)CH2 Isomer 1 | bond | 447 | 21 |
| D112 | H | 3,5-di-F | H | H | H | CH(CH2OH)CH2 Isomer 1 | bond | 341 | 21 |
| D113 | H | 4-I | H | H | H | CH(CH2OH)CH2 Isomer 2 | bond | 447 | 21 |
| D114 | H | 3,5-di-F | H | H | H | CH(CH2OH)CH2 Isomer 2 | bond | 341 | 21 |

TABLE E

Encompassing compounds of general formula (XXX-6), wherein group $R^2$ of formula (I) is a (3-heterocyclyl) moiety (XXX-7), optionally substituted by one or more substituents $R^{13}$ and group $R^3$ of formula (I) is a phenyl ring, optionally substituted by one or more substituents $R^{11}$ and substituents R, $R^1$, $R^{11}$ and $R^{13}$ are listed in Table E.

(XXX-6) (XXX-7)

| Example No. | R | $R^1$ | $R^{11}$ | $R^{13}$ | A | [M + H]+ Observed; (Unless [M]- or [M − H]- are Indicated) | For Procedure See Example No. |
|---|---|---|---|---|---|---|---|
| E1 | H | H | 3-Br | 4,5-[(—CH=CH—)2] | N(Me) | 396/398 | 4 |
| E2 | H | H | 4-Me | 4,5-[(—CH=CH—)2] | N(Me) | 332 | 4 |
| E3 | H | H | 4-SMe | 4,5-[(—CH=CH—)2] | N(Me) | 364 | 4 |
| E4 | H | H | 3-Br-4-Me | 4,5-[(—CH=CH—)2] | O | 397/399 | 4 |
| E5 | H | H | 3-Br-4-Me | H | S | 363/365 | 4 |
| E6 | H | H | 3-Cl | H | S | 303/305 [M − H]- | 1 |
| E7 | H | H | 3,4-[S—CH=N] | 4,5-[(—CH=CH—)2] | N(Me) | 375 | 4 |

TABLE E-continued

Encompassing compounds of general formula (XXX-6), wherein group $R^2$ of formula (I) is a (3-heterocyclyl) moiety (XXX-7), optionally substituted by one or more substituents $R^{13}$ and group $R^3$ of formula (I) is a phenyl ring, optionally substituted by one or more substituents $R^{11}$ and substituents R, $R^1$, $R^{11}$ and $R^{13}$ are listed in Table E.

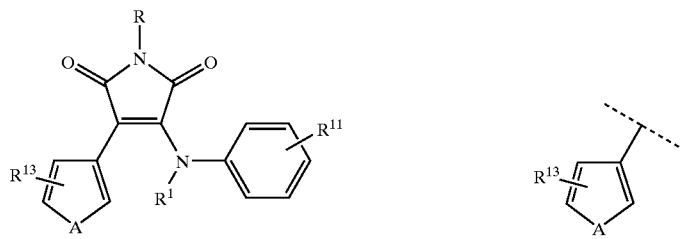

(XXX-6)                (XXX-7)

| Example No. | R | $R^1$ | $R^{11}$ | $R^{13}$ | A | $[M + H]^+$ Observed; (Unless $[M]^-$ or $[M - H]^-$ are Indicated) | For Procedure See Example No. |
|---|---|---|---|---|---|---|---|
| E8  | H | H | 3-OPh           | 4,5-[(—CH=CH—)2] | N(Me) | 410                    | 4  |
| E9  | H | H | 3,4-[(CH2)3]    | 4,5-[(—CH=CH—)2] | N(Me) | 358                    | 4  |
| E10 | H | H | 3-SMe           | H                | S     | 315 [M − H]−           | 1  |
| E11 | H | H | 4-Me            | H                | S     | 283 [M − H]−           | 1  |
| E12 | H | H | H               | H                | S     | 269 [M − H]−           | 1  |
| E13 | H | H | 3-OPh           | H                | S     | 361 [M − H]−           | 1  |
| E14 | H | H | 3,4-[(CH2)3]    | H                | S     | 309 [M − H]−           | 1  |
| E15 | H | H | 3-Br            | H                | S     | 347/349 [M − H]−       | 1  |
| E16 | H | H | 4-SMe           | H                | S     | 315 [M − H]−           | 1  |
| E17 | H | H | 3,5-di-Br-4-OH  | H                | S     | 441/443/445 [M − H]−   | 1  |
| E18 | H | H | 3-Cl            | 4,5-[(—CH=CH—)2] | S     | 355/357                | 1  |
| E19 | H | H | 3,5-di-Cl-4-OH  | H                | S     | 353/355/357 [M − H]−   | 1  |
| E20 | H | H | 3,5-di-Cl-4-OH  | 4,5-[(—CH=CH—)2] | S     | 405/407/409            | 13 |
| E21 | H | H | 3-CO2H-4-Cl     | H                | S     | 349/341                | 1  |
| E22 | H | H | 3,4-[OCH2O]     | H                | S     | 315                    | 1  |
| E23 | H | H | 3-Cl-4-OH       | H                | S     | 319/321 [M − H]−       | 1  |
| E24 | H | H | 3,5-di-F        | H                | s     | 307                    | 1  |
| E25 | H | H | 3-CH2OH         | H                | s     | 299 [M − H]−           | 1  |
| E26 | H | H | 3-OH            | H                | S     | 287                    | 1  |
| E27 | H | H | 3,4-[OCH2O]     | 4,5-[(—CH=CH—)2] | S     | 365                    | 1  |
| E28 | H | H | 3-Cl-4-OH       | 4,5-[(—CH=CH—)2] | S     | 371/373                | 1  |
| E29 | H | H | 3-OH            | 4,5-[(—CH=CH—)2] | S     | 337                    | 1  |
| E30 | H | H | 4-CH2SO2NHMe    | H                | S     | 378                    | 1  |

TABLE F

Encompassing compounds of general formula (XXX-8), wherein group $R^2$ of formula (I) is a moiety of formula (XXX-9), optionally substituted by substituents $R^{14}$ and $R^{15}$ and group $R^3$ of formula (I) is a phenyl ring, optionally substituted by one or more substituents $R^{11}$ and substituents R, $R^1$, $R^{11}$, $R^{14}$ and $R^{15}$ are listed in Table F.

(XXX-8)        (XXX-9)

| Example No. | R | $R^1$ | $R^{11}$ | $R^{14}$ | $R^{15}$ | [M + H]+ Observed; (Unless [M]− or [M − H]− are Indicated) | For Procedure See Example No. |
|---|---|---|---|---|---|---|---|
| F1 | H | H | 3,4-[(CH2)3] | H | Me | 360 [M − H]− | 7 |
| F2 | H | H | 3,4-[(CH2)3] | H | NH[3-F—Ph] | 456 [M]− | 8 |
| F3 | H | H | 3,4-[(CH2)3] | H | NH(CH2)2Ph | 467 | 8 |
| F4 | H | H | 3,4-[(CH2)3] | H | NH[Cyclohexyl] | 443 [M − H]− | 8 |
| F5 | H | H | 3,4-[(CH2)3] | H | NHCH2CH=CH2 | 403 | 8 |
| F6 | H | H | 3,4-[(CH2)3] | H | Ph | 422 [M − H]− | 9 |
| F7 | H | H | 3,4-[(CH2)3] | H | CH2Ph | 436 [M − H]− | 9 |
| F8 | H | H | 3,4-[(CH2)3] | H | trans-CH=CHPh | 450 | 9 |
| F9 | H | H | 3,4-[(CH2)3] | H | n-Pr | 390 | 9 |
| F10 | H | H | 3,4-[(CH2)3] | H | NHEt | 389 [M − H]− | 8 |
| F11 | H | H | 3,4-[(CH2)3] | H | NH[3-OMe-Ph] | 469 | 8 |

TABLE G

Encompassing compounds of general formula (XXX-10), wherein group $R^2$ of formula (I) is a phenyl ring, optionally substituted by one or more substituents $R^{10}$ and group $R^3$ of formula (I) is a moiety of formula (XXX-11), optionally substituted by one or more substituents $R^{16}$ and $R^{17}$ and substituents R, $R^1$, $R^{10}$, W, $R^{16}$ and $R^{17}$ are listed in Table G. The position of substituent $R^{16}$ is indicated by the locants 2 or 3 in Structure (XXX-10).

(XXX-10)        (XXX-11)

| Example No. | R | $R^1$ | $R^{10}$ | W | $R^{16}$ | $R^{17}$ | [M + H]+ Observed; (Unless [M]− or [M − H]− are Indicated) | For Procedure See Example No. |
|---|---|---|---|---|---|---|---|---|
| G1 | H | H | 2-OMe | S | 3-CO2H | 2-CO2H | 491 | 1 |
| G2 | H | H | 4-Cl | S | H | 3-CO2H | 449/451 [M − H]− | 1 |
| G3 | H | H | 4-Cl | S | 3-CO2Et | 2-CO2Et | 550/552 [M]− | 1 |
| G4 | H | H | 4-Cl | S | 3-CO2Me | 4-Cl | 497/499/501 [M − H]− | 1 |
| G5 | H | H | 4-Cl | S | 3-CO2H | 2-CONHMe | 508/510 | 1 |
| G6 | H | H | 4-Cl | S | H | 4-NO2 | 450/452 [M − H]− | 1 |
| G7 | H | H | 4-Cl | O | H | 4-Cl | 425/427/429 | 1 |

TABLE G-continued

Encompassing compounds of general formula (XXX-10), wherein group $R^2$ of formula (I) is a phenyl ring, optionally substituted by one or more substituents $R^{10}$ and group $R^3$ of formula (I) is a moiety of formula (XXX-11), optionally substituted by one ormore substituents $R^{16}$ and $R^{17}$ and substituents R, $R^1$, $R^{10}$, W, $R^{16}$ and $R^{17}$ are listed in Table G.
The position of substituent $R^{16}$ is indicated by the locants 2 or 3 in Structure (XXX-10).

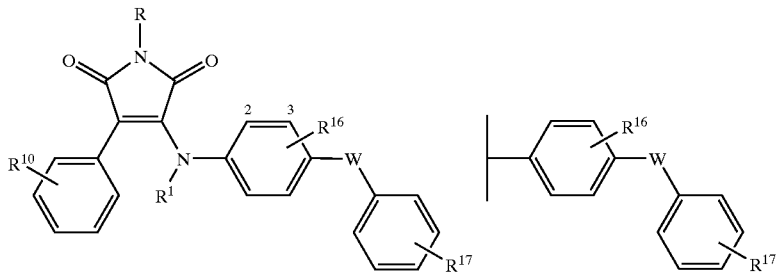

(XXX-10)                    (XXX-11)

| Example No. | R | $R^1$ | $R^{10}$ | W | $R^{16}$ | $R^{17}$ | $[M + H]^+$ Observed; (Unless $[M]^-$ or $[M - H]^-$ are Indicated) | For Procedure See Example No. |
|---|---|---|---|---|---|---|---|---|
| G8  | H | H | 4-Cl     | S | H         | 2-CO2H    | 451/453           | 1 |
| G9  | H | H | 4-Cl     | S | 3-CO2H    | H         | 449/451 [M − H]−  | 1 |
| G10 | H | H | 4-OMe    | S | 3-CO2H    | 2-CO2H    | 489 [M − H]−      | 1 |
| G11 | H | H | 2-Cl     | S | 3-CO2H    | 2-CO2H    | 493 [M − H]−      | 1 |
| G12 | H | H | 4-Cl     | S | 3-CO2H    | 3-CO2H    | 495/497           | 1 |
| G13 | H | H | 2,3-di-F | S | H         | 3-CO2H    | 453               | 1 |
| G14 | H | H | 2,3-di-F | S | 3-CONHMe  | 2-CONHMe  | 523               | 1 |
| G15 | H | H | 2,3-di-F | S | 3-CO2H    | 2-CO2Et   | 523 [M − H]−      | 1 |
| G16 | H | H | 2,3-di-F | S | H         | 4-CO2H    | 451 [M − H]−      | 1 |
| G17 | H | H | 2,3-di-F | S | 3-CO2Et   | 4-CO2H    | 525               | 1 |

TABLE H

Encompassing compounds of general formula (XXX-12), wherein group $R^2$ of formula (I) is a (2-heterocyclyl) moiety (XXX-13), optionally substituted by one or more substituents $R^{18}$ and group $R^3$ of formula (I) is a phenyl ring, optionally substituted by one or more substituents $R^{11}$ and substituents R, $R^1$, $R^{11}$ and $R^{18}$ are listed in Table H.

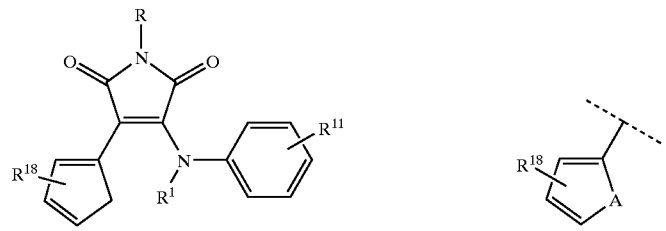

(XXX-12)                    (XXX-13)

| Example No. | R | $R^1$ | $R^{11}$ | $R^{18}$ | A | $[M + H]^+$ Observed; (Unless $[M]^-$ or $[M - H]^-$ are Indicated) | For Procedure See Example No. |
|---|---|---|---|---|---|---|---|
| H1 | H | H | 3-Cl          | H                   | S | 305/307       | 1  |
| H2 | H | H | 3-Cl          | 3-Me-4,5-[(—CH=CH—)2] | S | 369/371     | 1  |
| H3 | H | H | 3,5-di-Cl-4-OH | H                   | S | 355/357/359   | 1  |
| H4 | H | H | 3,5-di-Cl-4-OH | 3-Me-4,5-[(—CH=CH—)2] | S | 419/421/423 | 13 |

TABLE I

Encompassing compounds of general formula (XXX-14), wherein the moiety $NR^1R^3$ of formula (I) is represented by a general substituent $R^{19}$ and substituents R, $R^2$ and $R^{19}$ are listed in Table I.

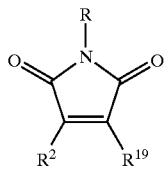

(XXX-14)

| Example No. | R | $R^2$ | $R^{19}$ | $[M + H]^+$ Observed; (Unless $[M]^-$ or $[M - H]^-$ are Indicated) | For Procedure See Example No. |
|---|---|---|---|---|---|
| I1 | H | 3-Thienyl | 1-Indolinyl | 297 | 1 |
| I2 | H | 2-Thienyl | 1-Indolinyl | 297 | 1 |
| I3 | H | 4-Cl—Ph | (3-Amino-1-pyridinium chloride) | 301/303 | 19 |
| I4 | H | 2-Thienyl | 2-Me-Indolin-1-yl | 311 | 1 |
| I5 | H | 3-Thienyl | 2-Me-Indolin-1-yl | 311 | 1 |
| I6 | H | 2,4-di-Cl—Ph | [1,3,3-Trimethyl-6-azabicyclo[3,2,1]octan-6-yl] | 393/395/397 | 1 |
| I7 | H | 2,4-di-Cl—Ph | [1-Phenyl-1,3,8-trazaspiro-[4,5]-decan-4-one-8-yl] | 471/473/475 | 1 |

What is claimed is:

1. 3-(3-chloro-4-hydroxyphenylamino)-4-(2-nitrophenyl)-1H-pyrrole-2,5-dione or a pharmaceutically acceptable salt or solvate thereof.

2. A pharmaceutical composition comprising 3-(3-chloro-4-hydroxyphenylamino)-4-(2-nitrophenyl)-1H-pyrrole-2,5-dione or a pharmaceutically acceptable salt or solvate thereof and a pharmaceutically acceptable carrier.

* * * * *